US012606529B2

(12) United States Patent
Tavis et al.

(10) Patent No.: US 12,606,529 B2
(45) Date of Patent: Apr. 21, 2026

(54) SULFUR AND AMIDE TROPOLONE INHIBITORS OF NUCLEOTIDYL TRANSFERASES AND USES THEREFOR

(71) Applicants: Saint Louis University, St. Louis, MO (US); Research Foundation of the City University of New York, New York, NY (US)

(72) Inventors: John Edwin Tavis, Kirkwood, MO (US); Lynda Anne Morrison, Webster Groves, MO (US); Maureen Jeanette Donlin, Kirkwood, MO (US); Ryan P. Murelli, Belleville, NJ (US)

(73) Assignees: Saint Louis University, St. Louis, MO (US); Research Foundation of the City University of New York, New York, NY (US)

(*) Notice: Subject to any disclaimer, the term of this patent is extended or adjusted under 35 U.S.C. 154(b) by 232 days.

(21) Appl. No.: 17/608,256

(22) PCT Filed: May 3, 2020

(86) PCT No.: PCT/US2020/031234
§ 371 (c)(1),
(2) Date: Nov. 2, 2021

(87) PCT Pub. No.: WO2020/227180
PCT Pub. Date: Nov. 12, 2020

(65) Prior Publication Data
US 2022/0348546 A1 Nov. 3, 2022

Related U.S. Application Data

(60) Provisional application No. 62/842,955, filed on May 3, 2019.

(51) Int. Cl.

| | |
|---|---|
| ***C07D 229/02*** | (2006.01) |
| ***A61P 31/12*** | (2006.01) |
| ***C07C 31/12*** | (2006.01) |
| ***C07C 233/58*** | (2006.01) |
| ***C07C 233/60*** | (2006.01) |
| ***C07C 233/63*** | (2006.01) |
| ***C07C 271/22*** | (2006.01) |

(Continued)

(52) U.S. Cl.
CPC ............ *C07D 229/02* (2013.01); *A61P 31/12* (2018.01); *C07C 233/58* (2013.01); *C07C 233/60* (2013.01); *C07C 233/63* (2013.01); *C07C 271/22* (2013.01); *C07C 311/18* (2013.01); *C07C 317/24* (2013.01); *C07D 209/20* (2013.01); *C07D 211/26* (2013.01); *C07D 213/75* (2013.01); *C07D 239/42* (2013.01); *C07D 271/12* (2013.01); *C07D 277/22* (2013.01); *C07D 295/185* (2013.01); *C07D 307/68* (2013.01); *C07D 317/28* (2013.01); *C07D 319/20* (2013.01); *C07D 333/20* (2013.01); *C07D 333/34* (2013.01); *C07D 413/04* (2013.01); *C07C 2601/18* (2017.05)

(58) Field of Classification Search
None
See application file for complete search history.

(56) References Cited

U.S. PATENT DOCUMENTS

| | | | |
|---|---|---|---|
| 10,329,542 | B2 | 6/2019 | Tavis |
| 10,463,664 | B2 | 11/2019 | Tavis |

(Continued)

FOREIGN PATENT DOCUMENTS

| | | |
|---|---|---|
| WO | WO 2014/085568 | 6/2014 |
| WO | WO 2015/077774 | 5/2015 |

(Continued)

OTHER PUBLICATIONS

Database Registry Chemical Abstracts Service, Columbus, Ohio, Accession No. RN 2172794-73-7, Entered STN: Feb. 2, 2018.*

(Continued)

*Primary Examiner* — Samantha L Shterengarts
(74) *Attorney, Agent, or Firm* — pH IP Law

(57) ABSTRACT

The present disclosure provides inhibitors of microorganisms including viruses and fungi of the formula (I) or (II) wherein the variables are defined herein. Also provided are methods of treatment using these agents in the treatment of infections of microorganisms such as viruses and fungi.

(I)

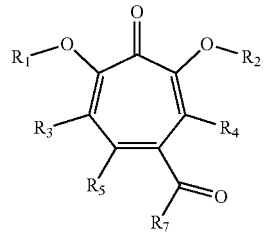

(II)

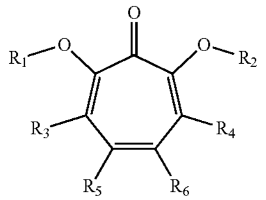

16 Claims, 1 Drawing Sheet

Specification includes a Sequence Listing.

(51) Int. Cl.

| | |
|---|---|
| ***C07C 311/18*** | (2006.01) |
| ***C07C 317/24*** | (2006.01) |
| ***C07D 209/20*** | (2006.01) |
| ***C07D 211/26*** | (2006.01) |
| ***C07D 213/75*** | (2006.01) |
| ***C07D 239/42*** | (2006.01) |
| ***C07D 271/12*** | (2006.01) |
| ***C07D 277/22*** | (2006.01) |
| ***C07D 295/185*** | (2006.01) |
| ***C07D 307/68*** | (2006.01) |
| ***C07D 317/28*** | (2006.01) |
| ***C07D 319/20*** | (2006.01) |
| ***C07D 333/20*** | (2006.01) |
| ***C07D 333/34*** | (2006.01) |
| ***C07D 413/04*** | (2006.01) |

(56) References Cited

U.S. PATENT DOCUMENTS

| | | | |
|---|---|---|---|
| 10,980,754 | B2 | 4/2021 | Donlin |
| 11,420,922 | B2 | 8/2022 | Tavis |
| 2018/0169083 | A1 | 6/2018 | Tavis |

FOREIGN PATENT DOCUMENTS

| | | |
|---|---|---|
| WO | WO 2016/201243 | 12/2016 |
| WO | WO 2016/201306 | 12/2016 |
| WO | WO 2017/156194 | 9/2017 |
| WO | WO 2017/184752 | 10/2017 |

OTHER PUBLICATIONS

Database Registry Chemical Abstracts Service, Columbus, Ohio, Accession No. RN 2006980-59-0, Entered STN: Oct. 6, 2016.*

Database Registry Chemical Abstracts Service, Columbus, Ohio, Accession No. RN 2236580-32-6, Entered STN: Aug. 8, 2018.*

Database Registry Chemical Abstracts Service, Columbus, Ohio, Accession No. RN 2006980-73-8, Entered STN: Oct. 6, 2016.*

Boehmer & Lehman, "Herpes simplex virus DNA replication", *Ann. Rev. Biochem.*, 66:347-384, 1997.

Bratton et. al., "Approaches to Antifungal Therapies and Their Effectiveness among Patients with Cryptococcosis", *Antimicrob Agents Chemother*. 57:2485-2495, 2013.

Frank et al., "Cloning of the cDNA encoding the large subunit of human RNase HI, a homologue of the prokaryotic RNase HII", *PNAS*, 95(22:12872-12877, 1998.

Cai et al., "Hepatitis B virus replication is blocked by a 2-hydroxyisoquinoline-1,3(2H,4H)-dione (HID) inhibitor of the viral ribonuclease H activity", *Antivir. Res.*, 108:48-55, 2014.

Chen et al., "Targeting Metalloenzymes for Therapeutic Intervention", *Chem. Rev.*, 119 : 1323-1455, 2019.

Donlin et al., "Troponoids Can Inhibit Growth of the Human Fungal Pathogen *Cryptococcus neoformans", Antimicrobial Agents and Chemotherapy*, 61(4):302574-16.

Duan, "Acyclovir-Resistant Corneal HSV-1 Isolates from Patients with Herpectic Keratitis", *J. Infect. Dis.*, 198(5):659-663, 2008.

Edwards et al., "Inhibition of hepatitis B virus replication by N-hydroxyisoquinolinediones and related polyoxygenated heterocycles", *Antivir. Res.*, 143:205-207, 2017.

Edwards et al., "Inhibition of HBV replication by N-hydroxyisoquinolinedione and N-hydroxypyridinedione ribonuclease H inhibitors", *Antivir. Res.*, 164:70-80, 2019.

Field & Vere Hodge, "Recent developments in anti-herpesvirus drugs", *Br. Med. Bull.*, 106:213-249, 2013.

Frobert et al., "Sequence Analysis of Herpes Simplex Virus 1 Thymidine Kinase and DNA Polymerase Genes from over 300 Clinical Isolates from 1973 to 2014 Finds Novel Mutations That May Be Relevant for Development of Antiviral Resistance", *Antivir. Res.*, 111:36-41, 2014.

Gerelsaikhan et al., "Hepatitis B Virus Nucleocapsid Envelopment Does Not Occur without Genomic DNA Synthesis", *J. Virol.* 70, 4269-4274, 1996.

Goedken et al., "Co-crystal of *Escherichia coli* RNase HI with $MN^{2+}$ Ions Reveals Two Divalent Metals Bound in the Active Site", *J. Biol. Chem.* 276, 7266-7271, 2001.

Himmel et al., "Structure of HIV-1 Reverse Transcriptase with the Inhibitor β-Thujaplicinol Bound at the RNase H Active Site", *Structure*, 17:1625-1635, 2009.

Hostomsky et al., "Ribonuclease H," in: Linn, S.M., Lloyd, R.S., Roberts, R.J. (Eds.), Nulceases. Cold Spring Harbor Laboratory Press, Plainview, NY, pp. 341-376, 1993.

Hu et al., "β-Thujaplicinol inhibits hepatitis B virus replication by blocking the viral ribonuclease H activity", *Antivir. Res.*, 99:221-229, 2013.

International Preliminary Report on Patentability for International Application No. PCT/US2020/031234 dated Nov. 2, 2021, 9 pages.

International Search Report and Written Opinion for International Application No. PCT/US2020/031234 dated Oct. 14, 2020, 13 pages.

Invitation to Pay Additional Fees for International Application No. PCT/US2020/031234 dated Aug. 3, 2020, 3 pages.

Johnston, "Standard-dose and high-dose daily antiviral therapy for short episodes of genital HSV-2 reactivation: three randomized, open-label, cross-over trials", *Lancet*, 379:641-647, 2012.

Katayanagi et al., "Three-dimensional structure of ribonuclease H from *E. coli", Nature* 347: 306-309, 1990.

Keck et al., "Activation/Attenuation Model for RNase H a One-Metal Mechanism with second-metal Inhibition", *J. Biol. Chem.* 273, 34128-34133, 1998.

King, "History, pharmacokinetics, and pharmacology of acyclovir", *J. Amer. Acad. Dermatol.*, 18:176-179, 1988.

Klumpp et al., *Nucleic Acids Res.* 31, 6852-6859, 2004.

Lai et al., "Crystal structure of archael RNase HII : a homologue of human major RNase H", *Structure* 8:897-904, 2000.

Lima et al., "Human RNases H", *Methods Enzymol.* 341:430-440, 2001.

Lomonosova et al., "Efficacy and cytotoxicity in cell culture of novel α-hydroxytropolone inhibitors of hepatitis B virus ribonuclease H", *Antivir Res.*, 144: 164-172, 2017.

Long et al., "Efficacy of Hepatitis B Virus Ribonuclease H Inhibitors, a New Class of Replication Antagonists, in FRG Human Liver Chimeric Mice", *Antivir. Res.*, 149:41-47, 2018.

Lortholary, "Management of Cryptococcal Meningitis in AIDS: The Need for Specific Studies in Developing Countries", *Clin Infect Dis.* 45:81-83, 2007.

Lu et al., "Hydroxylated Tropolones Inhibit Hepatitis B Virus Replication by Blocking Viral Ribonuclease H Activity", *Antimicrob. Agents Chemother.*, 59:1070-1079, 2015.

Lu et al., "Hepatitis B virus genetic diversity has minimal impact on sensitivity of the viral ribonuclease H to inhibitors", *Antivir. Res.*, 135:24-34, 2016.

Mdodo et. al., "The Prevalence, clinical Features, Risk Factors and Outcome Associated with Cryptococcal Meningitis in HIV Positive Patients in Kenya", *East Afr Med J.* 87:481-487, 2010.

Meck et al., "The biology and synthesis of a-hydroxytropolones", *Med. Chem. Comm.*, 5:842-852, 2014.

Nowotny et al., "Crystal Structures of RNase H Bound to an RNA/DNA Hybrid: Substrate Specificity and Metal-Dependent Catalysis", *Cell* 121: 1005-1016, 2005.

Nowotny, "Retroviral integrase superfamily: the structural perspective", *EMBO Rep.* 10:144-151, 2009.

Omoto et al., *Lancet. Gastroenterol. Hepatol.*, 3:383-403, 2018.

Parker et al., "Crystal Structure of a PIWI protein suggests mechanisms for siRNA recognition and slicer activity", *EMBO J.* 23: 4727-4737, 2004.

Rajasingham et. al., "Global burden of disease of HIV-associated cryptococcal meningitis: an updated analysis", *Lancet Infect Dis.* 17(8):873-881, 2017.

Schumacher et al., "The HSV-1 Exonuclease, UL12, Stimulates Recombination by a Single Strand Annealing Mechanism", *PLoS Pathog.*, 8(8) e1002862, 2012.

(56) References Cited

OTHER PUBLICATIONS

Selvarajan et al., "The Structure of the Herpes Simplex Virus DNA-Packaging Terminase pUL15 Nuclease Domain Suggests an Evolutionary Lineage among Eukaryotic and Prokaryotic Viruses", *J Virol.*, 87:7140-7148, 2013.
Shoham and Marr, "Invasive fungal infections in solid organ transplant recipients", *Future Microbiology*, 7(5), 2012.
Song et al., "Crystal structure of Argonaute and its implications for RISC slicer activity" *Science* 305: 1434-1437, 2004.
Tavis et al., "Chemical Approaches to Inhibiting the Hepatitis B Virus Ribonuclease H", *ACS Infect. Dis.*, 5, 655-658, 2019.
Tavis et al., "The Hepatitis B Virus Ribonuclease H Is Sensitive to Inhibitors of the Human Immunodeficiency Virus Ribonuclease H an dIntegrase Enzymes", *PLoS Pathogens* 9:e1003125, 2013.
Van Velzen, "Acyclovir Prophylaxis Predisposes to Antiviral-Resistant Recurrent Herpetic Keratitis", *J. Infect. Dis.*, 208:1359-1365, 2013.
Vere Hodge & Field, "Chapter One—Antiviral Agents for Herpes Simplex Virus", *Adv. Pharmacol.*, 67:1-38, 2013.
Wang et al., "Identification and characterization of acyclovir-resistant clinical HSV-1 isolates from children", *J Clin Virol*, 52(2), 107-112, 2011.
Yang et al., "Structure of Ribonuclease H Phased at 2 Å Resolution by MAD Analysis of the Selenomethionyl Protein", *Science* 249: 1398-1405, 1990.
Yang, "Baloxavir Marboxil: The First Cap-Dependent Endonuclease Inhibitor of the Treatment of Influenza", *Sage Journals*, 53(7), 2019.
Yang and Steitz, „Recombining the Structures of HIV integrase, RuvC and Rnase H, *Structure*, 3, 131-134, 1995.
Zhang et al., "Free Energy-Based Virtual Screening and Optimization of RNase H Inhibitors of HIV-1 Reverse Transcriptase", *ACS Omega*, 1 :435-447, 2016.

* cited by examiner

920 $IC_{50}$ = 3.5 μM
1097 $IC_{50}$ = 313 μM
1098 $IC_{50}$ = 346 μM
1099 $IC_{50}$ = 108 μM
1100 $IC_{50}$ = 203 μM
1101 $IC_{50}$ = 544 μM
1131 $IC_{50}$ = 65.8 μM

SEQUENCE LISTING

```
<160> NUMBER OF SEQ ID NOS: 8

<210> SEQ ID NO 1
<211> LENGTH: 26
<212> TYPE: DNA
<213> ORGANISM: Artificial sequence
<220> FEATURE:
<223> OTHER INFORMATION: Synthetic oligo

<400> SEQUENCE: 1

catgaacaag agatgattag gcagag                                          26


<210> SEQ ID NO 2
<211> LENGTH: 22
<212> TYPE: DNA
<213> ORGANISM: Artificial sequence
<220> FEATURE:
<223> OTHER INFORMATION: Synthetic oligo

<400> SEQUENCE: 2

ggaggctgta ggcataaatt gg                                              22


<210> SEQ ID NO 3
<211> LENGTH: 20
<212> TYPE: DNA
<213> ORGANISM: Artificial sequence
<220> FEATURE:
<223> OTHER INFORMATION: Synthetic oligo

<400> SEQUENCE: 3

ctgcgcacca gcaccatgca                                                 20


<210> SEQ ID NO 4
<211> LENGTH: 19
<212> TYPE: DNA
<213> ORGANISM: Artificial sequence
<220> FEATURE:
<223> OTHER INFORMATION: Synthetic oligo

<400> SEQUENCE: 4

gcagatgaga aggcacaga                                                  19


<210> SEQ ID NO 5
<211> LENGTH: 17
<212> TYPE: DNA
<213> ORGANISM: Artificial sequence
<220> FEATURE:
<223> OTHER INFORMATION: Synthetic oligo

<400> SEQUENCE: 5

cttctccgtc tgccgtt                                                    17


<210> SEQ ID NO 6
<211> LENGTH: 22
<212> TYPE: DNA
<213> ORGANISM: Artificial sequence
<220> FEATURE:
<223> OTHER INFORMATION: Synthetic oligo
```

-continued

```
<400> SEQUENCE: 6

agtccgcgta aagagaggtg cg                                              22


<210> SEQ ID NO 7
<211> LENGTH: 18
<212> TYPE: DNA
<213> ORGANISM: Artificial sequence
<220> FEATURE:
<223> OTHER INFORMATION: Synthetic oligo

<400> SEQUENCE: 7

gaucugagcc ugggagcu                                                   18


<210> SEQ ID NO 8
<211> LENGTH: 18
<212> TYPE: DNA
<213> ORGANISM: Artificial sequence
<220> FEATURE:
<223> OTHER INFORMATION: Synthetic oligo

<400> SEQUENCE: 8

agctcccagg ctcagatc                                                   18
```

SULFUR AND AMIDE TROPOLONE INHIBITORS OF NUCLEOTIDYL TRANSFERASES AND USES THEREFOR

The present application is a national phase application under 35 U.S.C. § 371 of International Application No. PCT/US2020/031234, filed May 3, 2020, which claims the priority benefit of U.S. Provisional Application Ser. No. 62/842,955, filed May 3, 2019, the entire contents of each of which are hereby incorporated by reference.

GOVERNMENT SUPPORT CLAUSE

This invention was made with government support under Grant No. R01 AI122669 awarded by the National Institutes of Health. The government has certain rights in the invention.

BACKGROUND

I. Field

The disclosure relates to the fields of pathology, virology, molecular biology and pharmaceuticals. More specifically, the disclosure relates to inhibitors for the treatment and prevention of diseases associated with an infection of microorganisms including viruses such as herpesvirus, hepatitis B or fungi such as *Cryptococcus neoformans.*

II. Related Art

Nature contains a myriad of different pathogenic microorganisms such as fungi, bacteria, protozoans, and viruses. Two of the primary viral families which have a significant impact on health are herpesvirus and hepatitis. The Herpesviridae is a large family of DNA viruses that cause diseases in vertebrates, including humans. At least six species of Herpesviridae—herpes simplex virus 1 (HSV-1) and HSV-2 (both of which can cause orolabial herpes and genital herpes), Varicella-zoster virus (which causes chickenpox and shingles), Epstein-Barr virus (which causes mononucleosis), Cytomegalovirus (which causes mental retardation and deafness in neonates), and Human herpesvirus 6B (which causes roseola infantum and febrile seizures)—are extremely widespread among humans. More than 90% of adults have been infected with at least one of these and a latent form of the virus remains in most people. Alternatively, one of the hepatitis viruses, hepatitis B virus (HBV) is a hepatotropic DNA virus that replicates by reverse transcription (Hostomsky et al., 1993). It chronically infects >350 million people world-wide and kills up to 1.2 million patients annually by inducing liver failure and liver cancer (Steitz, 1995; Katayanagi et al., 1990; Yang et al., 1990; Lai et al., 2000).

HSV replicates by DNA-dependent DNA replication catalyzed by an HSV DNA polymerase whose direct product is a concatemer of newly synthesized genomes. Key to its replication mechanism are several nuclease cleavages involved in intramolecular DNA recombination and cleaving the concatemeric DNAs to unit length. The enzymes involved in these cleavages include the pUL30 polymerase, the pUL12 nuclease and the pUL15 terminase (Boehmer & Lehman, 1997; Schumacher et al., 2012; Selvarajan et al., 2013).

Infections of these types of viruses are generally treated using drugs which target the replication process restricting the conversion of the viral RNA into DNA into or the direct copying of the DNA. The drugs, acyclovir and ganciclovir, are nucleoside analog drugs considered the standard treatments and prophylactic agents for infections caused by herpesviral strains such as HSV (King, 1988; Field & Vere Hodge, 2013). Until a decade ago, the impact of acyclovir on the control of severe and life-threatening herpesvirus infections was unprecedented. HBV infections are treated with interferon α or one of five nucleos(t)ide analogs (Parker et al., 2004; Song et al., 2004; Lima et al., 2001). Interferon α leads to sustained clinical improvement in 20-30% of patients, but the infection is very rarely cleared (Hostomsky et al., 1993; Katayanagi et al., 1990; Braunshofer-Reiter et al., 1998). The nucleos(t)ide analogs are used more frequently than interferon. They inhibit DNA synthesis and suppress viral replication by 4-5 $\log_{10}$ in up to 70-90% patients, often to below the standard clinical detection limit of 300-400 copies/mL (Braunshofer-Reiter et al., 1998; Nowotny et al., 2005; Klumpp et al., 2003. However, treatment eradicates the infection as measured by loss of the viral surface antigen (HBsAg) from the serum in only 3-6% of patients even after years of therapy (Braunshofer-Reiter et al., 1998; Nowotny et al., 2005; Klumpp et al., 2003; Nowotny et al., 2006).

Unfortunately, these treatments are limited because the viruses have begun to develop resistance to these treatment options. For example, antiviral resistance was a major problem with the earlier anti-HBV nucleos(t)ide analogs, but resistance to the newer drugs entecavir and tenofovir is generally lower (Parker et al., 2004; Keck et al., 1998; Goedken et al., 2001; Li et al., 1995). Furthermore, while significantly reducing the viral load these drugs are often insufficient to completely eliminate HBV from the patient's body. HSV resistance to the nucleos(t)ide analogs has also begun to develop and is particularly a concern among immunosuppressed individuals, in whom resistant virus comprises up to 15.7% of HSV infections (Frobert et al., 2014). Nucleos(t)ide-resistant infections are also common among pediatric patients (Wang et al., 2011) and those with HSV infections of the eye (van Velzen et al., 2013; Duan et al., 2008). Furthermore, although these drugs can significantly reduce the load of wild-type HSV in patients during primary infection or reactivation, they are only partially effective (Vere Hodge & Field, 2013; Johnston et al., 2012).

Additionally, fungal infections, such as infections of *Cryptococcus neoformans*, are a growing problem amongst people who are immunocompromised. The *C. neoformans* is believed to cause up to 1 million infections each year particular in patients who are HIV positive and results in about 250,000 deaths annually (Rajasingham et. al., 2017). Fungal infections are also a major issue with patients who have undergone a major organ transplant. Estimates show that about 3% of transplant patients will experience an invasive fungal infection with an estimated mortality rate of 25% to 40% in the first year (Shoham and Marr, 2012). The leading treatment for *C. neoformans* fungal infection is amphotericin B and flucytosine. This treatment course is long, has substantial toxicity, and even in the most favorable conditions retains 15-30% mortality (Lortholary, 2007; Mdodo et. al., 2010; Bratton et. al., 2013). The most recently approved class of anti-fungal compounds, the echinocandins, do not inhibit *C. neoformans* at a clinically useful concentration. Given these significant handicaps to the current treatment options, there remains a need to develop new therapeutic options for these diseases.

Therefore, there remains a growing need to develop new compounds which utilize different mechanisms to treat and potentially cure these infections to use either alone or in combination with another front-line agent.

SUMMARY

Thus, in accordance with the present disclosure, there is provided compounds which may be useful for treating an infection of a microorganism.

In some aspects, the present disclosure provides compounds of the formula:

(I)

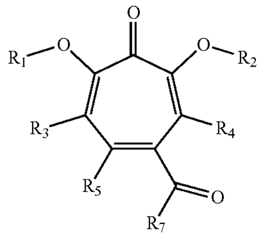

wherein:

$R_1$ and $R_2$ are each independently hydrogen, alkyl$_{(C\leq8)}$, substituted alkyl$_{(C\leq8)}$, acyl$_{(C\leq8)}$, or substituted acyl$_{(C\leq8)}$;

$R_3$ and $R_4$ are each independently hydrogen, halo, hydroxy, alkyl$_{(C\leq8)}$, substituted alkyl$_{(C\leq8)}$, aryl$_{(C\leq12)}$, or substituted aryl$_{(C\leq12)}$;

$R_5$ is hydrogen, alkyl$_{(C\leq8)}$, substituted alkyl$_{(C\leq8)}$, aryl$_{(C\leq12)}$, or substituted aryl$_{(C\leq12)}$; and $R_7$ is an amino acid residue, heterocycloalkyl$_{(C\leq12)}$, substituted heterocycloalkyl$_{(C\leq12)}$, —N($R_8$)$R_9$, wherein:

$R_8$ is hydrogen, alkyl$_{(C\leq8)}$, substituted alkyl$_{(C\leq8)}$; and $R_9$ is alkyl$_{(C4-8)}$, substituted alkyl$_{(C4-8)}$, alkynyl$_{(C\leq12)}$, aryl$_{(C\leq12)}$, aralkyl$_{(C\leq18)}$, heteroaryl$_{(C\leq12)}$, heteroaralkyl$_{(C\leq18)}$, or a substituted version thereof; or —$Y_1$—$R_a$, wherein:

$Y_1$ is alkanediyl$_{(C\leq12)}$, arenediyl$_{(C\leq12)}$, or a substituted version of either group;

$R_a$ is aralkyl$_{(C\leq12)}$, heterocycloalkyl$_{(C\leq12)}$, aralkoxy$_{(C\leq12)}$, -aralkyl$_{(C\leq12)}$-heterocycloalkyl$_{(C\leq8)}$, or a substituted version thereof; or a group of the formula:

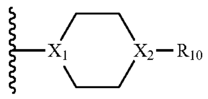

wherein:

$X_1$ and $X_2$ is C or N;

$R_{10}$ is alkyl$_{(C\leq12)}$, cycloalkyl$_{(C\leq12)}$, aryl$_{(C\leq12)}$, heteroaryl$_{(C\leq12)}$, aralkyl$_{(C\leq18)}$, acyl$_{(C\leq12)}$, heteroarenediyl$_{(C\leq12)}$-heteroaryl$_{(C\leq12)}$, —C(O)-diarylamino$_{(C\leq12)}$, —C(O)-heteroaryl$_{(C\leq12)}$, alkylsulfonyl$_{(C\leq12)}$, arylsulfonyl$_{(C\leq12)}$, heteroarylsulfonyl$_{(C\leq12)}$, alkylsulfonylamino$_{(C\leq12)}$, or a substituted version of any of these groups; an amino protecting group; or a compound of the formula:

(II)

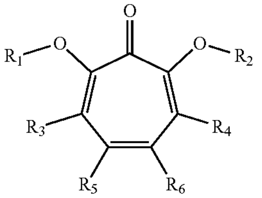

wherein:

$R_1$ and $R_2$ are each independently hydrogen, alkyl$_{(C\leq8)}$, substituted alkyl$_{(C\leq8)}$, acyl$_{(C\leq8)}$, or substituted acyl$_{(C\leq8)}$;

$R_3$ is —S(O)$_x$$R_b$, wherein:

x is 0, 1, or 2;

$R_b$ is hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups;

$R_4$ is hydrogen, alkyl$_{(C\leq8)}$, substituted alkyl$_{(C\leq8)}$, —S(O)$_y$$R_c$, wherein:

y is 0, 1, or 2;

$R_c$ is hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups; and $R_5$ and $R_6$ are each independently hydrogen, alkyl$_{(C\leq8)}$, substituted alkyl$_{(C\leq8)}$, aryl$_{(C\leq12)}$, substituted aryl$_{(C\leq12)}$, acyl$_{(C\leq8)}$, or substituted acyl$_{(C\leq8)}$;

or a pharmaceutically acceptable salt thereof.

In some embodiments, the compound is further defined as:

(I)

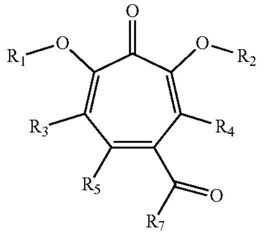

wherein:

$R_1$ and $R_2$ are each independently hydrogen, alkyl$_{(C\leq8)}$, substituted alkyl$_{(C\leq8)}$, acyl$_{(C\leq8)}$, or substituted acyl$_{(C\leq8)}$;

$R_3$ and $R_4$ are each independently hydrogen, halo, hydroxy, alkyl$_{(C\leq8)}$, substituted alkyl$_{(C\leq8)}$, aryl$_{(C\leq12)}$, or substituted aryl$_{(C\leq12)}$;

$R_5$ is hydrogen, alkyl$_{(C\leq8)}$, substituted alkyl$_{(C\leq8)}$, aryl$_{(C\leq12)}$, or substituted aryl$_{(C\leq12)}$; and $R_7$ is an amino acid residue, heterocycloalkyl$_{(C\leq12)}$, substituted heterocycloalkyl$_{(C\leq12)}$, —N($R_8$)$R_9$, wherein:

$R_8$ is hydrogen, alkyl$_{(C\leq8)}$, substituted alkyl$_{(C\leq8)}$; and $R_9$ is alkynyl$_{(C\leq12)}$, aryl$_{(C\leq12)}$, aralkyl$_{(C\leq18)}$, heteroaryl$_{(C\leq12)}$, heteroaralkyl$_{(C\leq18)}$, or a substituted version thereof; or —$Y_1$—$R_a$, wherein:

$Y_1$ is alkanediyl$_{(C\leq12)}$, arenediyl$_{(C\leq12)}$, or a substituted version of either group;

$R_a$ is aralkyl$_{(C\leq12)}$, heterocycloalkyl$_{(C\leq12)}$, aralkoxy$_{(C\leq12)}$, or a substituted version thereof; or a group of the formula:

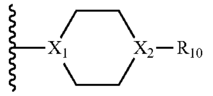

wherein:

$X_1$ and $X_2$ is C or N;

$R_{10}$ is cycloalkyl$_{(C\le12)}$, acyl$_{(C\le12)}$, heteroarenediyl$_{(C\le12)}$-heteroaryl$_{(C\le12)}$, —C(O)-heteroaryl$_{(C\le12)}$, alkylsulfonyl$_{(C\le12)}$, alkylsulfonylamino$_{(C\le12)}$, or a substituted version of any of these groups; an amino protecting group; or compounds of the formula:

(II)

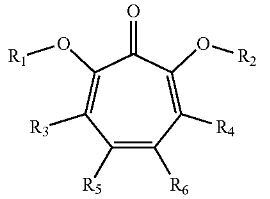

wherein:

$R_1$ and $R_2$ are each independently hydrogen, alkyl$_{(C\le8)}$, substituted alkyl$_{(C\le8)}$, acyl$_{(C\le8)}$, or substituted acyl$_{(C\le8)}$;

$R_3$ is —S(O)$_x$R$_b$, wherein:

x is 0, 1, or 2;

$R_b$ is hydrogen or alkyl$_{(C\le12)}$, aryl$_{(C\le12)}$, aralkyl$_{(C\le12)}$, heteroaryl$_{(C\le12)}$, heteroaralkyl$_{(C\le12)}$, or a substituted version of any of these groups;

$R_4$ is hydrogen, alkyl$_{(C\le8)}$, substituted alkyl$_{(C\le8)}$, —S(O)$_y$R$_c$, wherein:

y is 0, 1, or 2;

$R_c$ is hydrogen or alkyl$_{(C\le12)}$, aryl$_{(C\le12)}$, aralkyl$_{(C\le12)}$, heteroaryl$_{(C\le12)}$, heteroaralkyl$_{(C\le12)}$, or a substituted version of any of these groups; and $R_5$ and $R_6$ are each independently hydrogen, alkyl$_{(C\le8)}$, substituted alkyl$_{(C\le8)}$, aryl$_{(C\le12)}$, substituted aryl$_{(C\le12)}$, acyl$_{(C\le8)}$, or substituted acyl$_{(C\le8)}$;

or a pharmaceutically acceptable salt thereof.

In some embodiments, the compounds are further defined as:

(I)

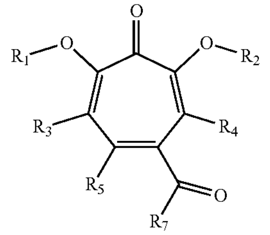

wherein:

$R_1$ and $R_2$ are each independently hydrogen, alkyl$_{(C\le8)}$, substituted alkyl$_{(C\le8)}$, acyl$_{(C\le8)}$, or substituted acyl$_{(C\le8)}$;

$R_3$ and $R_4$ are each independently hydrogen, halo, hydroxy, alkyl$_{(C\le8)}$, substituted alkyl$_{(C\le8)}$, aryl$_{(C\le12)}$, or substituted aryl$_{(C\le12)}$;

$R_5$ is hydrogen, alkyl$_{(C\le8)}$, substituted alkyl$_{(C\le8)}$, aryl$_{(C\le12)}$, or substituted aryl$_{(C\le12)}$; and $R_7$ is an amino acid residue, heterocycloalkyl$_{(C\le12)}$, substituted heterocycloalkyl$_{(C\le12)}$, —N(R$_8$)R$_9$, wherein:

$R_8$ is hydrogen, alkyl$_{(C\le8)}$, substituted alkyl$_{(C\le8)}$; and $R_9$ is alkyl$_{(C4-8)}$, substituted alkyl$_{(C4-8)}$, alkynyl$_{(C\le12)}$, aryl$_{(C\le12)}$, aralkyl$_{(C\le18)}$, heteroaryl$_{(C\le12)}$, heteroaralkyl$_{(C\le18)}$, or a substituted version thereof; or —Y$_1$—R$_a$, wherein:

$Y_1$ is alkanediyl$_{(C\le12)}$, arenediyl$_{(C\le12)}$, or a substituted version of either group;

$R_a$ is aralkyl$_{(C\le12)}$, heteroaryl$_{(C\le12)}$, heterocycloalkyl$_{(C\le12)}$, aralkoxy$_{(C\le12)}$, -aralkyl$_{(C\le12)}$-heterocycloalkyl$_{(C\le8)}$, or a substituted version thereof; or a group of the formula:

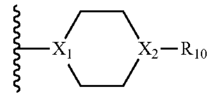

wherein:

$X_1$ and $X_2$ is C or N;

$R_{10}$ is cycloalkyl$_{(C\le12)}$, aryl$_{(C\le12)}$, heteroaryl$_{(C\le12)}$, aralkyl$_{(C\le18)}$, acyl$_{(C\le12)}$, heteroarenediyl$_{(C\le12)}$-heteroaryl$_{(C\le12)}$, —C(O)-diarylamino$_{(C\le12)}$, —C(O)-heteroaryl$_{(C\le12)}$, alkylsulfonyl$_{(C\le12)}$, heterocycloalkylsulfonyl$_{(C\le12)}$, alkylsulfonylamino$_{(C\le12)}$, or a substituted version of any of these groups; an amino protecting group; or or a pharmaceutically acceptable salt thereof.

In some embodiments, the compounds are further defined as:

(III)

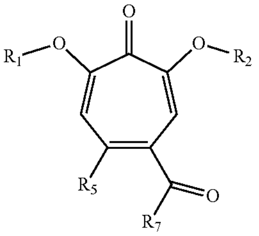

wherein:

$R_1$ and $R_2$ are each independently hydrogen, alkyl$_{(C\le8)}$, substituted alkyl$_{(C\le8)}$, acyl$_{(C\le8)}$, or substituted acyl$_{(C\le8)}$;

$R_5$ is hydrogen, alkyl$_{(C\le8)}$, substituted alkyl$_{(C\le8)}$, aryl$_{(C\le12)}$, or substituted aryl$_{(C\le12)}$; and $R_7$ is an amino acid residue, heterocycloalkyl$_{(C\le12)}$, substituted heterocycloalkyl$_{(C\le12)}$, —N(R$_8$)R$_9$, wherein:

$R_8$ is hydrogen, alkyl$_{(C\le8)}$, substituted alkyl$_{(C\le8)}$; and $R_9$ is alkyl$_{(C4-8)}$, substituted alkyl$_{(C4-8)}$, alkynyl$_{(C\le12)}$, aryl$_{(C\le12)}$, aralkyl$_{(C\le18)}$, heteroaryl$_{(C\le12)}$, heteroaralkyl$_{(C\le18)}$, or a substituted version thereof; or —Y$_1$—R$_a$, wherein:

$Y_1$ is alkanediyl$_{(C\leq12)}$, arenediyl$_{(C\leq12)}$, or a substituted version of either group;

$R_a$ is aralkyl$_{(C\leq12)}$, heteroaryl$_{(C\leq12)}$, heterocycloalkyl$_{(C\leq12)}$, -aralkyl$_{(C\leq12)}$-heterocy cloalkyl$_{(C\leq8)}$, aralkoxy$_{(C\leq12)}$, or a substituted version thereof; or a group of the formula:

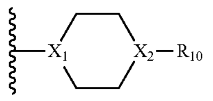

wherein:

$X_1$ and $X_2$ is C or N;

$R_{10}$ is cycloalkyl$_{(C\leq12)}$, aryl$_{(C\leq12)}$, heteroaryl$_{(C\leq12)}$, aralkyl$_{(C\leq18)}$, acyl$_{(C\leq12)}$, heteroarenediyl$_{(C\leq12)}$-heteroaryl$_{(C\leq12)}$, —C(O)-diarylamino$_{(C\leq12)}$, —C(O)-heteroaryl$_{(C\leq12)}$, alkylsulfonyl$_{(C\leq12)}$, heterocycloalkylsulfonyl$_{(C\leq12)}$, alkylsulfonylamino$_{(C\leq12)}$, or a substituted version of any of these groups; an amino protecting group; or or a pharmaceutically acceptable salt thereof.

In some embodiments, the compounds are further defined as:

(IV)

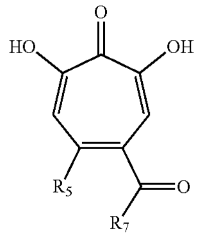

wherein:

$R_5$ is hydrogen, alkyl$_{(C\leq8)}$, substituted alkyl$_{(C\leq8)}$, aryl$_{(C\leq12)}$, or substituted aryl$_{(C\leq12)}$; and $R_7$ is an amino acid residue, heterocycloalkyl$_{(C\leq12)}$, substituted heterocycloalkyl$_{(C\leq12)}$, —$N(R_8)R_9$, wherein:

$R_8$ is hydrogen, alkyl$_{(C\leq8)}$, substituted alkyl$_{(C\leq8)}$; and $R_9$ is alkyl$_{(C4-8)}$, substituted alkyl$_{(C4-8)}$, alkynyl$_{(C\leq12)}$, aryl$_{(C\leq12)}$, aralkyl$_{(C\leq18)}$, heteroaryl$_{(C\leq12)}$, heteroaralkyl$_{(C\leq18)}$, or a substituted version thereof; or —$Y_1$—$R_a$, wherein:

$Y_1$ is alkanediyl$_{(C\leq12)}$, arenediyl$_{(C\leq12)}$, or a substituted version of either group;

$R_a$ is aralkyl$_{(C\leq12)}$, heteroaryl$_{(C\leq12)}$, heterocycloalkyl$_{(C\leq12)}$, aralkoxy$_{(C\leq12)}$, -aralkyl$_{(C\leq12)}$-heterocycloalkyl$_{(C\leq8)}$, or a substituted version thereof; or a group of the formula:

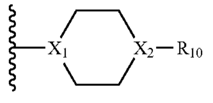

wherein:

$X_1$ and $X_2$ is C or N;

$R_{10}$ is cycloalkyl$_{(C\leq12)}$, aryl$_{(C\leq12)}$, heteroaryl$_{(C\leq12)}$, aralkyl$_{(C\leq18)}$, acyl$_{(C\leq12)}$, heteroarenediyl$_{(C\leq12)}$-heteroaryl$_{(C\leq12)}$, —C(O)-diarylamino$_{(C\leq12)}$, —C(O)-heteroaryl$_{(C\leq12)}$, alkylsulfonyl$_{(C\leq12)}$, heterocycloalkyl sulfonyl$_{(C\leq12)}$, alkylsulfonylamino$_{(C\leq12)}$, or a substituted version of any of these groups; an amino protecting group;

or a pharmaceutically acceptable salt thereof.

In other embodiments, the compounds are further defined as:

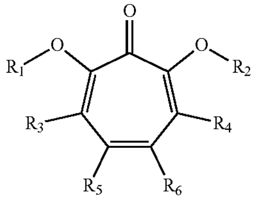

wherein:

$R_1$ and $R_2$ are each independently hydrogen, alkyl$_{(C\leq8)}$, substituted alkyl$_{(C\leq8)}$, acyl$_{(C\leq8)}$, or substituted acyl$_{(C\leq8)}$;

$R_3$ is —$S(O)_xR_b$, wherein:

x is 0, 1, or 2;

$R_b$ is hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups;

$R_4$ is hydrogen, alkyl$_{(C\leq8)}$, substituted alkyl$_{(C\leq8)}$, —$S(O)_yR_c$, wherein:

y is 0, 1, or 2;

$R_c$ is hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups; and $R_5$ and $R_6$ are each independently hydrogen, alkyl$_{(C\leq8)}$, substituted alkyl$_{(C\leq8)}$, aryl$_{(C\leq12)}$, substituted aryl$_{(C\leq12)}$, acyl$_{(C\leq8)}$, or substituted acyl$_{(C\leq8)}$;

or a pharmaceutically acceptable salt thereof.

In some embodiments, the compounds are further defined as:

(V)

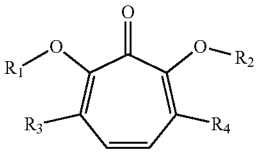

wherein:

$R_1$ and $R_2$ are each independently hydrogen, alkyl$_{(C\leq8)}$, substituted alkyl$_{(C\leq8)}$, acyl$_{(C\leq8)}$, or substituted acyl$_{(C\leq8)}$;

$R_3$ is —$S(O)_xR_b$, wherein:

x is 0, 1, or 2;

$R_b$ is hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups;

$R_4$ is hydrogen, alkyl$_{(C\leq8)}$, substituted alkyl$_{(C\leq8)}$, —$S(O)_yR_c$, wherein:

y is 0, 1, or 2;

$R_c$ is hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups; and or a pharmaceutically acceptable salt thereof.

In some embodiments, the compounds are further defined as:

(VI)

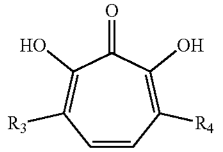

wherein:

$R_3$ is —$S(O)_xR_b$, wherein:

x is 0, 1, or 2;

$R_b$ is hydrogen or alkyl$_{(C\le 12)}$, aryl$_{(C\le 12)}$, aralkyl$_{(C\le 12)}$, heteroaryl$_{(C\le 12)}$, heteroaralkyl$_{(C\le 12)}$, or a substituted version of any of these groups;

$R_4$ is hydrogen, alkyl$_{(C\le 8)}$, substituted alkyl$_{(C\le 8)}$, —$S(O)_yR_c$, wherein:

y is 0, 1, or 2;

$R_c$ is hydrogen or alkyl$_{(C\le 12)}$, aryl$_{(C\le 12)}$, aralkyl$_{(C\le 12)}$, heteroaryl$_{(C\le 12)}$, heteroaralkyl$_{(C\le 12)}$, or a substituted version of any of these groups; and or a pharmaceutically acceptable salt thereof.

In some embodiments, $R_1$ is hydrogen. In some embodiments, $R_2$ is hydrogen.

In some embodiments, $R_3$ is hydrogen. In other embodiments, $R_3$ is —$S(O)_xR_b$, wherein: x is 0 or 2; and $R_b$ is hydrogen or alkyl$_{(C\le 12)}$, aryl$_{(C\le 12)}$, aralkyl$_{(C\le 12)}$, heteroaryl$_{(C\le 12)}$, heteroaralkyl$_{(C\le 12)}$, or a substituted version of any of these groups. In some embodiments, x is 0. In other embodiments, x is 2. In some embodiments, $R_b$ is alkyl$_{(C\le 12)}$ or substituted alkyl$_{(C\le 12)}$. In some embodiments, $R_b$ is alkyl$_{(C\le 12)}$ such as isopropyl, butyl, or hexyl. In other embodiments, $R_b$ is aryl$_{(C\le 12)}$ or substituted aryl$_{(C\le 12)}$. In some embodiments, $R_b$ is aryl$_{(C\le 12)}$ such as phenyl, 4-methylphenyl, or napthyl. In other embodiments, $R_b$ is aralkyl$_{(C\le 12)}$ or substituted aralkyl$_{(C\le 12)}$. In some embodiments, $R_b$ is aralkyl$_{(C\le 12)}$ such as benzyl or 2-phenylethyl.

In some embodiments, $R_4$ is hydrogen. In other embodiments, $R_4$ is —$S(O)_xR_b$, wherein: x is 0 or 2; and $R_b$ is hydrogen or alkyl$_{(C\le 12)}$, aryl$_{(C\le 12)}$, aralkyl$_{(C\le 12)}$, heteroaryl$_{(C\le 12)}$, heteroaralkyl$_{(C\le 12)}$, or a substituted version of any of these groups. In some embodiments, x is 0. In other embodiments, x is 2. In some embodiments, $R_b$ is alkyl$_{(C\le 12)}$ or substituted alkyl$_{(C\le 12)}$. In some embodiments, $R_b$ is alkyl$_{(C\le 12)}$ such as isopropyl, butyl, or hexyl. In other embodiments, $R_b$ is aryl$_{(C\le 12)}$ or substituted aryl$_{(C\le 12)}$. In some embodiments, $R_b$ is aryl$_{(C\le 12)}$ such as phenyl, 4-methylphenyl, or napthyl. In other embodiments, $R_b$ is aralkyl$_{(C\le 12)}$ or substituted aralkyl$_{(C\le 12)}$. In some embodiments, $R_b$ is aralkyl$_{(C\le 12)}$ such as benzyl or 2-phenylethyl.

In some embodiments, $R_5$ is hydrogen. In other embodiments, $R_5$ is alkyl$_{(C\le 8)}$ or substituted alkyl$_{(C\le 8)}$. In some embodiments, $R_5$ is alkyl$_{(C\le 8)}$ such as methyl. In some embodiments, $R_6$ is hydrogen.

In some embodiments, $R_7$ is an amino acid residue. In some embodiments, $R_7$ is valine residue, leucine residue, phenylalanine residue, methionine residue, lysine residue, tryptophan residue, and glutamic acid residue. In other embodiments, the amino acid residue is protected amino acid residue such as a protected valine residue, protected leucine residue, protected phenylalanine residue, protected methionine residue, protected lysine residue, protected tryptophan residue, and protected glutamic acid residue.

In other embodiments, $R_7$ is heterocycloalkyl$_{(C\le 12)}$ or substituted heterocycloalkyl$_{(C\le 12)}$. In some embodiments, $R_7$ is heterocycloalkyl$_{(C\le 12)}$ such as isothiazolidinyl or 1,1-dioxide thiazolidinyl.

In other embodiments, $R_7$ is —$N(R_8)R_9$. In some embodiments, $R_8$ is hydrogen. In other embodiments, $R_9$ is aryl$_{(C\le 12)}$ or substituted aryl$_{(C\le 12)}$. In some embodiments, $R_9$ is aryl$_{(C\le 12)}$ such as phenyl. In other embodiments, $R_9$ is substituted aryl$_{(C\le 12}$ such as 2,4-difluorophenyl. In other embodiments, $R_9$ is heteroaryl$_{(C\le 12)}$ or substituted heteroaryl$_{(C\le 12)}$. In some embodiments, $R_9$ is substituted heteroaryl$_{(C\le 12)}$ such as 4-fluoropyridinyl. In other embodiments, $R_9$ is alkynyl$_{(C\le 12)}$ or substituted alkynyl$_{(C\le 12)}$. In some embodiments, $R_9$ is substituted alkynyl$_{(C\le 12)}$ such as 3-diazoheptyn-6-yl. In other embodiments, $R_9$ is heteroaralkyl$_{(C\le 18)}$ or substituted heteroaralkyl$_{(C\le 18)}$. In some embodiments, $R_9$ is heteroaralkyl$_{(C\le 18)}$ such as thiophenylmethyl. In other embodiments, $R_9$ is aralkyl$_{(C\le 18)}$ or substituted aralkyl$_{(C\le 18)}$. In some embodiments, $R_9$ is aralkyl$_{(C\le 18)}$ such as biphenylmethyl, 2-phenylethyl or 3-phenylpropyl. In other embodiments, $R_9$ is substituted aralkyl$_{(C\le 18)}$ such as 4-methoxybenzyl or 4-trifluoromethoxyphenyl. In other embodiments, $R_9$ is alkyl$_{(C4\text{-}8)}$ or substituted alkyl$_{(C4\text{-}8)}$. In some embodiments, $R_9$ is alkyl$_{(C4\text{-}8)}$ such as butyl.

In other embodiments, $R_9$ is —$Y_1$—$R_a$. In some embodiments, $Y_1$ is alkanediyl$_{(C\le 12)}$ or substituted alkanediyl$_{(C\le 12)}$. In some embodiments, $Y_1$ is alkanediyl$_{(C\le 12)}$ such as methylene, ethylene, or propylene. In other embodiments, $Y_1$ is arenediyl$_{(C\le 12)}$ or substituted arenediyl$_{(C\le 12)}$. In some embodiments, $Y_1$ is arenediyl$_{(C\le 12)}$ such as benzendiyl. In some embodiments, $R_a$ is heterocycloalkyl$_{(C\le 12)}$ or substituted heterocycloalkyl$_{(C\le 12)}$. In some embodiments, $R_a$ is heterocycloalkyl$_{(C\le 12)}$ such as furanyl, pyrrolidinyl, or 2,2-dimethyldixoolanyl. In other embodiments, $R_a$ is substituted heterocycloalkyl$_{(C\le 12)}$ such as 2-Boc-piperidinyl or 4-Boc-piperidinyl. In other embodiments, $R_a$ is aralkyl$_{(C\le 12)}$ or substituted aralkyl$_{(C\le 12)}$. In some embodiments, $R_a$ is aralkyl$_{(C\le 12)}$ such as benzyl. In other embodiments, $R_a$ is aralkoxy$_{(C\le 12)}$ or substituted aralkoxy$_{(C\le 12)}$. In some embodiments, $R_a$ is aralkoxy$_{(C\le 12)}$ such as benzyloxy.

In other embodiments, $R_7$ is:

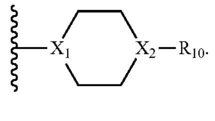

In some embodiments, $X_1$ is C. In other embodiments, $X_1$ is N. In some embodiments, $X_2$ is C. In other embodiments, $X_2$ is N.

In some embodiments, $R_{10}$ is hydrogen. In other embodiments, $R_{10}$ is cycloalkyl$_{(C\le 12)}$ or substituted cycloalkyl$_{(C\le 12)}$. In some embodiments, $R_{10}$ is cycloalkyl$_{(C\le 12)}$ such as cyclopropyl. In other embodiments, $R_{10}$ is aryl$_{(C\le 12)}$ or substituted aryl$_{(C\le 12)}$. In some embodiments, $R_{10}$ is substituted aryl$_{(C\le 12)}$ such as trifluoromethylphenyl or methoxyphenyl. In other embodiments, $R_{10}$ is heteroaryl$_{(C\le 12)}$ or substituted heteroaryl$_{(C\le 12)}$. In some embodiments, $R_{10}$ is heteroaryl$_{(C\le 12)}$ such as diazinyl. In other embodiments, $R_{10}$ is substituted heteroaryl$_{(C\le 12)}$ such as 7-nitrobenzooxadizol-4-yl or 4-cyano-2-furanyl-oxazolidinyl. In other embodiments, $R_{10}$ is aralkyl$_{(C\le 18)}$ or substituted aralkyl$_{(C\le 18)}$. In some embodiments, $R_{10}$ is substituted aralkyl$_{(C\le 18)}$ such as 2-fluoro-4-chlorobenzyl or di(4-fluorophenyl)methyl. In other embodiments, $R_{10}$ is —C(O)-diarylamino$_{(C\le 12)}$ or substituted —C(O)-diarylamino$_{(C\le 12)}$.

In some embodiments, $R_{10}$ is —C(O)-diarylamino$_{(C\leq 12)}$ such as —C(O)diphenylamino. In other embodiments, $R_{10}$ is alkylsulfonyl$_{(C\leq 12)}$ or substituted alkylsulfonyl$_{(C\leq 12)}$. In some embodiments, $R_{10}$ is alkylsulfonyl$_{(C\leq 12)}$ such as ethylsulfonyl. In other embodiments, $R_{10}$ is heteroaryl sulfonyl$_{(C\leq 12)}$ or substituted heteroarylsulfonyl$_{(C\leq 12)}$. In some embodiments, $R_{10}$ is heteroarylsulfonyl$_{(C\leq 12)}$ such as thiophenylsulfonyl. In other embodiments, $R_{10}$ is an amino protecting group. In some embodiments, $R_{10}$ is C1-C6 alkoxycarbonyl such as t-butyloxycarbonyl. In other embodiments, $R_{10}$ is acyl$_{(C\leq 12)}$ or substituted acyl$_{(C\leq 12)}$. In some embodiments, $R_{10}$ is acyl$_{(C\leq 12)}$ such as cyclohexoyl, napthalenoyl, furanoyl, or pyridinoyl. In other embodiments, $R_{10}$ is substituted acyl$_{(C\leq 12)}$ such as methoxybenzoyl or chlorobenzoyl.

In some embodiments, the compounds are further defined as:

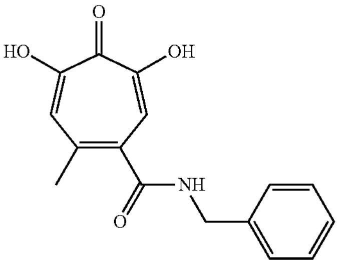
,

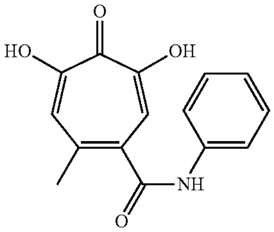
,

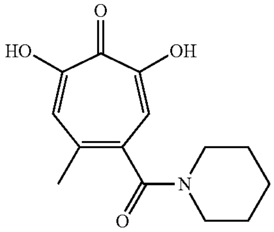
,

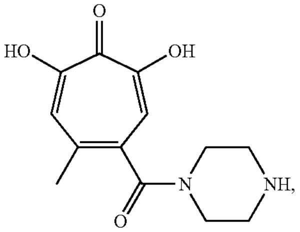

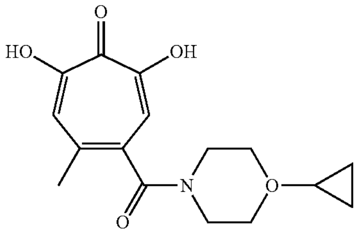
,

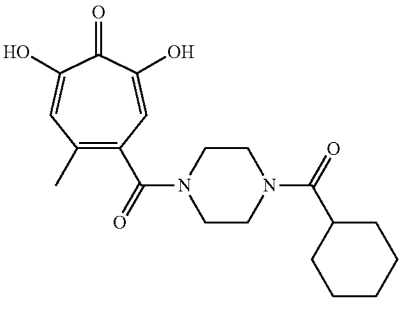
,

-continued

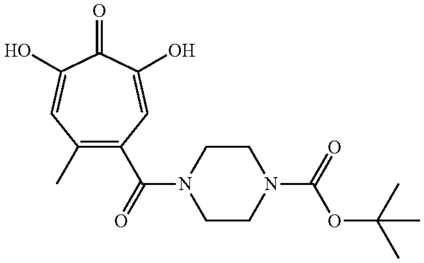
,

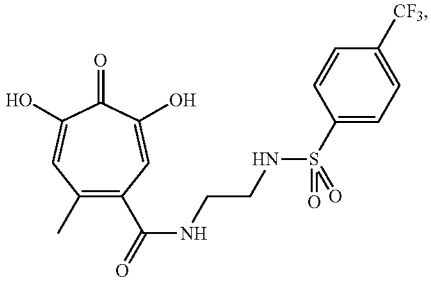

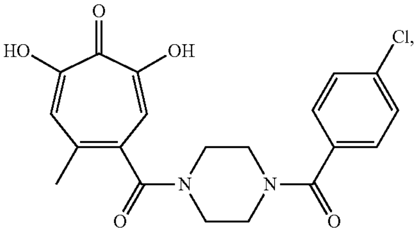

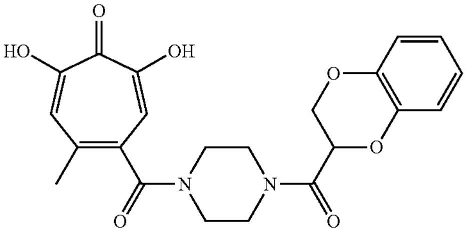
,

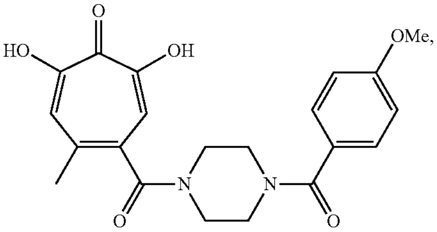

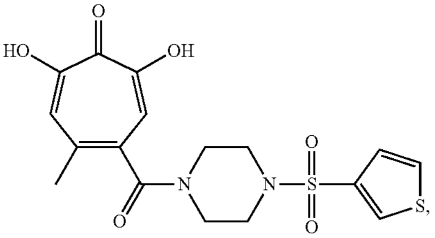

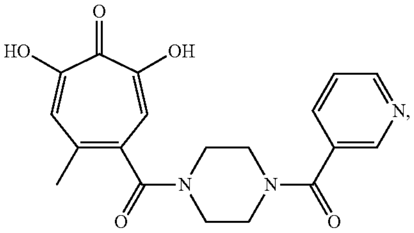

-continued
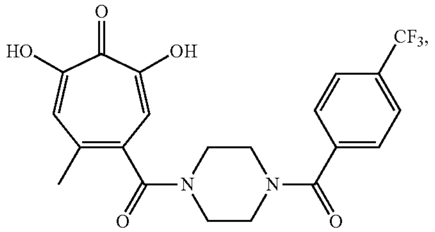
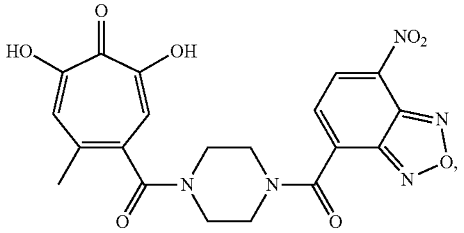
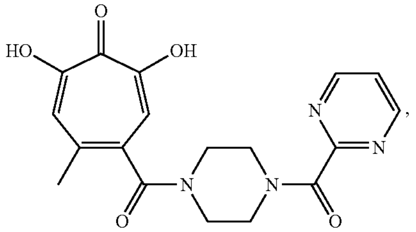
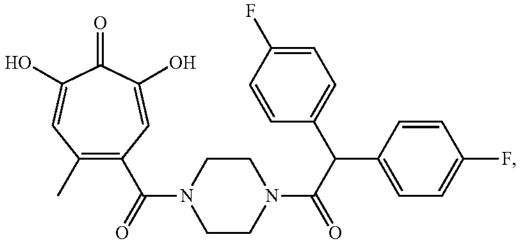
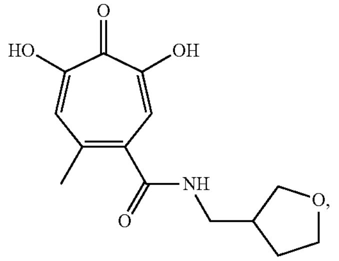
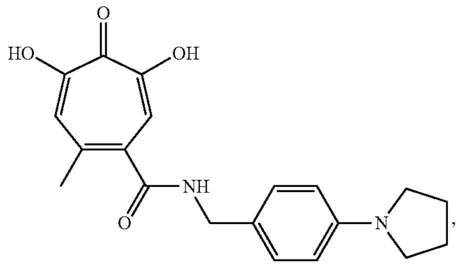
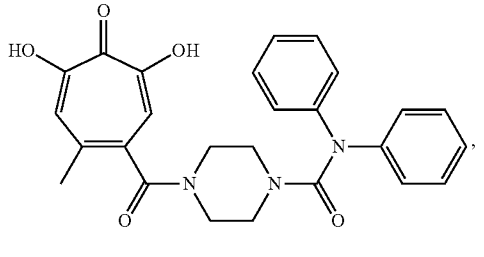
-continued
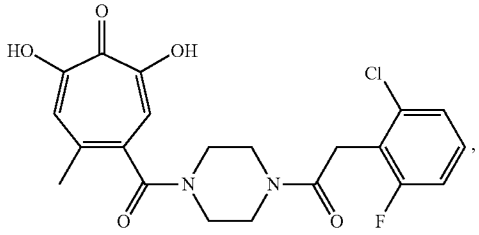
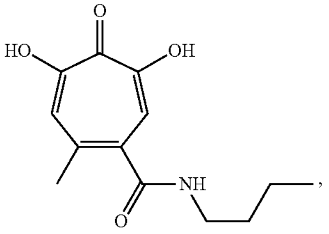
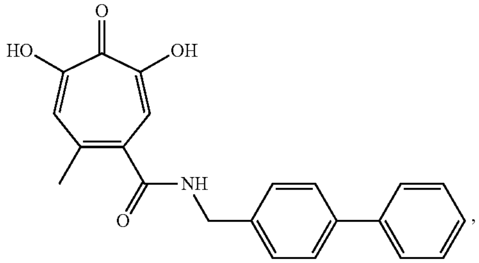
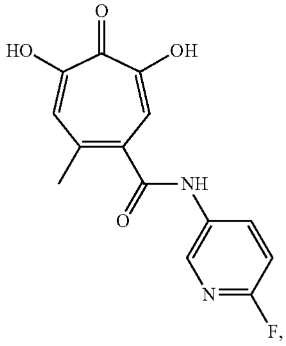
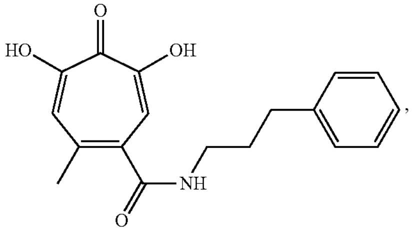
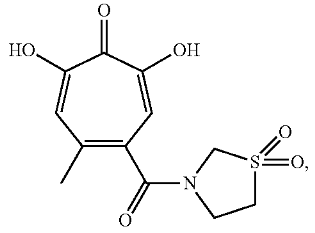

-continued
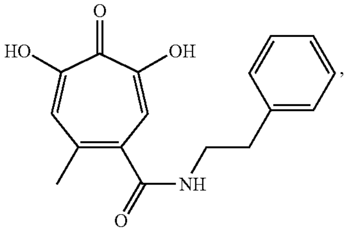
,
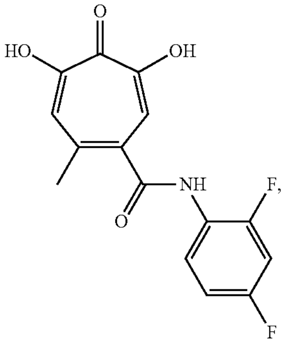
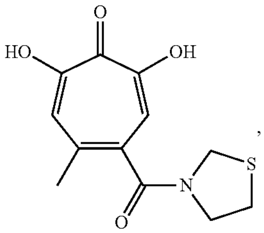
,
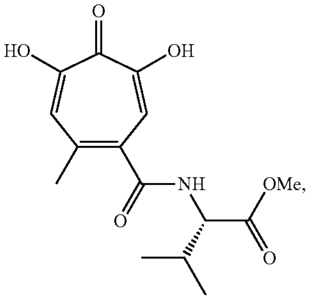
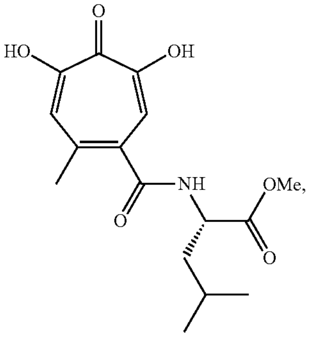
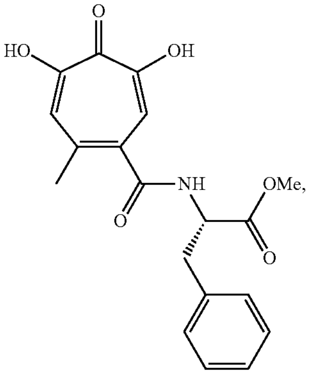
-continued
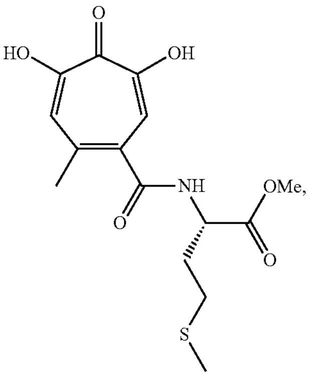
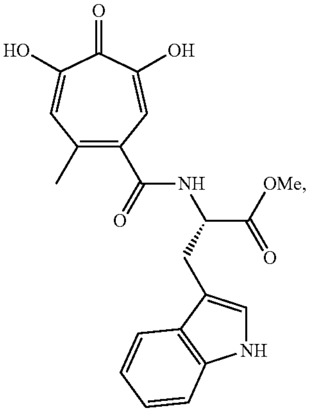
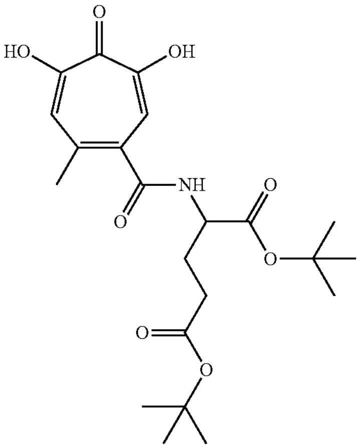
,
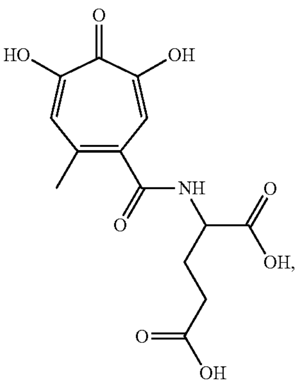

-continued
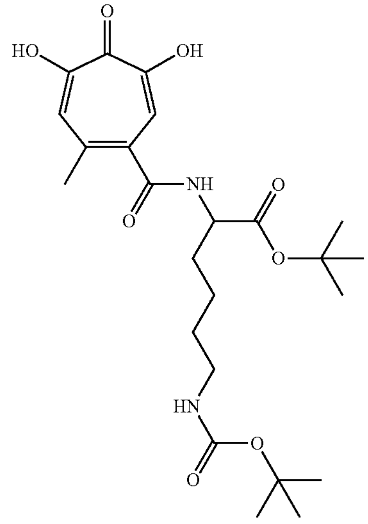
,
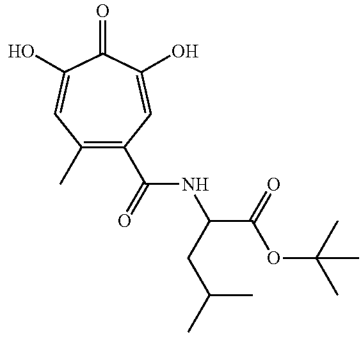
,
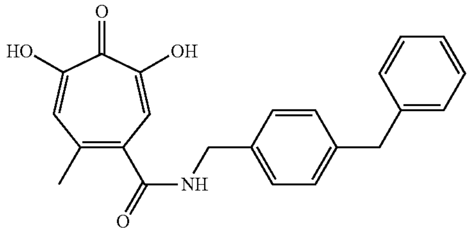
,
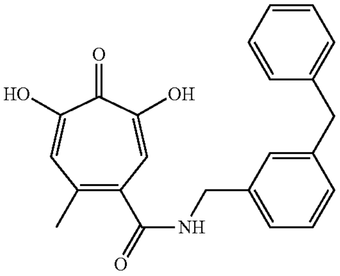
,
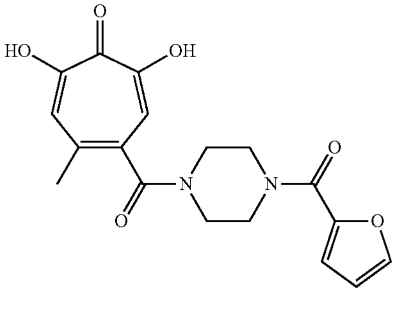
,
-continued
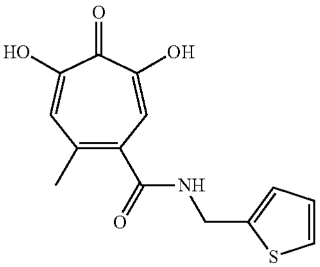
,
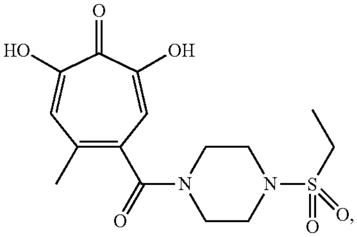
,
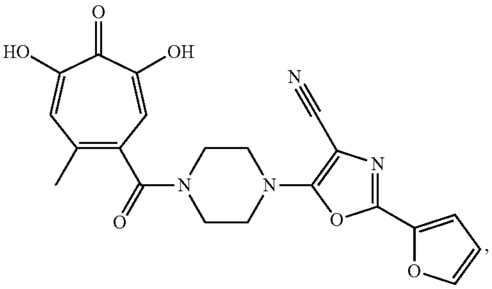
,
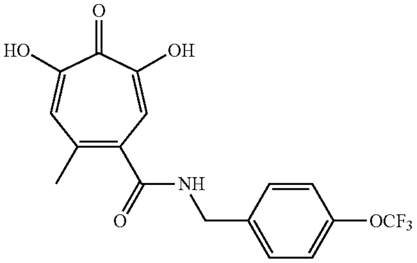
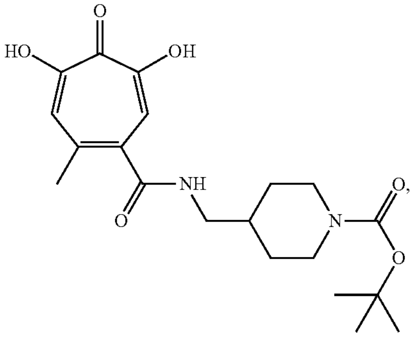
,
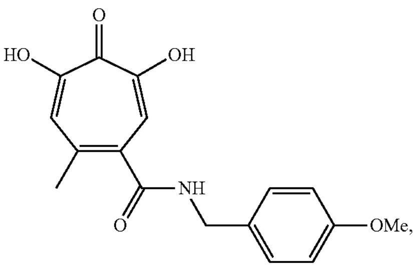
, -continued
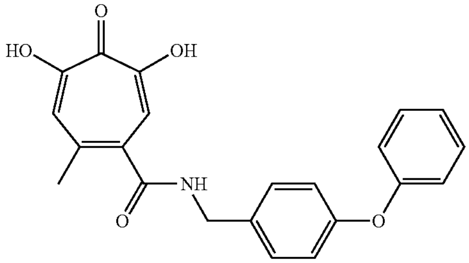
,
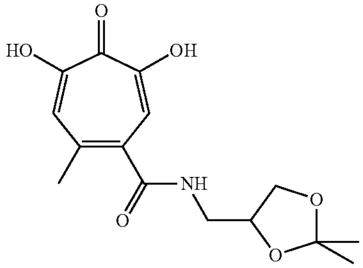
,
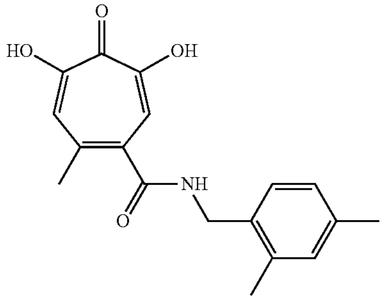
,
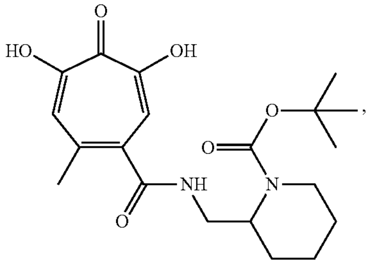
,
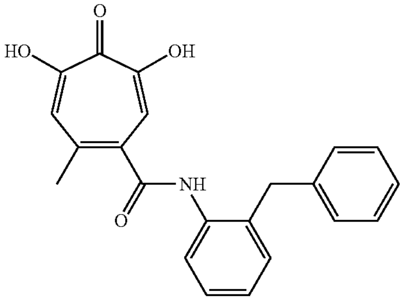
,
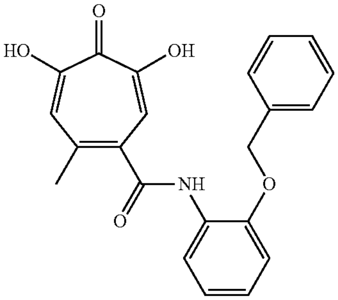
,
-continued
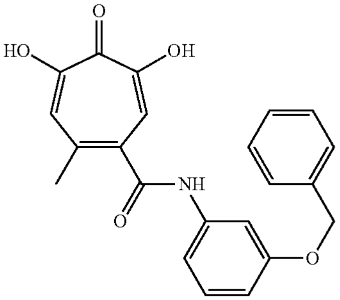
,
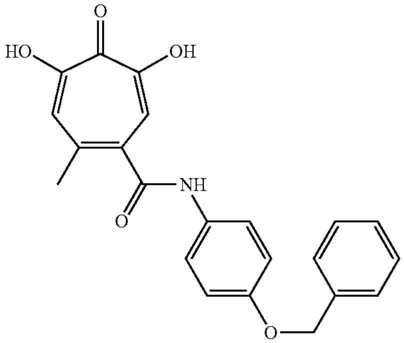
,
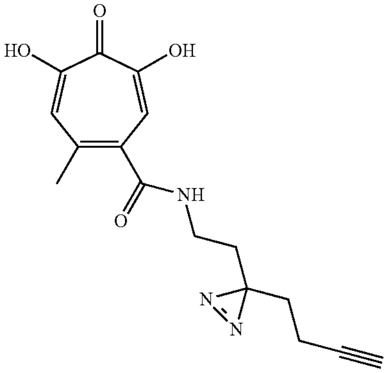
,
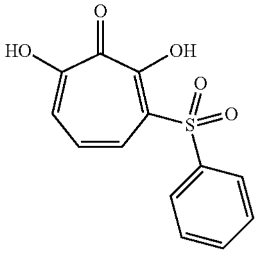
,
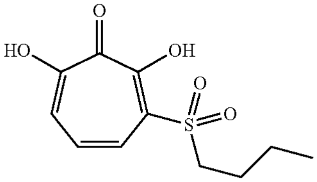
,
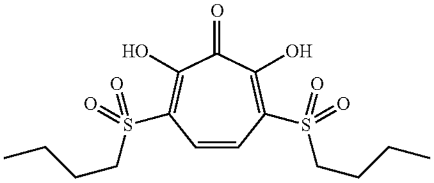
, -continued
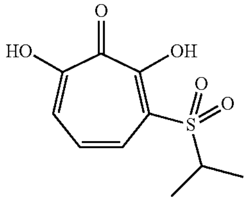
,
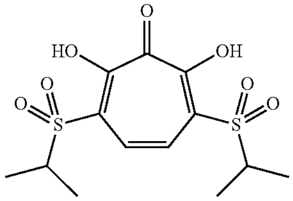
,
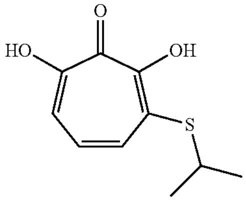
,
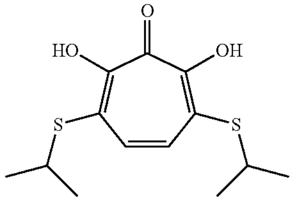
,
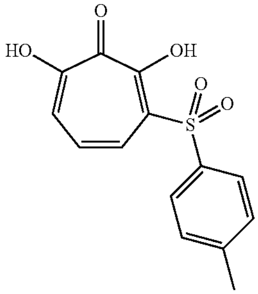
,
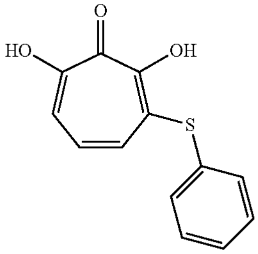
,
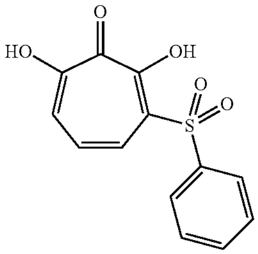
,
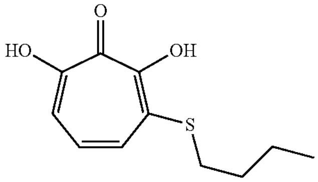
,
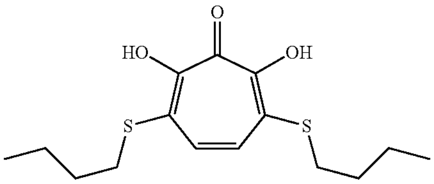
,
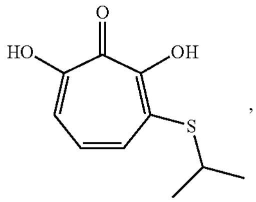
,
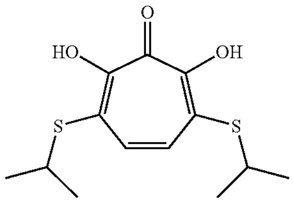
,
-continued
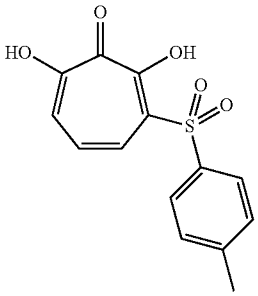
,
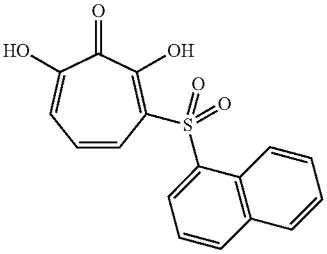
,
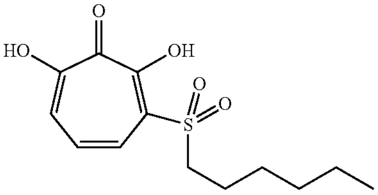
,
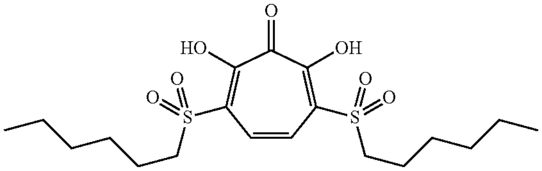
,
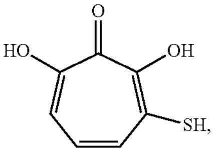
,
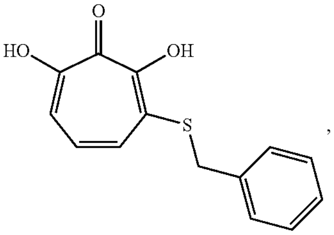
,
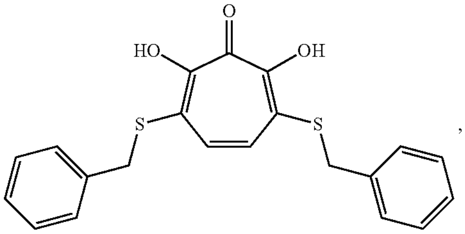
,
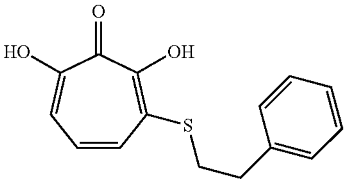
, -continued

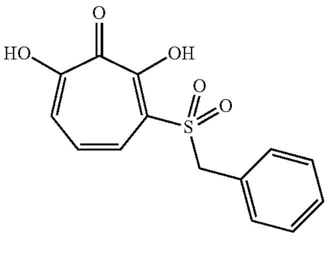
,

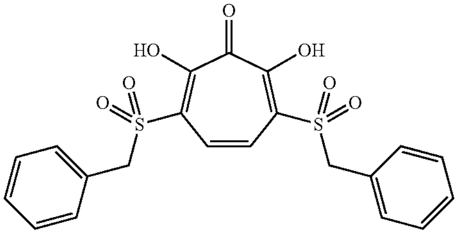
,

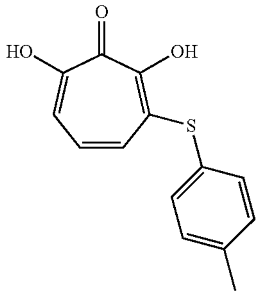
,

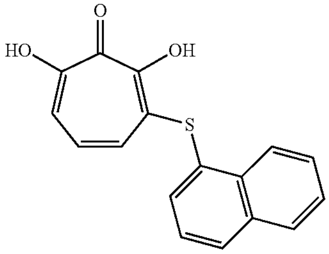
,

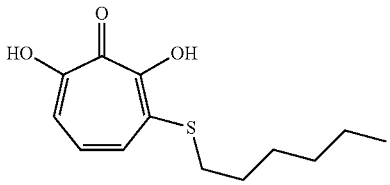
,

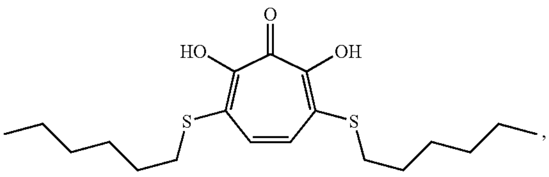
,

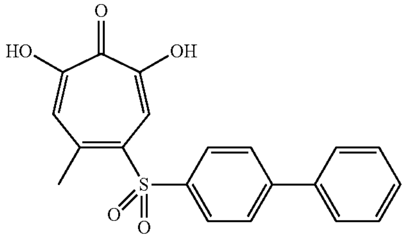
,

-continued

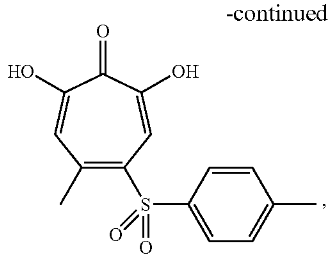
,

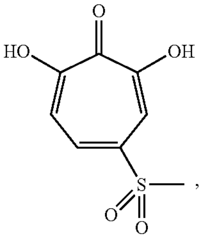
,

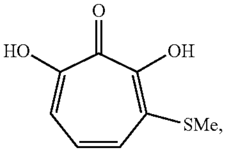
,

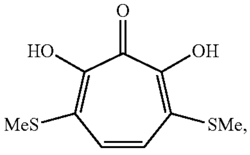
, or

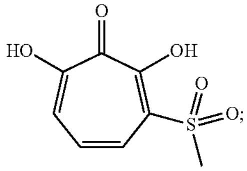
;

or a pharmaceutical salt thereof.

In other aspect, the present disclosure provides a compound of the formula:

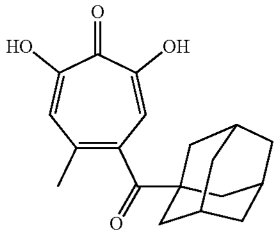 [SMILES: Cc1cc(O)c(=O)c(O)cc1C(=O)C12CC3CC(CC(C3)C1)C2]

or a pharmaceutical salt thereof.

In still another aspect, the present disclosure provides pharmaceutical compositions comprising:

(A) a compound described herein; and (B) an excipient.

In some embodiments, the compositions are formulated for administration: intravenously, intra-arterially, orally, buccally, nasally, ocularly, rectally, vaginally, topically, intramuscularly, intradermally, cutaneously or subcutaneously.

In still yet another aspect, the present disclosure provides methods of treating or preventing a disease or disorder comprising administering to a patient in need thereof a therapeutically effective amount of a compound or composition described herein. In some embodiments, the disease or disorder is an infection such as an infection of a microorganism. In some embodiments, the infection is a viral infection. In some embodiments, the viral infection is an infection of hepatitis B virus.

In some embodiments, the methods comprise a second hepatitis B virus treatment. In some embodiments, the second hepatitis B virus treatment is a nucleoside or nucleotide analog. In other embodiments, the second hepatitis B virus treatment is interferon alpha or pegylated interferon alpha. In other embodiments, the second hepatitis B virus treatment is lamivudine, adefovir, telbivudine, entecavir, or tenofovir.

In some embodiments, the method comprises administering the compound or composition a second time. In some embodiments, the second hepatitis B virus treatment is administered before the compound. In other embodiments, the second hepatitis B virus treatment is administered after the compound. In other embodiments, the second hepatitis B virus treatment is administered at the same time as the compound.

In some embodiments, the patient is a mammal infected with hepatitis B virus such as a human. In some embodiments, the patient has previously received a first-line hepatitis B virus therapy. In some embodiments, the hepatitis B virus has developed resistance to the first-line hepatitis B virus therapy. In some embodiments, the compound is administered intravenously, intraarterially, orally, or subcutaneously.

In other embodiments, the viral infection is an infection of a herpesvirus. In some embodiments, the compound is administered intravenously, intra-arterially, orally, buccally, nasally, ocularly, rectally, vaginally, topically, intramuscularly, intradermally, cutaneously, or subcutaneously. In some embodiments, the methods further comprise administered a second anti-herpesvirus therapy. In some embodiments, the second anti-herpesvirus therapy is foscarnet or a nucleoside analog. In some embodiments, the nucleoside analog is acyclovir, famciclovir, valaciclovir, penciclovir, or ganciclovir.

In some embodiments, the second anti-herpesvirus therapy is administered to the subject before or after the compound. In other embodiments, the second anti-herpesvirus therapy is administered to said subject at the same time as said compound. In some embodiments, the patient has previously received a first-line anti-herpesvirus therapy. In some embodiments, the herpesvirus has developed resistance to the first-line anti-herpesvirus therapy.

In some embodiments, the herpesvirus is selected from a human alpha herpesvirus, a human beta herpesvirus or a human gamma herpesvirus. In some embodiments, the human alpha herpesvirus is selected from herpes simplex virus 1 (HSV-1), herpes simplex virus 2 (HSV-2), and Varicella-Zoster virus (VZV). In some embodiments, the human beta herpesvirus is selected from human cytomegalovirus (HCMV), human herpesvirus 6A (HHV-6A), human herpesvirus 6B (HHV-6B), and human herpesvirus 7 (HHV-7). In some embodiments, the human gamma herpesvirus is selected from Epstein-Barr virus (EBV) and Kaposi's sarcoma herpesvirus (KSHV). In other embodiments, the herpesvirus is a non-human herpesvirus such as Marek's disease virus, equine herpesviruses, Bovine herpesviruses, or pseudorabies virus. In some embodiments, the methods comprise a second anti-viral compound.

In other embodiments, the disease or disorder is a fungal infection. In some embodiments, the fungal infection is an infection of a *Cryptococcus* fungus such as an infection of *Cryptococcus neoformans*. In some embodiments, the patient has a weakened immune system. In some embodiments, the patient has undergone an organ transplant. In some embodiments, the patient has human immunodeficiency virus. In some embodiments, the patient is taking a medicine which results in reduced immune activity such as a corticosteroid or a treatment for rheumatoid arthritis.

In some embodiments, the methods further comprise administering a second anti-fungal therapy. In some embodiments, the second anti-fungal therapy is a therapy targeting the ergosterol biosynthetic pathway. In some embodiments, the second anti-fungal therapy is Amphotericin B, fluconazole, itraconazole, posaconazole, or voriconazole. In some embodiments, the second anti-fungal therapy is voriconazole. In some embodiments, the second anti-fungal therapy is echinocandins or flucytosine.

In some embodiments, the fungal infection is in the central nervous system. In other embodiments, the fungal infection is in the lungs. In some embodiments, the fungal infection results in a disease. In some embodiments, the fungal infection results in cryptococcosis such as cryptococcal meningitis.

In some embodiments, the methods comprise administering the compound once. In other embodiments, the methods comprise administering the compound two or more times. In some embodiments, the compound is administered over a time period from 1 day to 2 years. In some embodiments, the time period is from about 1 week to about 8 weeks. In other embodiments, the time period is from about 6 months to about 12 months.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 1A. Homology model for the HBV RNaseH. The spheres represent Mn++ ions modeled into the active site. FIG. 1B. 390 (darker) and 404 (light) docked into the HBV RNaseH active site. FIG. 1C. 390 (light) and 120 (dark) docked into the active site. FIG. 1D. Alternative binding pose of 920. The active site Mn++ ions used during docking are shown as spheres near the upper left of panels FIGS. 1B-1D.

DETAILED DESCRIPTION

Figures 1A, 1B, 1C, 1D:
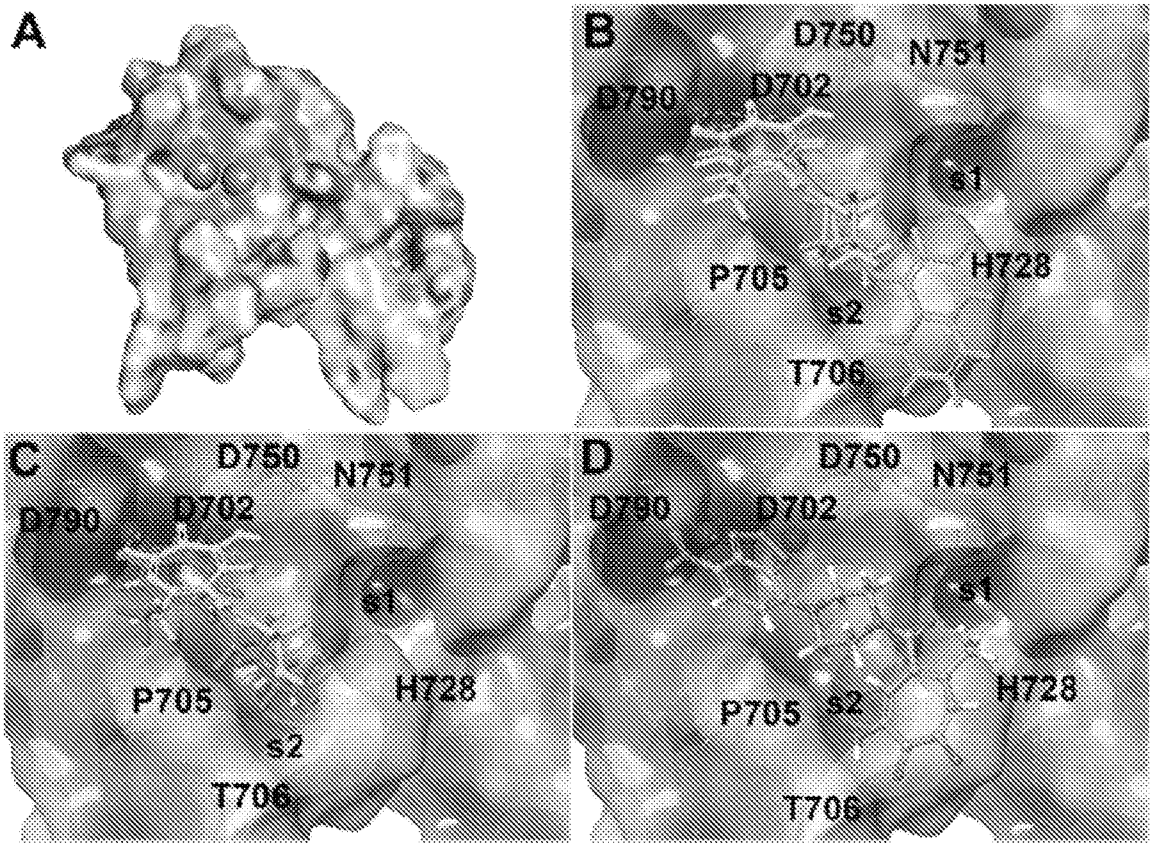
FIGS. 1A-1D show HBV RNaseH homology model and in silico docking of αHTs to the HBV RNaseH active site.

Herein are new sulfur and amide containing inhibitors of the nucleotidyl transferase superfamily of cellular enzymes. These compounds may be used in the treatment of an infection of microorganisms such as an infection of a fungus and infection of a virus such as one or more DNA based viruses. These DNA based viruses include both members of the herpesvirus and the hepatitis virus families. These compounds may possess one or more advantages based upon the known compounds including improved activity, greater pharmacokinetic activity, greater bioavailability, easier preparation or greater results when used with one or more secondary anti-microorganism therapies. The compounds, these uses, and additional evidence described in more detail below.

A. Nucleotidyl Transferase Superfamily Enzymes

The enzyme RNAse H, such as the HBV RNAse H, is a member of the nucleotidyl transferase superfamily (NTS)

whose members share a similar protein fold and enzymatic mechanisms (Yang 1995). Therefore, the presumed targets of the antiviral compounds are viral and/or cellular NTS enzymes. RNAse H enzymes (Hostomsky et al., 1993a; 1993b; 1993c) digest RNA when it is hybridized to DNA. Their physiological roles include removal of RNA primers during DNA synthesis, removal of abortive transcription products, and removal of RNA strands following reverse transcription by viruses or retrotransposons. Integrase enzymes cleave DNA strands and catalyze the covalent insertion of another DNA strand at the cleavage site. Consequently, the presumed mechanism of action for the inhibitors is through suppression of one or more of the nucleolytic or recombination-related activities essential for replication of the herpesvirus or hepatitis viral DNA.

The NTS family of enzymes includes *E. coli* RNase H I and II (Katayanagi et al., 1990, Yang et al., 1990 and Lai et al., 2000); human RNase H 1 and 2 (Lima et al., 2001, Frank et al., 1998 and Frank et al., 1998); the RuvC Holiday junction resolvase (Ariyoshi et al., 1994); and the Argonaute RNAse (Parker et al., 2004 and Song et al., 2004); retroviral RNase H enzymes including the HIV enzyme (Nowotny 2009); retroviral integrases including the HIV integrase (Dyda et al., 1994); the hepatitis B virus (HBV) RNase H (Tavis et al., 2013); and the HSV nucleases pUL30, pUL12 and pUL15 (Boehmer & Lehman, 1997; Schumacher et al., 2012; Selvarajan et al., 2013). These enzymes function in a wide range of nucleic acid metabolic events, including RNA and DNA digestion, DNA recombination, DNA integration, DNA excision, replication fork repair, DNA repair, miRNA maturation, and miRNA-directed RNA cleavage. The canonical RNase H structure contains about 100 amino acids that fold into a 5-stranded β-sheet overlaid with 3 α-helices arranged like an "H". Within the active site are four conserved carboxylates (the "DEDD" motif) that coordinate two divalent cations (Nowotny et al., 2005).

The RNase H enzymatic mechanism is believed to involve both divalent cations (Klumpp et al., 2003; Yang and Steitz, 1995), although a 1-ion mechanism has been proposed (Goedken and Marqusee, 2001; Keck et al., 1998). There are three classes of RNAse Hs distinguished by how they bind to their substrates. RNA binding by the "stand-alone" class typified by *E. coli* RNAse H I is promoted by a basic "handle" region (Hostomsky et al., 1993; Kwun et al., 2001). Eukaryotic RNase Hs typically contain a "RHBD" domain that influences nucleic acid binding. Finally, substrate binding by the retroviral enzymes can either be a property of the RNase H domain itself (e.g., Moloney murine leukemia virus) or may require the reverse transcriptase domain to provide sufficient affinity for the nucleic acid substrate (e.g., HIV) (Hostomsky et al., 1993; Smith et al., 1994).

B. Herpesvirus

Herpesviruses are a diverse group of enveloped viruses having a large, double-stranded DNA genome enclosed in an icosahedral capsid (Pellet & Roizman 2013). The herpesviruses rely on the host cell RNA polymerase II for transcription but encode all of the enzymes needed for replication of their genomes, including DNA polymerase, helicase, primase, terminase, ribonucleotide reductase, and thymidine kinase. All herpesviruses share the capacity to establish latency in host cells, allowing them to maintain the infection for the life of the host. Periodic reactivation from latency in response to cues in the cellular environment leads to lytic replication at mucosal surfaces, causing recurrent disease and providing the opportunity for transmission to uninfected individuals.

The herpesviruses are divided into three subclasses based primarily on their cellular tropism and characteristics of the latent infection. The human alpha herpesviruses herpes simplex virus 1 (HSV-1) (Roizman et al., 2013), herpes simplex virus 2 (HSV-2) (Roizman et al., 2013) and Varicella-Zoster virus (VZV) (Arvin & Gilden 2013) establish latency in sensory neurons where they may remain quiescent for long periods of time. HSV-1 and HSV-2 are similar viruses with colinear genomes and 83% nucleotide sequence identity in protein coding regions (Dolan et al., 1998); VZV contains a smaller, less homologous genome. The human beta herpesviruses human cytomegalovirus (HCMV), human herpesvirus 6A (HHV-6A), human herpesvirus 6B (HHV-6B), and human herpesvirus 7 (HHV-7) (Yamanishi et al., 2013) establish latency predominantly in mononuclear cells. The human gamma herpesviruses Epstein-Barr virus (EBV) (Longnecker et al., 2013) and Kaposi's sarcoma herpesvirus (KSHV) (Damania & Cesarman, 2013) stimulate cellular proliferation upon infection. EBV infects B lymphocytes, where it establishes latency, and also epithelial cells. By contrast, endothelial cells harbor the latent reservoir of KSHV, although the virus infects numerous other cell types as well. The genomes of latent beta and gamma herpesviruses are replicated as the host cell divides in order to maintain latent infection.

Herpesviruses related the human alpha, beta, and gamma herpesviruses infect numerous animal species, including several of significant economic importance. Key among these are pseudorabies virus which infects pigs, Marek's disease virus which infects chickens, bovine herpesvirus, equine herpesvirus, and salmonid and related herpesviruses that infect game fish.

1. Pathology

Primary infections with herpesviruses produce a broad spectrum of disease. HSV-1 causes numerous maladies (Roizman et al., 2013): gingivostomatitis; eczema herpeticum; herpes gladiatorum; less common but frequently fatal encephalitis; and an increasing proportion of ulcerative anogenital lesions (Gilbert et al., 2011; Horowitz et al., 2011; Pena et al., 2010; Smith & Roberts 2009). Nearly two-thirds of the U.S. population has been exposed to HSV-1 (Xu et al., 2006). HSV-2 infects approximately 17% of Americans (Xu et al., 2006) and up to 75% of some demographics world-wide (Obasi et al., 1999 and Kamali et al., 1999), with an estimated global disease burden of more than half a billion people (Looker, et al., 2008). HSV-2 is the primary cause of ulcerative anogenital lesions. In addition, HSV-1 and HSV-2 may be transmitted from a pregnant woman to her child during birth, often causing potentially fatal disseminated disease in the newborn (Kimberlin 2007). HCMV is the most common in utero virus infection (Manicklal et al., 2013), and approximately 8,000 HCMV-infected infants born each year in the U.S. suffer sensorineural deafness, chorioretinitis, and/or mental retardation (James et al., 2009). In immunocompromised individuals, HCMV can cause mononucleosis, retinitis, colitis, pneumonitis, and esophagitis. These serious HCMV infections are associated with increased morbidity and mortality (Komatsu et al., 2014). EBV causes the vast majority of infectious mononucleosis, which strikes nearly half of young adults (Luzuriaga & Sullivan 2010). Notably, of the eight human herpesviruses, a vaccine is available only for VZV.

The novel capacity of herpesviruses to establish and reactivate from latency is also associated with numerous pathologies. HSV-1 causes recurrent cold sores; a significant proportion of devastating viral encephalitis; and corneal scarring known as herpetic stromal keratitis which is the most frequent infectious cause of blindness, afflicting nearly 400,000 persons annually in the U.S. (Roizman et al., 2013; Liesegang, 2001). HSV-2 frequently reactivates to cause genital ulcers and prior HSV-2 infection is associated with an increased risk of human immunodeficiency virus (HIV) acquisition and transmission (Roizman et al., 2013; Abu-Raddad et al., 2008; Freeman et al., 2006). Infants who survive HSV-1 or HSV-2 infections often experience life-long sequalae and periodic recurrent lesions (Kimberlin 2007 and James et al., 2009). VZV reactivates in up to half of older adults (Cohen 2013), and pain associated with the classic Zoster (shingles) rash and post-rash neuralgia can be excruciating. HCMV reactivation is associated with increased incidence of restenosis after angioplasty (Popovic et al., 2012), and also causes significant morbidity and mortality in recipients of bone marrow and solid organ transplants (Snydman 2008). Latent EBV infection is associated with a variety of cancers including Burkitt's lymphoma, two types of Hodgkin's lymphoma, non-Hodgkin's lymphoma, nasopharyngeal carcinoma, and post-transplant lymphoproliferative disease. Latent KSHV infection can lead to three types of cancer: Kaposi's sarcoma, pleural effusion lymphoma, and Castleman's disease (Damania & Cesarman 2013).

Veterinary herpesviruses also take a significant toll on livestock. Marek's disease is highly contagious, spreading rapidly through flocks of chickens that have not been vaccinated. It causes T cell lymphoma with infiltration of nerves and somatic organs, leading to paralysis and death in up to 80% of infected birds (Hirari, 2001). In addition, vaccine efficacy has declined with a concomitant increase in Marek's virus virulence (Gimeno, 2008). Pseudorabies (PRV) is the second most economically important viral disease of swine. Although PRV does not cause illness in adult swine, infection of pregnant sows results in a high incidence of fetal abortion or resorption (Smith, 1997). Piglets infected with PRV suffer coughing, sneezing, fever, constipation, and a variety of neurologic symptoms. Mortality in piglets less than one month of age is close to 100%, but declines rapidly with age (Nauwynck et al., 2007). Ruminants and dogs and cats are also susceptible to lethal PRV infection (Fenner et al., 1993). In cattle, symptoms include intense itching followed by neurological signs and death. In dogs, intense itching is accompanied by jaw and pharyngeal paralysis and subsequent death (Decaro et al., 2008). In cats, usually no symptoms are observed because the disease is so rapidly fatal (Gaskell et al., 2007). Bovine herpesviruses (BHV) cause a variety of illnesses in young cattle and can also cause abortion. Although the illnesses caused by BHVs are mostly not life-threatening, they are economically important diseases because infection may trigger a decline in meat and milk production and affect trade restrictions (Nandi et al., 2009). Caprine herpesviruses cause high rates of abortion, and necrotizing enteritis and necrotic foci in the lungs, liver and thymi of kids (Roperto et al., 2000; Chenier et al., 2004). Equine herpesviruses typically cause respiratory disease, but certain species also cause myeloencephalopathy in horses, abortion and occasionally neonatal mortality due to pneumonia (Fortier et al., 2010). The herpesviruses of various fish species can cause significant mortality in aquaculture settings, particularly at the fingerling stage (Hanson et al., 2011). Importantly, all of these viruses share the same basic genomic replication mechanisms, so if the presumed mechanism by which the NTS enzymes inhibit HSV-1 and HSV-2 is correct, most of the other herpesvirus pathogens should also be highly sensitive to NTS inhibitors. Development of NTS inhibitors into anti-herpesvirus drugs would be particularly valuable in cases like HCMV, where current antiviral therapies frequently drive resistance and are plagued by toxicity issues (Weller and Kuchta, 2013). Finally, NTS inhibitors may be promising candidates for pan anti-herpesvirus drug development due to similarities in replication mechanisms of all the herpesviruses.

2. Infection and Latency

Enveloped herpesvirus particles fuse with the plasma membrane of a cell, releasing viral regulatory proteins and the viral capsid containing the linear double-stranded DNA genome into the cytoplasm. The capsids deliver the viral genome to the nucleus via release through nuclear pores, whereupon the genome circularizes and becomes transcriptionally active. Viral infection at this point can proceed by two patterns, lytic or latent. In the lytic cycle, coordinated phases of viral transcription lead to expression of the viral regulatory proteins, viral enzymes, and concurrently with the onset of DNA replication, the viral structural proteins. Nascent viral capsids assemble in the nucleus and then bud through the nuclear membranes to acquire their envelope (Mettenleiter et al., 2009). Release from the cells is primarily lytic, resulting in the death of the cell. Alternatively, the virus may enter a latent state, where transcription is limited to a few viral regulatory loci and viral DNA replication is strictly limited. Upon recognition of appropriate cellular stimuli, viral transcription reverts to the lytic pattern and productive viral replication occurs.

Initial infections with alpha herpesviruses are lytic, resulting in dispersion of the virus to other cells and organs. These viruses establish latency in the unique environment of the neuron, and also in satellite cells in the case of VZV. During latency, replication of alpha herpesvirus DNA may occur at a low level because latently infected neurons contain multiple copies of the genome (Chen et al., 2002; Wang et al., 2005). Once latency is established, DNA replication increases markedly only during a reactivation event. Initial infections with beta herpesviruses are typically non-lytic but may cause cell-cell fusion. The gamma herpesviruses stimulate proliferation of infected cells, replicating their DNA along with cellular DNA replication to transmit copies of the viral genome to daughter cells (Longnecker et al., 2013). All the herpesviruses cause episodic lytic infection of at least some cell types, allowing them to be shed from mucosal surfaces to facilitate transmission to uninfected individuals.

3. Genomic Replication

Circularization of the linear double-stranded herpesvirus DNA occurs in the nucleus shortly after viral uncoating, presumably through a recombination-mediated event. Replication of the viral DNA occurs in the nucleus within three-dimensional domains termed replication compartments (Quinlan et al., 1984). DNA replication is thought to employ a double-stranded rolling circle mechanism [reviewed in (Weller & Coen 2012; Lehman & Boehmer 1999)]. In preparation for viral DNA replication, virus-encoded transcriptional activators upregulate expression of proteins involved in nucleic acid metabolism. DNA replication then initiates at one of three viral origins of DNA replication and is mediated through action of the viral ICP6 origin binding protein. (All viral gene names in this section are for HSV-1.) DNA synthesis is primed by the viral helicase/primase complex (pUL5, pUL8, and pUL52). DNA elongation occurs by coupled leading- and lagging-strand DNA synthesis through formation of a replication fork that is grossly similar to the forks that replicate cellular DNA. DNA synthesis is catalyzed by the pUL30 DNA polymerase/UL42 processivity protein complex that also possesses 5'-3' exonuclease, 3'-5' exonuclease, and RNase H activities. Helical torsion is relieved by the viral helicase/primase complex, and proper replication fork initiation, architecture and dynamics are promoted by the ICP8 single-stranded DNA binding protein. The initial product of DNA replication is a head-to-tail concatamer, but later in the replication cycle complex branched concatamers accumulate through recombination and/or re-initiation mechanisms. The concatamer is cleaved to unit length by the terminase complex (pUL15, pUL28, and pUL33) (Selvarajan et al., 2013) during encapsidation of the viral genome into pre-formed viral capsids.

4. Treatments

Herpesvirus DNA polymerase inhibitors (nucleoside analogs), including acyclovir, famciclovir, valaciclovir, penciclovir, and ganciclovir are the most common forms of treatment. A pyrophosphate analog, foscarnet, also inhibits the herpesvirus DNA polymerases. A DNA helicase inhibitor, AIC316 (pritelivir), was shown to reduce HSV-2 shedding in a phase 2 clinical trial (Wald et al., 2014). CMX001 (brincidofovir), an orally bioavailable lipid conjugate of cidofovir, potentiates the antiviral effect of acyclovir in mice inoculated intranasally with HSV-1 or HSV-2 (Prichard et al., 2011). N-Methanocarbathymidine (N-MCT) reduces lethality in a mouse model of HSV-2 infection (Quenelle et al., 2011) and a guinea pig model of neonatal herpes (Bernstein et al., 2011). N-MCT also reduces acute and recurrent disease caused by HSV-2 in an adult guinea pig model. The monoamine oxidase inhibitor tranylcypromine (TCP), which also blocks the activity of histone demethylase LSD1, reduces HSV-1 infection of the cornea, trigeminal ganglia and brain of mice, corneal disease, and percentage of mice shedding virus upon induced reactivation (Yao et al., 2014). TCP has also been tested in a rabbit eye model of recurrent infection with HSV-1 and the mouse and guinea pig models of HSV-2 genital infection. An acyclic nucleoside phosphonate, PMEO-DAPym, inhibits HSV replication in a variety of cultured cell types by targeting the viral DNA polymerase (Balzarini et al., 2013). The HIV integrase inhibitor, Raltegravir, has a small amount of inhibitory activity against replication of several herpesviruses in cultured cells (Zhou et al., 2014; Yan et al., 2014) and appears to target the polymerase processivity factor UL42 (Zhou et al., 2014). Two other integrase inhibitors, XZ15 and XZ45, reduce replication of HSV-1 in cell culture by approximately 800- to 8000-fold, respectively (Yan et al., 2014). XZ45 also inhibits HCMV replication and KSHV gene expression (Yan et al., 2014).

Therapy based on existing drugs such as acyclovir is incompletely effective (Johnston et al., 2012), and viral resistance to current nucleos(t)ide analog therapies is relatively common. Acyclovir resistant variants are particularly prevalent among children, the immunocompromised, and patients with herpetic stromal keratitis (Duan et al., 2008; Wang et al., 2011; Field & Vere Hodge, 2013; Morfin & Thouvenot, 2003; Andrei & Snoeck, 2013). Ganciclovir-resistant variants occur in the naturally circulating viral population (Drew et al., 1993) and can be selected in patients over time (Marfori et al., 2007; Imai et al., 2004; Drew et al., 2001; Drew et al., 1999).

C. Hepatitis B Virus

1. Biology

Hepatitis B virus, abbreviated HBV, is a species of the genus *Orthohepadnavirus*, which is likewise a part of the Hepadnaviridae family of viruses. This virus causes the disease hepatitis B. In addition to causing hepatitis B, infection with HBV can lead to cirrhosis and hepatocellular carcinoma. It has also been suggested that it may increase the risk of pancreatic cancer.

The hepatitis B virus is classified as the type species of the *Orthohepadnavirus*, which contains three other species: the Ground squirrel hepatitis virus, Woodchuck hepatitis virus, and the Woolly monkey hepatitis B virus. The genus is classified as part of the Hepadnaviridae family, which contains two other genera, the *Avihepadnavirus* and a second which has yet to be assigned. This family of viruses have not been assigned to a viral order. Viruses similar to hepatitis B have been found in all the Old World apes (orangutan, gibbons, gorillas and chimpanzees) and from a New World woolly monkey suggesting an ancient origin for this virus in primates.

The virus is divided into four major serotypes (adr, adw, ayr, ayw) based on antigenic epitopes present on its envelope proteins, and into eight genotypes (A-H) according to overall nucleotide sequence variation of the genome. The genotypes have a distinct geographical distribution and are used in tracing the evolution and transmission of the virus. Differences between genotypes affect the disease severity, course and likelihood of complications, and response to treatment and possibly vaccination.

Hepatitis B virus is a member of the Hepadnavirus family. The virus particle (virion) consists of an outer lipid envelope and an icosahedral nucleocapsid core composed of protein. The nucleocapsid encloses the viral DNA and a DNA polymerase that has reverse transcriptase activity similar to retroviruses. The outer envelope contains embedded proteins which are involved in viral binding of, and entry into, susceptible cells. The virus is one of the smallest enveloped animal viruses with a virion diameter of 42 nm, but pleomorphic forms exist, including filamentous and spherical bodies lacking a core. These particles are not infectious and are composed of the lipid and protein that forms part of the surface of the virion, which is called the surface antigen (HBsAg), and is produced in excess during the life cycle of the virus. It consists of HBsAg, HBcAg (HBeAg is an amino-terminal extension of HBcAg initiating from an upstream start codon), Hepatitis B virus DNA polymerase, and HBx. The functions of this non-structural regulatory protein are not yet well known.

The genome of HBV is made of circular DNA, but it is unusual because the DNA is not fully double-stranded. One end of the full length strand is linked to the viral DNA polymerase. The genome is 3020-3320 nucleotides long (for the full length strand) and 1700-2800 nucleotides long (for the short length strand). The negative-sense, (non-coding), is complementary to the viral mRNA. The viral DNA is found in the nucleus soon after infection of the cell. The partially double-stranded DNA is rendered fully double-stranded by completion of the (+) sense strand and removal of a protein molecule from the (−) sense strand and a short sequence of RNA from the (+) sense strand. A short terminal duplication of are removed from the ends of the (−)sense strand and the ends are rejoined. The mature nuclear form of the genome is called the "cccDNA".

There are four known genes encoded by the genome called C, X, P, and S. The core protein is coded for by gene C (HBcAg), and its start codon is preceded by an upstream in-frame AUG start codon from which the pre-core protein is produced. HBeAg is produced by proteolytic processing of the pre-core protein. The DNA polymerase is encoded by gene P. Gene S is the gene that codes for the surface antigen (HBsAg). The HBsAg gene is one long open reading frame but contains three in frame "start" (ATG) codons that divide the gene into three sections, pre-S1, pre-S2, and S. Because of the multiple start codons, polypeptides of three different sizes called large, middle, and small (pre-S1+pre-S2+S, pre-S2+S, or S) are produced. The function of the protein coded for by gene X is not fully understood.

There are eight known genotypes labeled A through H. A possible new "I" genotype has been described, but acceptance of this notation is not universal. Different genotypes may respond to treatment in different ways. The genotypes differ by at least 8% of the sequence and have distinct geographical distributions and this has been associated with anthropological history. Type F which diverges from the other genomes by 14% is the most divergent type known. Type A is prevalent in Europe, Africa and South-east Asia, including the Philippines. Type B and C are predominant in Asia; type D is common in the Mediterranean area, the Middle East and India; type E is localized in sub-Saharan Africa; type F (or H) is restricted to Central and South America. Type G has been found in France and Germany Genotypes A, D and F are predominant in Brazil and all genotypes occur in the United States with frequencies dependent on ethnicity. The E and F strains appear to have originated in aboriginal populations of Africa and the New World, respectively. Within genotypes 24 subtypes have been described which differ by 4-8% of the genome:

- Type A has two subtypes: Aa (A1) in Africa/Asia and the Philippines and Ae (A2) in Europe/United States.
- Type B has two distinct geographical distributions: Bj/B1 ('j'—Japan) and Ba/B2 ('a'—Asia). Type Ba has been further subdivided into four clades (B2-B4).
- Type C has two geographically subtypes: Cs (C1) in South-east Asia and Ce (C2) in East Asia. The C subtypes have been divided into five clades (C1-C5). A sixth clade (C6) has been described in the Philippines but only in one isolate to date. Type C1 is associated with Vietnam, Myanmar and Thailand; type C2 with Japan, Korea and China; type C3 with New Caledonia and Polynesia; C4 with Australia; and C5 with the Philippines. A further subtype has been described in Papua, Indonesia.
- Type D has been divided into 7 subtypes (D1-D7).
- Type F has been subdivided into 4 subtypes (F1-F4). F1 has been further divided in to 1a and 1b. In Venezuela subtypes F1, F2, and F3 are found in East and West Amerindians. Among South Amerindians only F3 was found. Subtypes Ia, III, and IV exhibit a restricted geographic distribution (Central America, the North and the South of South America respectively) while clades Ib and II are found in all the Americas except in the Northern South America and North America respectively.

The life cycle of hepatitis B virus is complex. Hepatitis B is one of a few known non-retroviral viruses which use reverse transcription as a part of its replication process:

- Attachment—The virus gains entry into the cell by binding to a receptor on the surface of the cell and enters it by endocytosis.
- Penetration—The virus membrane then fuses with the host cell's membrane releasing the DNA and core proteins into the cytoplasm.
- Uncoating—Because the virus multiplies via RNA made by a host enzyme, the viral genomic DNA has to be transferred to the cell nucleus by host proteins. The core proteins dissociate from the partially double-stranded viral DNA is then made fully double-stranded and transformed into covalently closed circular DNA (cccDNA) that serves as a template for transcription of four viral mRNAs.
- Replication—The cccDNA is the transcriptional template for all of HBV's RNAs. The largest of the mRNAs is called the pre-genomic RNA. This mRNA is longer than the viral genome and is packaged into nascent capsids along with the viral polymerase. Reverse transcription within the capsids is catalyzed by the coordinate activity of the polymerase's reverse transcriptase and ribonuclease H activities and results in the partially double-stranded viral DNA found within HBV virions.
- Assembly and Release—Progeny virions are formed budding of the viral capsid particles containing the viral DNA into endoplasmic-reticulum-derived membranes, where they pick up their envelope and HBsAgs are released from the cell by non-cytolytic secretion or are returned to the nucleus and re-cycled to produce even more copies of the nuclear cccDNA.

2. Treatment

Currently, there are seven FDA approved drugs in the U.S. to treat chronic HBV: Intron A® (Interferon Alpha), Pegasys® (Pegylated Interferon), Epivir HBV® (Lamivudine), Hepsera® (Adefovir), Baraclude® (Entecavir), Tyzeka® (Telbivudine), and Viread® (Tenofovir).

Adefovir, previously called bis-POM PMEA, with trade names Preveon and Hepsera®, is an orally-administered nucleotide analog reverse transcriptase inhibitor (ntRTI). It can be formulated as the pivoxil prodrug adefovir dipivoxil. Adefovir works by blocking reverse transcriptase, the enzyme that is crucial for the hepatitis B virus (HBV) to reproduce in the body because it synthesizes the viral DNA. It is approved for the treatment of chronic hepatitis B in adults with evidence of active viral replication and either evidence of persistent elevations in serum aminotransferases (primarily ALT) or histologically active disease. The main benefit of adefovir over drugs like lamivudine (below) is that it takes a much longer period of time before the virus develops resistance to it. Adefovir dipivoxil contains two pivaloyloxymethyl units, making it a prodrug form of adefovir.

Lamivudine (2',3'-dideoxy-3'-thiacytidine, commonly called 3TC) is a potent nucleoside analog reverse transcriptase inhibitor (nRTI). It is marketed by GlaxoSmithKline with the brand names Zeffix®, Heptovir®, Epivir®, and Epivir-HBV®. Lamivudine has been used for treatment of chronic hepatitis B at a lower dose than for treatment of HIV. It improves the seroconversion of e-antigen positive hepatitis B and also improves histology staging of the liver. Long term use of lamivudine unfortunately leads to emergence of a resistant hepatitis B virus (YMDD) mutant. Despite this, lamivudine is still used widely as it is well tolerated.

Lamivudine is an analogue of cytidine. It can inhibit both types (1 and 2) of HIV reverse transcriptase and also the reverse transcriptase of hepatitis B. It is phosphorylated to active metabolites that compete for incorporation into viral DNA. They inhibit the HIV reverse transcriptase enzyme competitively and act as a chain terminator of DNA synthesis. The lack of a 3'-OH group in the incorporated nucleoside analogue prevents the formation of the 5' to 3' phosphodiester linkage essential for DNA chain elongation, and therefore, the viral DNA growth is terminated.

Lamivudine is administered orally, and it is rapidly absorbed with a bio-availability of over 80%. Some research suggests that lamivudine can cross the blood-brain barrier. Lamivudine is often given in combination with zidovudine, with which it is highly synergistic. Lamivudine treatment has been shown to restore zidovudine sensitivity of previously resistant HIV. Lamivudine showed no evidence of carcinogenicity or mutagenicity in in vivo studies in mice and rats at doses from 10 to 58 times those used in humans.

Entecavir, abbreviated ETV, is an oral antiviral drug used in the treatment of hepatitis B infection. It is marketed under the trade names Baraclude® (BMS) and Entaliv® (DRL). Entecavir is a nucleoside analog (more specifically, a guanosine analogue) that inhibits reverse transcription, DNA replication and transcription in the viral replication process. The drug's manufacturer claims that entecavir is more efficacious than previous agents used to treat hepatitis B (lamivudine and adefovir). Entecavir was approved by the U.S. FDA in March 2005 and is used to treat chronic hepatitis B. It also helps prevent the hepatitis B virus from multiplying and infecting new liver cells. Entecavir is also indicated for the treatment of chronic hepatitis B in adults with HIV/AIDS infection. However, entecavir is not active against HIV.

Telbivudine is an antiviral drug used in the treatment of hepatitis B infection. It is marketed by Swiss pharmaceutical company Novartis under the trade names Sebivo® (Europe) and Tyzeka® (United States). Clinical trials have shown it to be significantly more effective than lamivudine or adefovir, and less likely to cause resistance. Telbivudine is a synthetic thymidine nucleoside analogue; it is the L-isomer of thymidine. It is taken once daily.

Tenofovir disoproxil fumarate (TDF or PMPA), marketed by Gilead Sciences under the trade name Viread®, it is also a nucleotide analogue reverse transcriptase inhibitor (nRTIs) which blocks the HBV reverse transcriptase, an enzyme crucial to viral production. Tenofovir disoproxil fumarate is a prodrug form of tenofovir. Tenofovir is also available in a fixed-dose combination with emtricitabine in a product with the brand name Truvada for once-a-day dosing. Atripla, a fixed-dose triple combination of tenofovir, emtricitabine and efavirenz, was approved by the FDA on 12 Jul. 2006 and is now available, providing a single daily dose for the treatment of HIV. Tenofovir is indicated in combination with other antiretroviral agents for the treatment of HIV-1 infection in adults. This indication is based on analyses of plasma HIV-1 RNA levels and CD4 cell counts in controlled studies of tenofovir in treatment-naive and treatment-experienced adults. There are no study results demonstrating the effect of tenofovir on the clinical progression of HIV. It also has activity against wild-type and lamivudine-resistant HBV.

3. The HBV RNaseH as a Drug Target

The HBV RNase H is an NTS enzyme. Mutational analysis of the HBV RNase H revealed the characteristic DEDD active site of the NTS family to comprise HBV residues D702, E731, D750, and D790 (numbering for HBV strain adw2) (Gerelsaikhan et al., 1996; Tavis et al., 2013). No drugs exist against the HBV RNaseH despite its essential role in viral replication, but HBV RNaseH has recently been targeted for antiviral drug development (Tavis et al. 2013; Cai et al., 2014; Edwards et al., 2017; Edwards et al., 2019; Hu et al., 2013; Lomonosova et al., 2017; Long et al., 2018; Lu et al., 2015; and Lu et al., 2016). The compounds used in this study belong to the α-hydroxytropolone chemotype (Meck et al., 2014). α-hydroxytropolones are believed to bind directly to the enzyme's active site through coordination of the two $Mg^{++}$ ions in the enzyme active site based on both their inhibition of HBV RNaseH in biochemical assays (Tavis et al. 2013; Cai et al., 2014; Edwards et al., 2017; Edwards et al., 2019; Hu et al., 2013; Lomonosova et al., 2017; Long et al., 2018; Lu et al., 2015; and Lu et al., 2016) and crystal studies showing binding of an α-hydroxytropolone into the active site of the HIV RNaseH (Himmel et al., 2009).

D. *Cryptococcus neoformans*

1. Biology

*Cryptococcus neoformans*, a single cell yeast of the Tremellaceae family in the phylum basidiomycota, is a significant opportunistic pathogen of the immunocompromised, especially AIDS, patients. *C. neoformans* causes pulmonary infections and meningoencephalitis, which are fatal if untreated. *C. neoformans* was first observed clinically in the 1960's with the advent of organ transplant and aggressive treatment of cancers and other diseases that resulted in immunosuppression (Pyrgo et al., 2013). The number of AIDS patients infected with *C. neoformans* peaked in the mid-1990s, driven by increased frequency of HIV infections. The advent of effective anti-retroviral therapies (ART) in 1997 significantly reduced the number of HIV-positive patients with cryptococcosis (Mirza 2003), with ca. 2.9% of AIDS patients in the US positive for the cryptococcal antigen (McKenney 2014). This reduction has not been observed in resource-limited countries, especially in areas with high disease burden such as sub-Saharan Africa. There, the prevalence of cryptococcal meningitis (CM) in HIV-infected patients is between 25 and 45% (Sloan 2014). CM causes high mortality among AIDS patients, surpassing TB-associated mortality in some areas of sub-Saharan Africa (Rajasingham 2017). A closely related *Cryptococcus* species, *C. gattii*, can infect immunocompetent people and is endemic in tropical areas. It was first observed in temperate regions in an outbreak on Vancouver Island that has since expanded geographically (Byrnes 2010 and Datta 2009). *C. gattii* has also been identified as the source of ongoing infections among immunocompromised patients in southern California and in the southeastern US (Pyrgos 2013, Brynes 2011; Lockhart 2013; Springer 2014).

2. Treatment

There are only three approved drugs effective for cryptococcosis, all of which were developed decades ago. Amphotericin B (AmB), under the trade names AmBiosome® or Amphotec®, binds ergosterol, is a highly specific inhibitor of fungi but has very significant toxicity and its use in resource-poor areas is limited since it is administered intravenously (Hamill 2013). 5-fluorocytosine (5-FC), under the trade name Ancobon® or as a generic, targets pyrimidine biosynthesis but is used only in combination with other drugs because of the high rate of resistance evolution. Fluconazole (FLC), under the trade names Diflucan® or ActFluconazole®, also targets ergosterol biosynthesis but is only fungistatic and leaves patients susceptible to relapse. The current standard of treatment is a combination of 5-fluorocytosine and AmB, but efficacy is limited even in resource-rich settings where mortality from CM among all patients, regardless of the underlying condition, is between 10 and 35% (Lortholary 2007; Mdodo 2010; Bratton 2012; Brizendine 2013). The most recently approved antifungal classes of drugs, the echinocandins, are not active against *Cryptococcus* (Pfaller 2017).

3. Nucleotidylsupertransferases as a Drug Target in *C. neoformans*

There are 3900 known or predicted protein coding genes in *C. neoformans* (Janbon 2014). To date, 63 genes are annotated or predicted to encode a protein in the nucleotidyltransferase superfamily (NTS) (Janbon 2014). Only a few members of the NTS family have been characterized in *C. neoformans*, but at least two exonucleases are known to be essential, validating their potential as a viable drug target in this organism (Ianiri 2015, Goebels 2013).

E. Chemical Entity

1. Chemical Genus and Species

The compounds of the present disclosure appear to inhibit a different enzymatic activity than the existing commercially available anti-herpesvirus drugs and does so with a capacity to suppress virus replication at very low toxicity to uninfected cells. This fact implies that these compounds may be effective against viral isolates resistant to the existing drugs and suggests that these drugs could be combined effectively with the existing drugs to both increase efficacy and to reduce the rate of resistance development to either drug. Furthermore, the compounds were more effective than a currently accepted first line therapy, acyclovir, indicating that it may be more effective than the existing drugs when formulated for pharmaceutical delivery. These compounds may be used to treat acyclovir resistant viral mutants.

The compounds of the present disclosure are represented by the formula below:

(I)

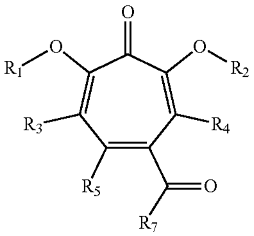

or (II)

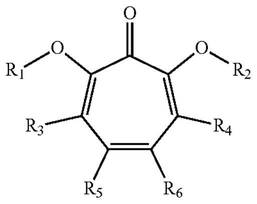

wherein the variables are defined herein.

TABLE 1

| Compounds of the Present Disclosure | |
|---|---|
| Compound ID | Structure |
| #384 | 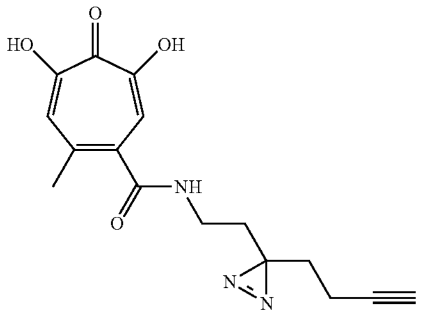 [SMILES: C#CCCC1(CCNC(=O)c2cc(O)c(=O)c(O)cc2C)N=N1] |
| #388 | 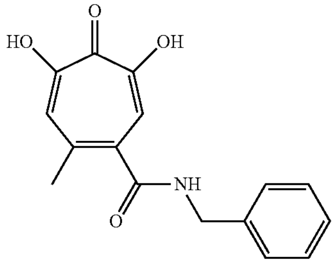 [SMILES: Cc1cc(O)c(=O)c(O)cc1C(=O)NCc1ccccc1] |

TABLE 1-continued
| Compounds of the Present Disclosure | |
|---|---|
| Compound ID | Structure |
| #389 | 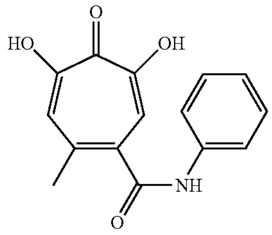 [SMILES: Cc1cc(O)c(=O)c(O)cc1C(=O)Nc1ccccc1] |
| #390 | 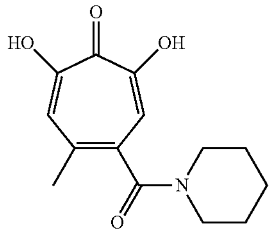 [SMILES: Cc1cc(O)c(=O)c(O)cc1C(=O)N1CCCCC1] |
| #391 | 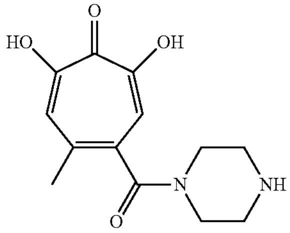 [SMILES: Cc1cc(O)c(=O)c(O)cc1C(=O)N1CCNCC1] |
| #404 | 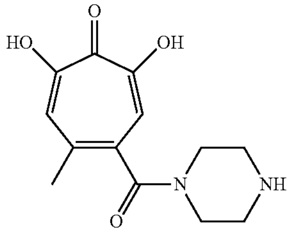 [SMILES: Cc1cc(O)c(=O)c(O)cc1C(=O)N1CCNCC1] |
| #539 | 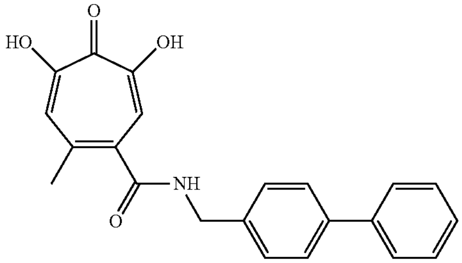 [SMILES: Cc1cc(O)c(=O)c(O)cc1C(=O)NCc1ccc(-c2ccccc2)cc1] |

TABLE 1-continued
| Compound ID | Structure |
| --- | --- |
| Compounds of the Present Disclosure | |
| #707 | 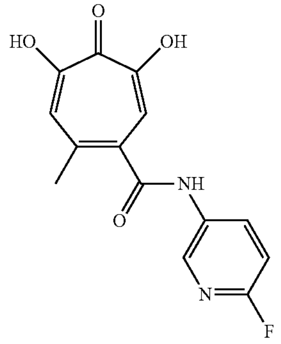 [SMILES: Cc1cc(O)c(=O)c(O)cc1C(=O)Nc1ccc(F)nc1] |
| #708 | 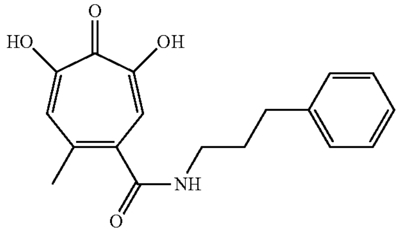 [SMILES: Cc1cc(O)c(=O)c(O)cc1C(=O)NCCCc1ccccc1] |
| #709 | 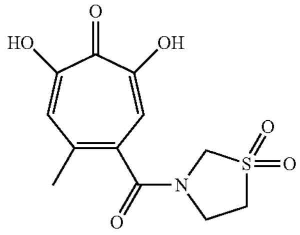 [SMILES: Cc1cc(O)c(=O)c(O)cc1C(=O)N1CCS(=O)(=O)C1] |
| #710 | 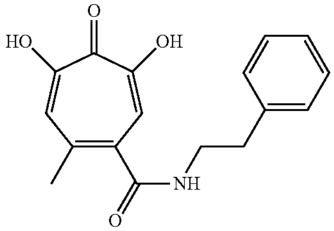 [SMILES: Cc1cc(O)c(=O)c(O)cc1C(=O)NCCc1ccccc1] |
| #711 | 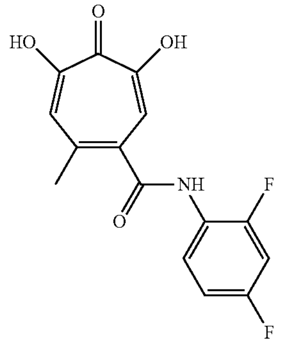 [SMILES: Cc1cc(O)c(=O)c(O)cc1C(=O)Nc1ccc(F)cc1F] |

TABLE 1-continued
| Compounds of the Present Disclosure | |
|---|---|
| Compound ID | Structure |
| #712 | 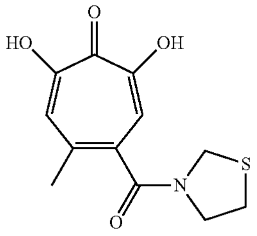 [SMILES: Cc1cc(O)c(=O)c(O)cc1C(=O)N1CCSC1] |
| #793 | 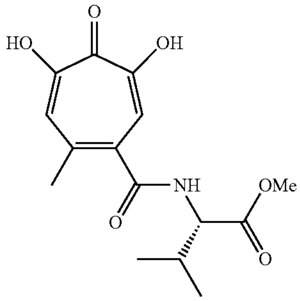 [SMILES: COC(=O)[C@@H](NC(=O)c1cc(O)c(=O)c(O)cc1C)C(C)C] |
| #794 | 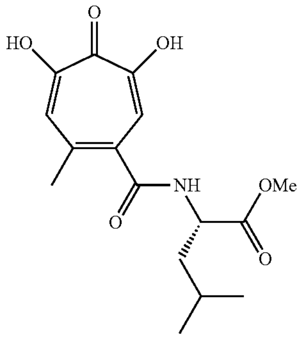 [SMILES: COC(=O)[C@H](CC(C)C)NC(=O)c1cc(O)c(=O)c(O)cc1C] |
| #795 | 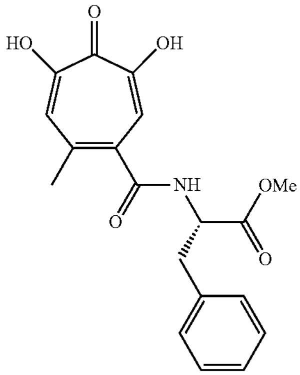 [SMILES: COC(=O)[C@H](Cc1ccccc1)NC(=O)c1cc(O)c(=O)c(O)cc1C] |

TABLE 1-continued
| Compounds of the Present Disclosure | |
|---|---|
| Compound ID | Structure |
| #796 | 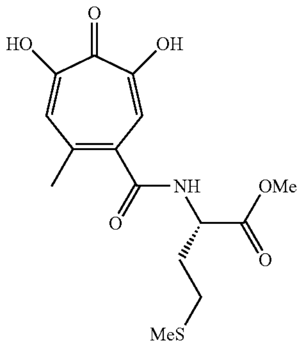 [SMILES: COC(=O)[C@H](CCSC)NC(=O)c1cc(O)c(=O)c(O)cc1C] |
| #797 | 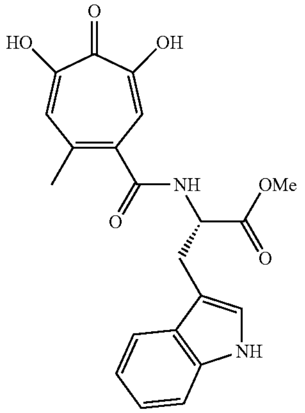 [SMILES: COC(=O)[C@H](Cc1c[nH]c2ccccc12)NC(=O)c1cc(O)c(=O)c(O)cc1C] |
| #798 | 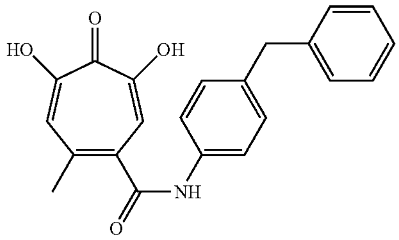 [SMILES: Cc1cc(O)c(=O)c(O)cc1C(=O)Nc1ccc(Cc2ccccc2)cc1] |
| #799 | 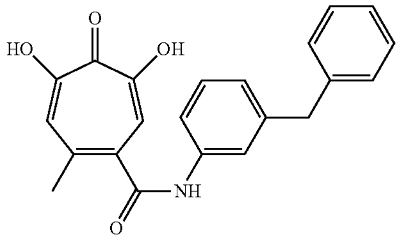 [SMILES: Cc1cc(O)c(=O)c(O)cc1C(=O)Nc1cccc(Cc2ccccc2)c1] |
| #800 | 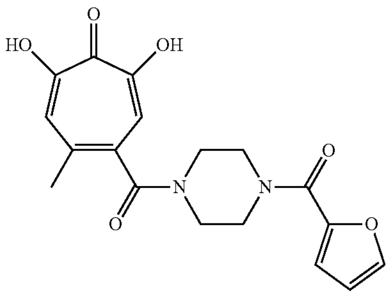 [SMILES: Cc1cc(O)c(=O)c(O)cc1C(=O)N1CCN(C(=O)c2ccco2)CC1] |

TABLE 1-continued
| Compounds of the Present Disclosure | |
|---|---|
| Compound ID | Structure |
| #801 | 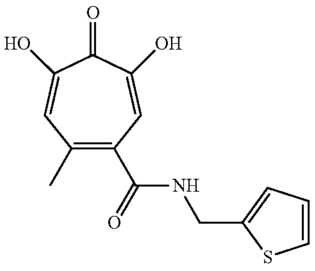 [SMILES: Cc1cc(O)c(=O)c(O)cc1C(=O)NCc1cccs1] |
| #802 | 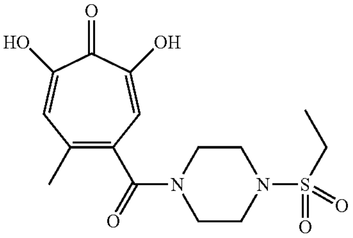 [SMILES: CCS(=O)(=O)N1CCN(C(=O)c2cc(O)c(=O)c(O)cc2C)CC1] |
| #803 | 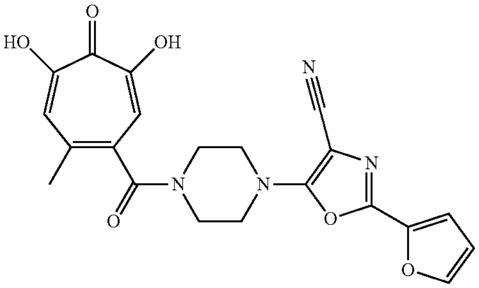 [SMILES: Cc1cc(O)c(=O)c(O)cc1C(=O)N1CCN(c2oc(-c3ccco3)nc2C#N)CC1] |
| #804 | 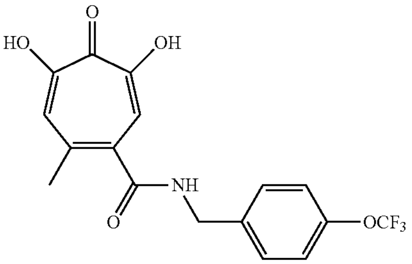 [SMILES: Cc1cc(O)c(=O)c(O)cc1C(=O)NCc1ccc(OC(F)(F)F)cc1] |
| #805 | 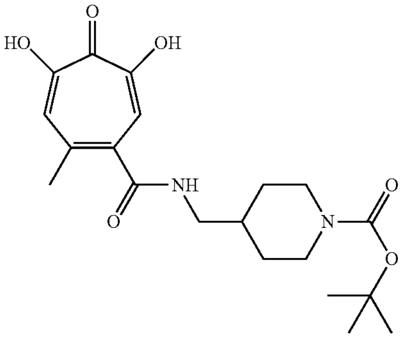 [SMILES: Cc1cc(O)c(=O)c(O)cc1C(=O)NCC1CCN(C(=O)OC(C)(C)C)CC1] |

TABLE 1-continued
| Compound ID | Structure |
| --- | --- |
| #806 | 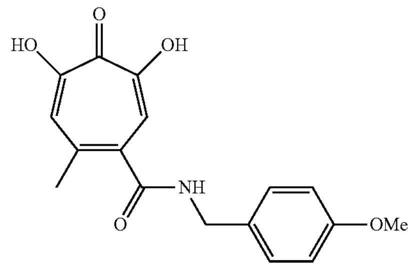 [SMILES: COc1ccc(CNC(=O)c2cc(O)c(=O)c(O)cc2C)cc1] |
| #807 | 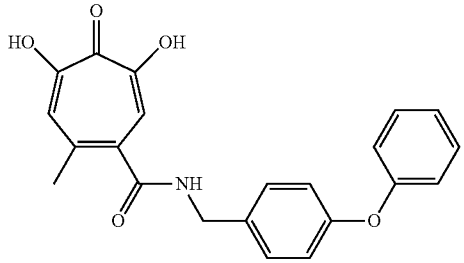 [SMILES: Cc1cc(O)c(=O)c(O)cc1C(=O)NCc1ccc(Oc2ccccc2)cc1] |
| #808 | 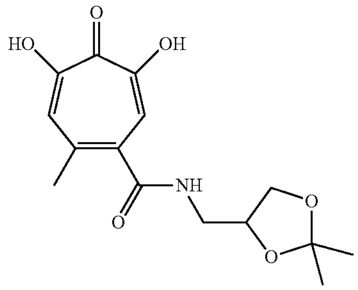 [SMILES: Cc1cc(O)c(=O)c(O)cc1C(=O)NCC1COC(C)(C)O1] |
| #809 | 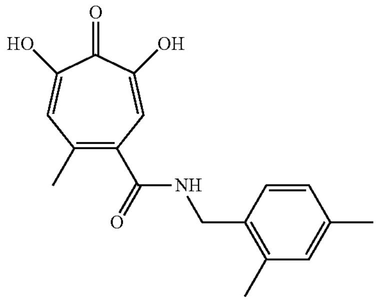 [SMILES: Cc1ccc(CNC(=O)c2cc(O)c(=O)c(O)cc2C)c(C)c1] |
| #810 | 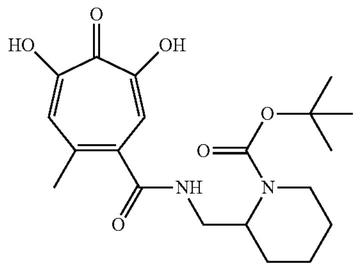 [SMILES: Cc1cc(O)c(=O)c(O)cc1C(=O)NCC1CCCCN1C(=O)OC(C)(C)C] |
Compounds of the Present Disclosure TABLE 1-continued
| Compounds of the Present Disclosure | |
|---|---|
| Compound ID | Structure |
| #834 | 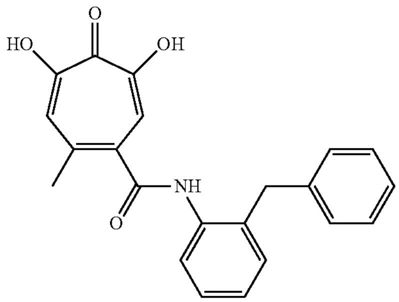 [SMILES: Cc1cc(O)c(=O)c(O)cc1C(=O)Nc1ccccc1Cc1ccccc1] |
| #835 | 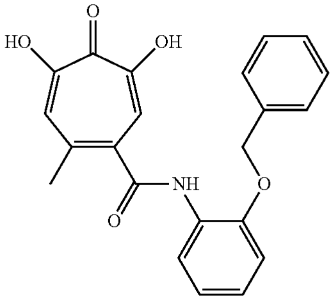 [SMILES: Cc1cc(O)c(=O)c(O)cc1C(=O)Nc1ccccc1OCc1ccccc1] |
| #836 | 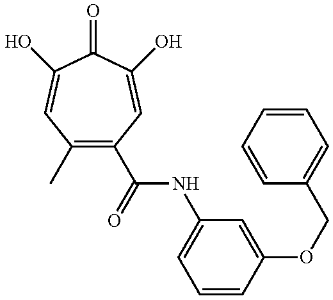 [SMILES: Cc1cc(O)c(=O)c(O)cc1C(=O)Nc1cccc(OCc2ccccc2)c1] |
| #837 | 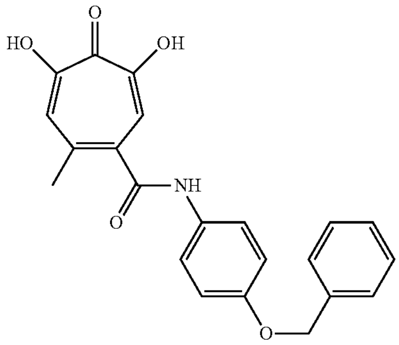 [SMILES: Cc1cc(O)c(=O)c(O)cc1C(=O)Nc1ccc(OCc2ccccc2)cc1] |

TABLE 1-continued
| Compounds of the Present Disclosure | |
|---|---|
| Compound ID | Structure |
| #867 | 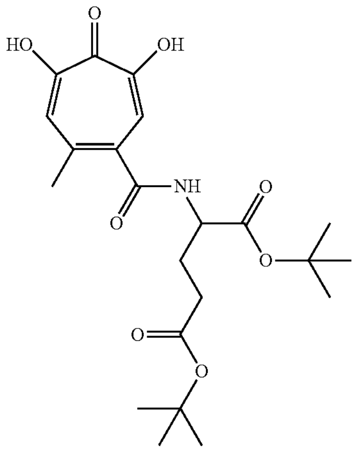 [SMILES: Cc1cc(O)c(=O)c(O)cc1C(=O)NC(CCC(=O)OC(C)(C)C)C(=O)OC(C)(C)C] |
| #868 | 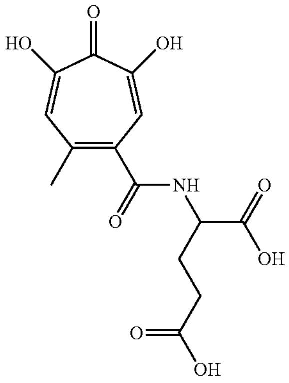 [SMILES: Cc1cc(O)c(=O)c(O)cc1C(=O)NC(CCC(=O)O)C(=O)O] |
| #869 | 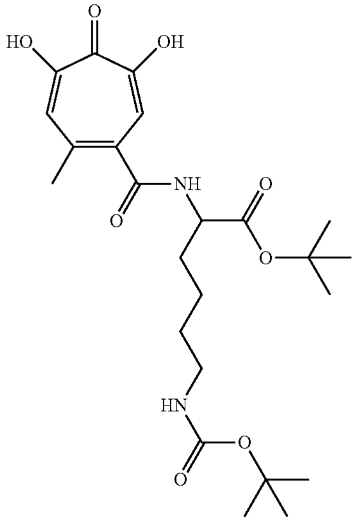 [SMILES: Cc1cc(O)c(=O)c(O)cc1C(=O)NC(CCCCNC(=O)OC(C)(C)C)C(=O)OC(C)(C)C] |

TABLE 1-continued
| Compounds of the Present Disclosure | |
|---|---|
| Compound ID | Structure |
| #870 | 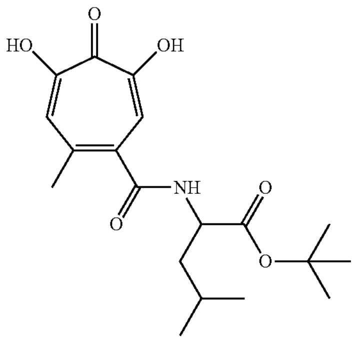 [SMILES: Cc1cc(O)c(=O)c(O)cc1C(=O)NC(CC(C)C)C(=O)OC(C)(C)C] |
| #871 | 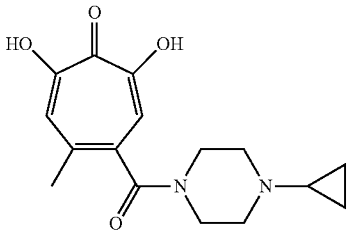 [SMILES: Cc1cc(O)c(=O)c(O)cc1C(=O)N1CCN(C2CC2)CC1] |
| #872 | 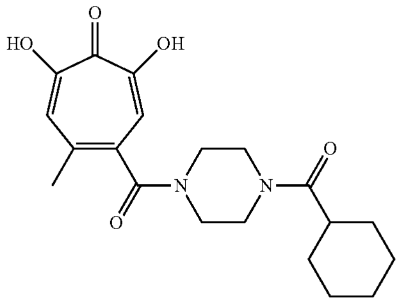 [SMILES: Cc1cc(O)c(=O)c(O)cc1C(=O)N1CCN(C(=O)C2CCCCC2)CC1] |
| #873 | 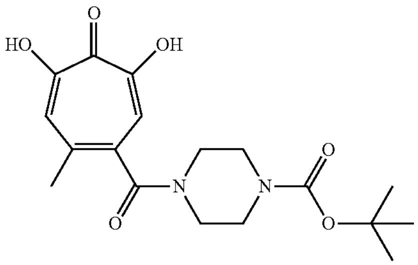 [SMILES: Cc1cc(O)c(=O)c(O)cc1C(=O)N1CCN(C(=O)OC(C)(C)C)CC1] |
| #874 | 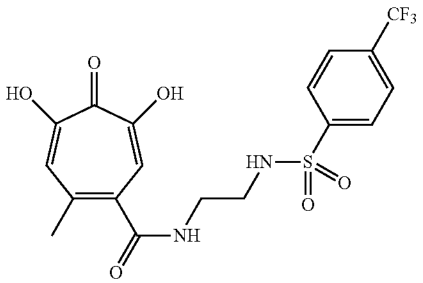 [SMILES: Cc1cc(O)c(=O)c(O)cc1C(=O)NCCNS(=O)(=O)c1ccc(C(F)(F)F)cc1] |

TABLE 1-continued
| Compounds of the Present Disclosure | |
|---|---|
| Compound ID | Structure |
| #875 | 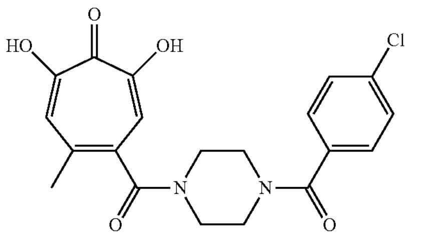 [SMILES: Cc1cc(O)c(=O)c(O)cc1C(=O)N1CCN(C(=O)c2ccc(Cl)cc2)CC1] |
| #876 | 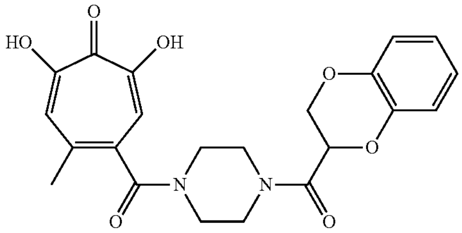 [SMILES: Cc1cc(O)c(=O)c(O)cc1C(=O)N1CCN(C(=O)C2COc3ccccc3O2)CC1] |
| #877 | 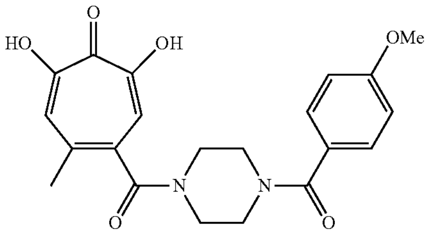 [SMILES: COc1ccc(C(=O)N2CCN(C(=O)c3cc(O)c(=O)c(O)cc3C)CC2)cc1] |
| #917 | 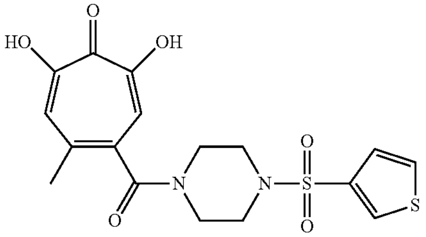 [SMILES: Cc1cc(O)c(=O)c(O)cc1C(=O)N1CCN(S(=O)(=O)c2ccsc2)CC1] |
| #918 | 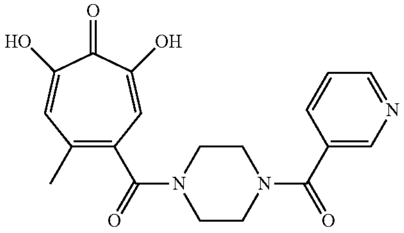 [SMILES: Cc1cc(O)c(=O)c(O)cc1C(=O)N1CCN(C(=O)c2cccnc2)CC1] |
| #919 | 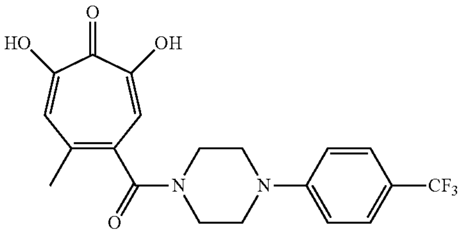 [SMILES: Cc1cc(O)c(=O)c(O)cc1C(=O)N1CCN(c2ccc(C(F)(F)F)cc2)CC1] |

TABLE 1-continued
| Compounds of the Present Disclosure | |
|---|---|
| Compound ID | Structure |
| #920 | 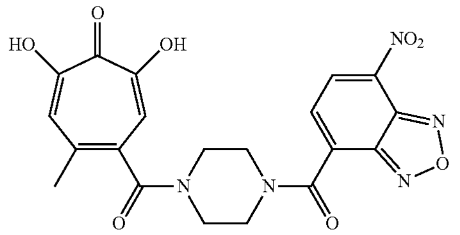 [SMILES: Cc1cc(O)c(=O)c(O)cc1C(=O)N1CCN(C(=O)c2ccc([N+](=O)[O-])c3nonc23)CC1] |
| #1016 | 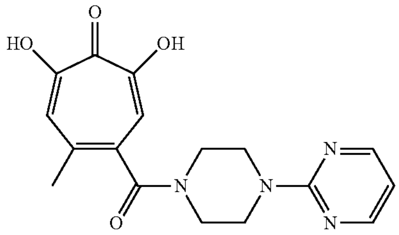 [SMILES: Cc1cc(O)c(=O)c(O)cc1C(=O)N1CCN(c2ncccn2)CC1] |
| #1017 | 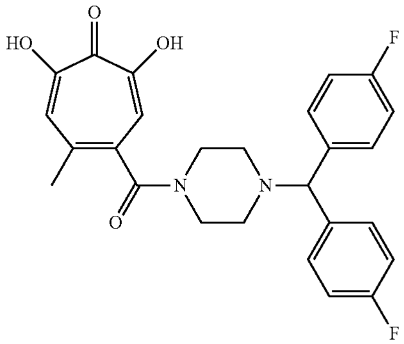 [SMILES: Cc1cc(O)c(=O)c(O)cc1C(=O)N1CCN(C(c2ccc(F)cc2)c2ccc(F)cc2)CC1] |
| #1018 | 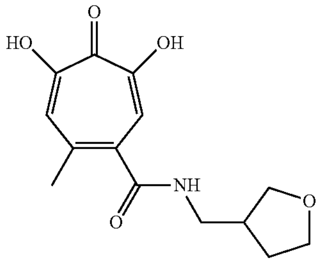 [SMILES: Cc1cc(O)c(=O)c(O)cc1C(=O)NCC1CCOC1] |
| #1019 | 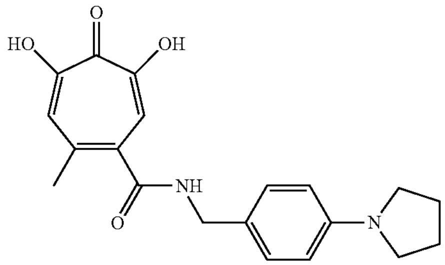 [SMILES: Cc1cc(O)c(=O)c(O)cc1C(=O)NCc1ccc(N2CCCC2)cc1] |

TABLE 1-continued
| Compound ID | Structure |
| --- | --- |
| #1020 | 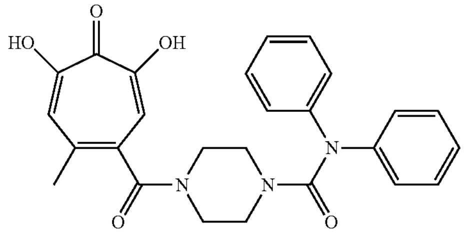 [SMILES: Cc1cc(O)c(=O)c(O)cc1C(=O)N1CCN(C(=O)N(c2ccccc2)c2ccccc2)CC1] |
| #1021 | 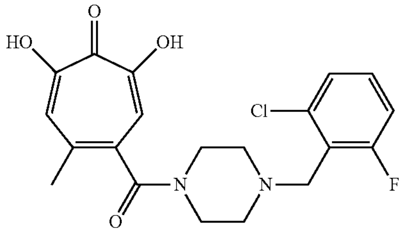 [SMILES: Cc1cc(O)c(=O)c(O)cc1C(=O)N1CCN(Cc2c(F)cccc2Cl)CC1] |
| #1039 | 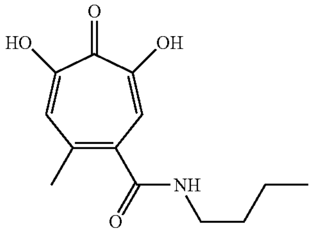 [SMILES: CCCCNC(=O)c1cc(O)c(=O)c(O)cc1C] |
| #336 | 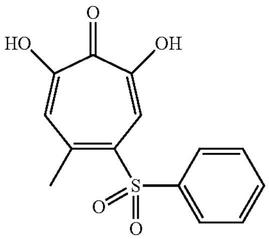 [SMILES: Cc1cc(O)c(=O)c(O)cc1S(=O)(=O)c1ccccc1] |
| #337 | 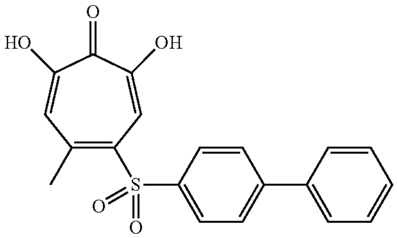 [SMILES: Cc1cc(O)c(=O)c(O)cc1S(=O)(=O)c1ccc(-c2ccccc2)cc1] |
| #367 | 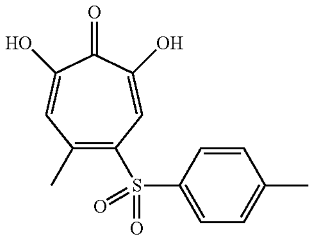 [SMILES: Cc1ccc(S(=O)(=O)c2cc(O)c(=O)c(O)cc2C)cc1] |
Compounds of the Present Disclosure TABLE 1-continued
| Compounds of the Present Disclosure | |
|---|---|
| Compound ID | Structure |
| #382 | 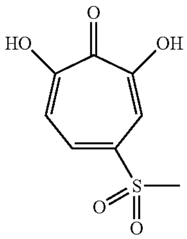 |
| #385 | 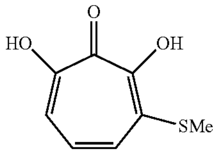 [SMILES: CSc1cccc(O)c(=O)c1O] |
| #386 | 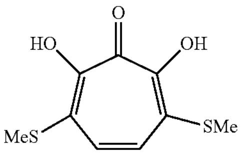 [SMILES: CSc1ccc(SC)c(O)c(=O)c1O] |
| #387 | 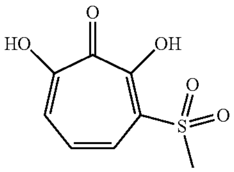 |
| #408 | 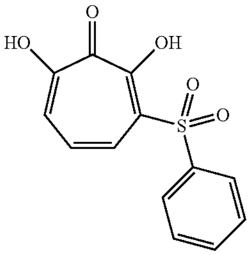 [SMILES: O=c1c(O)cccc(S(=O)(=O)c2ccccc2)c1O] |
| #535 | 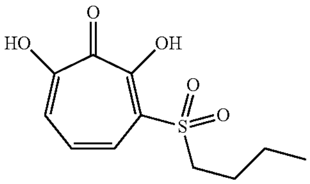 [SMILES: CCCCS(=O)(=O)c1cccc(O)c(=O)c1O] |
| #536 | 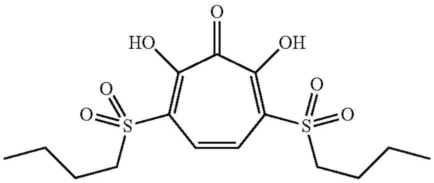 [SMILES: CCCCS(=O)(=O)c1ccc(S(=O)(=O)CCCC)c(O)c(=O)c1O] |

TABLE 1-continued
| Compounds of the Present Disclosure | |
|---|---|
| Compound ID | Structure |
| #537 | 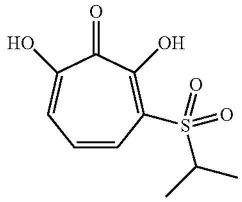 [SMILES: CC(C)S(=O)(=O)c1cccc(O)c(=O)c1O] |
| #538 | 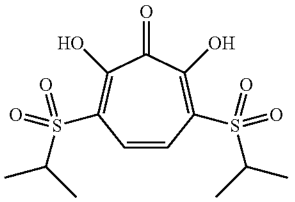 [SMILES: CC(C)S(=O)(=O)c1ccc(S(=O)(=O)C(C)C)c(O)c(=O)c1O] |
| #691 | 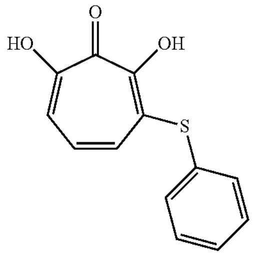 [SMILES: O=c1c(O)cccc(Sc2ccccc2)c1O] |
| #693 | 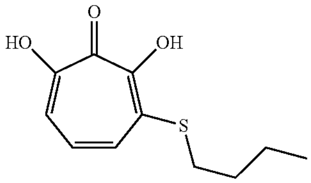 |
| #694 | 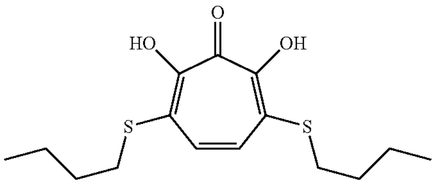 [SMILES: CCCCSc1ccc(SCCCC)c(O)c(=O)c1O] |
| #695 | 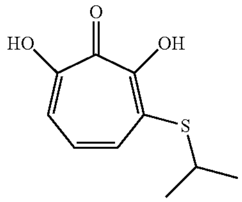 |
| #696 | 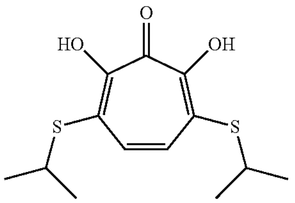 [SMILES: CC(C)Sc1ccc(SC(C)C)c(O)c(=O)c1O] |

TABLE 1-continued
| Compounds of the Present Disclosure | |
|---|---|
| Compound ID | Structure |
| #697 | 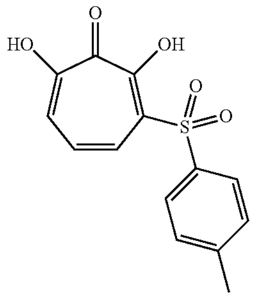 [SMILES: Cc1ccc(S(=O)(=O)c2cccc(O)c(=O)c2O)cc1] |
| #698 | 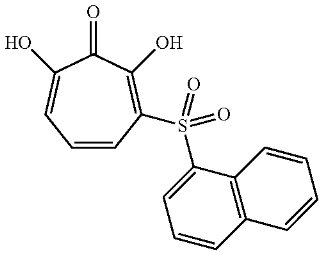 [SMILES: O=c1c(O)cccc(S(=O)(=O)c2cccc3ccccc23)c1O] |
| #699 | 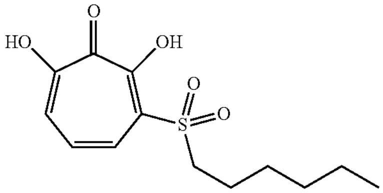 [SMILES: CCCCCCS(=O)(=O)c1cccc(O)c(=O)c1O] |
| #700 | 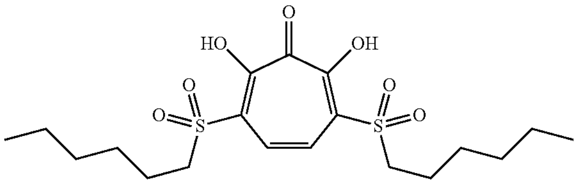 [SMILES: CCCCCCS(=O)(=O)c1ccc(S(=O)(=O)CCCCCC)c(O)c(=O)c1O] |
| #701 | 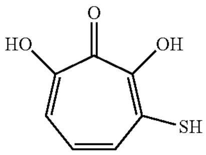 |
| #702 | 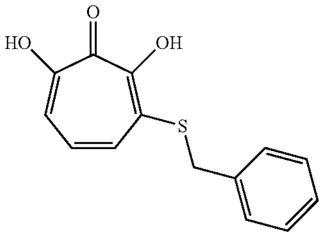 [SMILES: O=c1c(O)cccc(SCc2ccccc2)c1O] |

TABLE 1-continued
| Compounds of the Present Disclosure | |
|---|---|
| Compound ID | Structure |
| #703 | 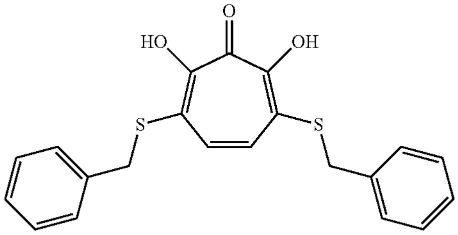 [SMILES: O=c1c(O)c(SCc2ccccc2)ccc(SCc2ccccc2)c1O] |
| #704 | 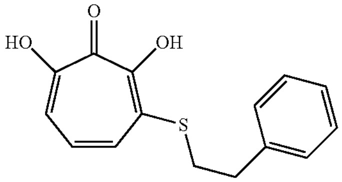 [SMILES: O=c1c(O)cccc(SCCc2ccccc2)c1O] |
| #705 | 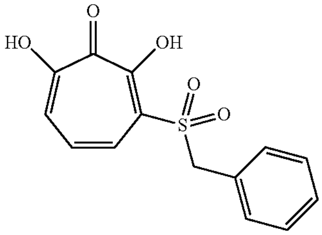 [SMILES: O=c1c(O)cccc(S(=O)(=O)Cc2ccccc2)c1O] |
| #706 | 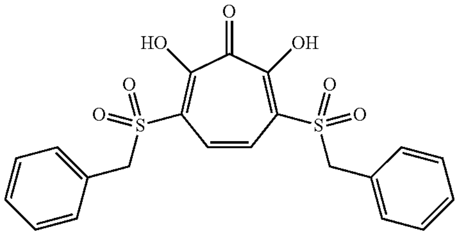 [SMILES: O=c1c(O)c(S(=O)(=O)Cc2ccccc2)ccc(S(=O)(=O)Cc2ccccc2)c1O] |
| #838 | 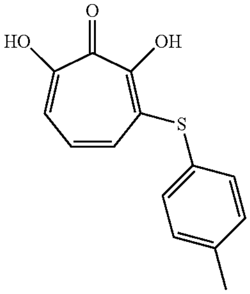 [SMILES: Cc1ccc(Sc2cccc(O)c(=O)c2O)cc1] |
| #839 | 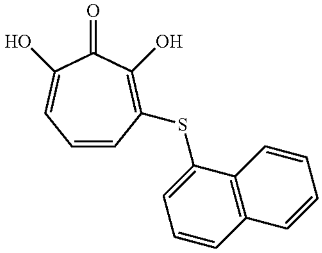 [SMILES: O=c1c(O)cccc(Sc2cccc3ccccc23)c1O] |

TABLE 1-continued

| Compounds of the Present Disclosure | |
|---|---|
| Compound ID | Structure |
| #840 | 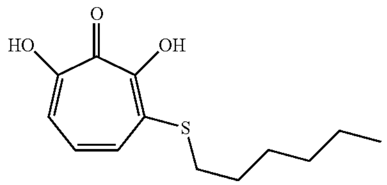 [SMILES: CCCCCCSc1cccc(O)c(=O)c1O] |
| #841 | 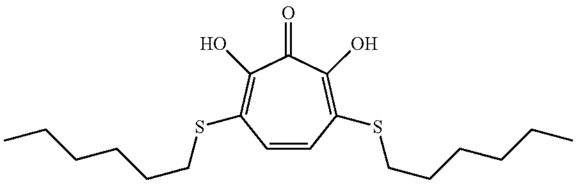 [SMILES: CCCCCCSc1ccc(SCCCCCC)c(O)c(=O)c1O] |

The compounds of the present disclosure may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the disclosure may contain one or more asymmetrically-substituted carbon or nitrogen atoms and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present disclosure may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

2. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or $—CO_2H$); "halo" means independently —F, —Cl, —Br or —I; "amino" means $—NH_2$; "hydroxyamino" means —NHOH; "nitro" means $—NO_2$; imino means =NH; "cyano" means —CN;

"isocyanate" means —N═C═O; "azido" means $-N_3$; in a monovalent context "phosphate" means $-OP(O)(OH)_2$ or a deprotonated form thereof; in a divalent context "phosphate" means —OP(O)(OH)O— or a deprotonated form thereof; "mercapto" means —SH; and "thio" means ═S; "sulfonyl" means $-S(O)_2-$; "hydroxylsulfonyl" means $-SO_2OH$; "aminosulfonyl" means $-SO_2NH_2$ and "sulfinyl" means —S(O)—.

In the context of chemical formulas, the symbol "—" means a single bond, "═" means a double bond, and "≡" means triple bond. The symbol "----" represents an optional bond, which if present is either single or double. The symbol "" represents a single bond or a double bond. Thus, for example, the formula

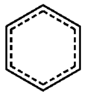

includes

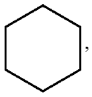, 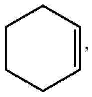, 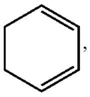, 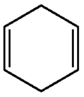 and 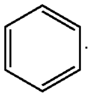.

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "", when drawn perpendicularly across a bond (e.g.,

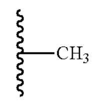

for methyl) indicates a point of attachment of the group. It is noted that the point of attachment is typically only identified in this manner for larger groups in order to assist the reader in unambiguously identifying a point of attachment. The symbol "" means a single bond where the group attached to the thick end of the wedge is "out of the page." The symbol "" means a single bond where the group attached to the thick end of the wedge is "into the page". The symbol "" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

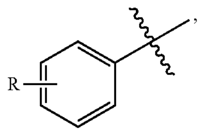

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

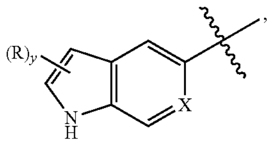

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and compound classes below, the number of carbon atoms in the group is as indicated as follows: "Cn" defines the exact number (n) of carbon atoms in the group/class. "C≤n" defines the maximum number (n) of carbon atoms that can be in the group/class, with the minimum number as small as possible for the group in question, e.g., it is understood that the minimum number of carbon atoms in the group "alkenyl$_{(C\leq 8)}$" or the class "alkene$_{(C\leq 8)}$" is two. Compare with "alkoxy$_{(C\leq 10)}$", which designates alkoxy groups having from 1 to 10 carbon atoms. Also compare "phosphine$_{(C\leq 10)}$", which designates phosphine groups having from 0 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. Typically the carbon number indicator follows the group it modifies, is enclosed with parentheses, and is written entirely in subscript; however, the indicator may also precede the group, or be written without parentheses, without signifying any change in meaning. Thus, the terms "C5 olefin", "C5-olefin", "olefin$_{(C5)}$", and "olefin$_{C5}$" are all synonymous. When any group or compound class below is used with the term "substituted", any carbon atoms of the chemical group replacing the hydrogen atom do not count towards the total carbon atom limit for that group or compound class. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1\text{-}6)}$. Unless specified otherwise, any chemical group or compound class listed in a claim set without a carbon atom limit has a carbon atom limit of less than or equal to twelve.

The term "saturated" when used to modify a compound or an atom means the compound or atom has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system. An aromatic compound or chemical group may be depicted as a single resonance structure; however, depiction of one resonance structure is taken to also refer to any other resonance structure. For example:

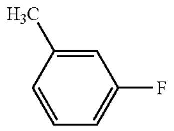

is also taken to refer to

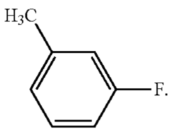

Aromatic compounds may also be depicted using a circle to represent the delocalized nature of the electrons in the fully conjugated cyclic π system, two non-limiting examples of which are shown below:

 and 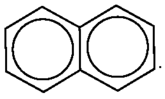.

The term "alkyl" when used without the "substituted" modifier refers to a monovalent saturated aliphatic group with a carbon atom as the point of attachment, a linear or branched acyclic structure, and no atoms other than carbon and hydrogen. The groups —$CH_3$ (Me), —$CH_2CH_3$ (Et), —$CH_2CH_2CH_3$ (n-Pr or propyl), —$CH(CH_3)_2$ (i-Pr, $^{i}$Pr or isopropyl), —$CH_2CH_2CH_2CH_3$ (n-Bu), —$CH(CH_3)CH_2CH_3$ (sec-butyl), —$CH_2CH(CH_3)_2$ (isobutyl), —$C(CH_3)_3$ (tert-butyl, t-butyl, t-Bu or $^{t}$Bu), and —$CH_2C(CH_3)_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —$CH_2$— (methylene), —$CH_2CH_2$—, —$CH_2C(CH_3)_2CH_2$—, and —$CH_2CH_2CH_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =$CH_2$, =$CH(CH_2CH_3)$, and =$C(CH_3)_2$. An "alkane" refers to the compound H—R, wherein R is alkyl as this term is defined above. When these terms are used with the "substituted" modifier one or more hydrogen atom has been independently replaced by —OH, —F, —Cl, —Br, —I, —$NH_2$, —$NO_2$, —$N_2$, —$N_3$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, —$S(O)_2NH_2$, or an amino protecting group. The following groups are non-limiting examples of substituted alkyl groups: —$CH_2OH$, —$CH_2Cl$, —$CF_3$, —$CH_2CN$, —$CH_2C(O)OH$, —$CH_2C(O)OCH_3$, —$CH_2C(O)NH_2$, —$CH_2C(O)CH_3$, —$CH_2OCH_3$, —$CH_2OC(O)CH_3$, —$CH_2NH_2$, —$CH_2N(CH_3)_2$, and —$CH_2CH_2Cl$.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —$CH(CH_2)_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

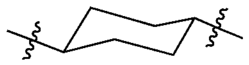 [SMILES: *C1CCC(*)CC1]

is a non-limiting example of cycloalkanediyl group. A "cycloalkane" refers to the compound H—R, wherein R is cycloalkyl as this term is defined above. When these terms are used with the "substituted" modifier one or more hydrogen atom has been independently replaced by —OH, —F, —Cl, —Br, —I, —$NH_2$, —$NO_2$, —$N_2$, —$N_3$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, —$S(O)_2NH_2$, or an amino protecting group.

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen.

Non-limiting examples include: —CH═$CH_2$ (vinyl), —CH═$CHCH_3$, —CH═$CHCH_2CH_3$, —$CH_2$CH═$CH_2$ (allyl), —$CH_2$CH═$CHCH_3$, and —CH═CHCH═$CH_2$. The term "alkenediyl" refers to a divalent unsaturated aliphatic group, with two carbon atoms as points of attachment, a linear or branched acyclic structure, at least one nonaromatic carbon-carbon double bond, no carbon-carbon triple bonds, and no atoms other than carbon and hydrogen. The groups —CH═CH—, —CH═C($CH_3$)$CH_2$—, —CH═$CHCH_2$—, and —$CH_2$CH═$CHCH_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When these terms are used with the "substituted" modifier one or more hydrogen atom has been independently replaced by —OH, —F, —Cl, —Br, —I, —$NH_2$, —$NO_2$, —$N_2$, —$N_3$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —N$(CH_3)_2$, —C(O)$NH_2$, —C(O)$NHCH_3$, —C(O)N$(CH_3)_2$, —OC(O)$CH_3$, —NHC(O)$CH_3$, —S(O)$_2$OH, —S(O)$_2NH_2$, or an amino protecting group.

The term "alkynyl" refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡$CCH_3$, and —$CH_2$C≡$CCH_3$ are non-limiting examples of alkynyl groups. An "alkyne" refers to the class of compounds having the formula H—R, wherein R is alkynyl. When these terms are used with the "substituted" modifier one or more hydrogen atom has been independently replaced by —OH, —F, —Cl, —Br, —I, —$NH_2$, —$NO_2$, —$N_2$, —$N_3$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —N$(CH_3)_2$, —C(O)$NH_2$, —C(O)$NHCH_3$, —C(O)N$(CH_3)_2$, —OC(O)$CH_3$, —NHC(O)$CH_3$, —S(O)$_2$OH, —S(O)$_2NH_2$, or an amino protecting group.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —$C_6H_4CH_2CH_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

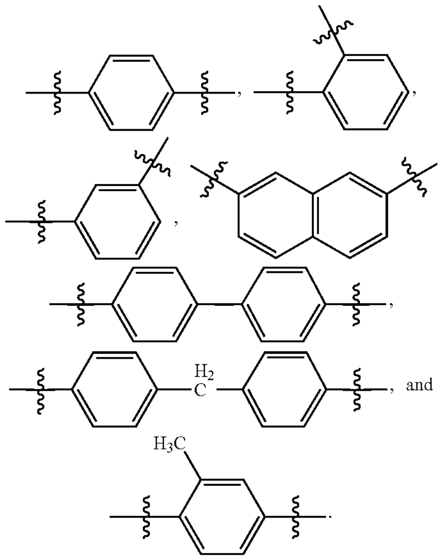

An "arene" refers to the compound H—R, wherein R is aryl as that term is defined above. Benzene and toluene are non-limiting examples of arenes. When these terms are used with the "substituted" modifier one or more hydrogen atom has been independently replaced by —OH, —F, —Cl, —Br, —I, —$NH_2$, —$NO_2$, —$N_2$, —$N_3$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —N$(CH_3)_2$, —C(O)$NH_2$, —C(O)$NHCH_3$, —C(O)N$(CH_3)_2$, —OC(O)$CH_3$, —NHC(O)$CH_3$, —S(O)$_2$OH, —S(O)$_2NH_2$, or an amino protecting group.

The term "aralkyl" refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. Furthermore, one or more of the sulfur atoms present in the group may be oxidized to the sulfonyl or sulfinyl state. If more than one ring is present, the rings may be fused or unfused in a pendent fashion. As used herein, the term does not preclude the presence of one or more alkyl, aryl, and/or aralkyl groups (carbon number limitation permitting) attached to the aromatic ring ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" refers to a divalent aromatic group, with two aromatic carbon atoms, two aromatic nitrogen atoms, or one aromatic carbon atom and one aromatic nitrogen atom as the two points of attachment, said atoms forming part of one or more aromatic ring structures, each with three to eight ring atoms, wherein at least one of the ring atoms of the aromatic ring structure(s) is nitrogen, oxygen or sulfur, and wherein the divalent group consists of no atoms other than carbon, hydrogen, aromatic nitrogen, aromatic oxygen and aromatic sulfur. If more than one ring is present, the rings are fused; however, the term heteroarenediyl does not preclude the presence of one or more alkyl or aryl groups (carbon number limitation permitting) attached to one or more ring atoms. Non-limiting examples of heteroarenediyl groups include:

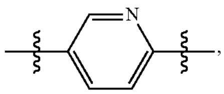,
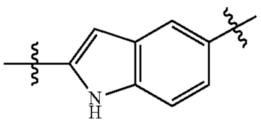
and
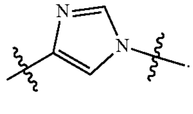

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, $—NH_2$, $—NO_2$, $—N_2$, $—N_3$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, $—S(O)_2NH_2$, or an amino protecting group.

The term "heterocycloalkyl" refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms or an aromatic group fused to the heterocycloalkyl group. Also, the term does not preclude the presence of one or more double bonds in the ring or ring system, provided that the resulting group contains at least one non-aromatic ring system which is the point of attachment. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, $—NH_2$, $—NO_2$, $—N_2$, $—N_3$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, $—S(O)_2NH_2$, or an amino protecting group.

The term "acyl" when used without the "substituted" modifier refers to the group —C(O)R, in which R is a hydrogen, alkyl, cycloalkyl, alkenyl, aryl, aralkyl, heteroaryl, or heterocycloalkyl, as those terms are defined above. The groups, —CHO, $—C(O)CH_3$ (acetyl, Ac), $—C(O)CH_2CH_3$, $—C(O)CH_2CH_2CH_3$, $—C(O)CH(CH_3)_2$, $—C(O)CH(CH_2)_2$, $—C(O)C_6H_5$, $—C(O)C_6H_4CH_3$, $—C(O)CH_2C_6H_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, $—NH_2$, $—NO_2$, $—N_2$, $—N_3$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, $—S(O)_2NH_2$, or an amino protecting group. The groups, $—C(O)CH_2CF_3$, $—CO_2H$ (carboxyl), $—CO_2CH_3$ (methylcarboxyl), $—CO_2CH_2CH_3$, $—C(O)NH_2$ (carbamoyl), and $—CON(CH_3)_2$, are non-limiting examples of substituted acyl groups.

The term "alkoxy" when used without the "substituted" modifier refers to the group —OR, in which R is an alkyl, as that term is defined above. Non-limiting examples include: $—OCH_3$ (methoxy), $—OCH_2CH_3$ (ethoxy), $—OCH_2CH_2CH_3$, $—OCH(CH_3)_2$ (isopropoxy), $—OC(CH_3)_3$ (tert-butoxy), $—OCH(CH_2)_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, $—NH_2$, $—NO_2$, $—N_2$, $—N_3$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, $—S(O)_2NH_2$, or an amino protecting group.

The terms "alkylsulfinyl", "alkylsulfinylamino", "alkylsulfonyl", and "alkylsulfonylamino" refers to the groups —S(O)R, —NHS(O)R, $—S(O)_2R$, and $—NHS(O)_2R$, respectively, in which R is an alkyl, as that term is defined above. The terms above may be used with any other appropriate chemical groups such as "cycloalkylsulfonyl", "alkenylsulfonyl", "alkynylsulfonyl", "arylsulfonyl", "aralkylsulfonyl", "heteroarylsulfonyl", and "heterocycloalkylsulfonyl" wherein R is a cycloalkyl, alkenyl, alkynyl, aryl, aralkyl, heteroaryl, or heterocycloalkyl group, as those terms are defined above.

An "amino acid" is a functional group which contains a —$CO_2H$ and a —$NH_2$ group on the same linear carbon skeleton. In its preferred embodiment, the term "amino acid" refers to one of the naturally occurring or commercially available amino acids as well as their enantiomers and diastereomers. As used herein, the term "amino acid residue" refers to a divalent amino acid which is linked through both the amine group and carboxylate group which are connected by an alkanediyl$_{(C\leq 6)}$ which has been optionally substituted by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —$N(CH_3)_2$, —C(O)$NH_2$, —OC(O)$CH_3$, —NHC(O)$NH_2$, —NHC(NH)$NH_2$, or —$S(O)_2NH_2$ or an alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, or a substituted version of any of these groups wherein one or more hydrogen atoms on the chemical group has been substituted with —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —$N(CH_3)_2$, —C(O)$NH_2$, —OC(O)$CH_3$, —NHC(O)$NH_2$, —NHC(NH)$NH_2$, or —$S(O)_2NH_2$, e.g.,

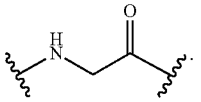

In some embodiments, the amino acid residue is an α-amino acid wherein the alkanediyl is a methylene such that the carbonyl and the amine are joined by a single carbon. The amino acid residue may be one of the canonical amino acids such as leucine, isoleucine, tryptophan, cysteine, methionine, lysine, arginine, serine, threonine, tyrosine, phenylalanine, alanine, glycine, valine, glutamic acid, aspartic acid, asparagine, glutamine, proline, or histidine. These amino acid residues may be protected with one or more protecting groups on either the functional group on the side chain, the amine group, or the carboxylic acid group.

An "amino protecting group" is well understood in the art. An amino protecting group is a group which prevents the reactivity of the amine group during a reaction which modifies some other portion of the molecule and can be easily removed to generate the desired amine Amino protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amino protecting group" can be a divalent protecting group such that both hydrogen atoms on a primary amine are replaced with a single protecting group. In such a situation the amino protecting group can be phthalimide (phth) or a substituted derivative thereof wherein the term "substituted" is as defined above. In some embodiments, the halogenated phthalimide derivative may be tetrachlorophthalimide (TCphth).

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects, or +/−5% of the stated value.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living vertebrate organism, such as a human, monkey, cow, sheep, goat, dog, cat, mouse, rat, guinea pig, bird, fish or transgenic species thereof. In certain embodiments, the patient or subject is a primate. Non-limiting examples of human subjects are adults, juveniles, infants and fetuses.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of the compound of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease, including reactivation.

"Prodrug" means a compound that is convertible in vivo metabolically into an inhibitor according to the present disclosure. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Effective amount," "therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. In some embodiments, treatment of a patient afflicted with one of the pathological conditions described herein comprises administering to such a patient an amount of compound described herein which is therapeutically effective in controlling the condition or in prolonging the survivability of the patient beyond that expected in the absence of such treatment. As used herein, the term "inhibition" of the condition also refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

F. Therapeutic Methods

1. Pharmaceutical Formulations

In particular embodiments, where clinical application of an active ingredient is undertaken, it will be necessary to prepare a pharmaceutical composition appropriate for the intended application. Generally, this will entail preparing a pharmaceutical composition that is essentially free of pyrogens, as well as any other impurities or contaminants that could be harmful to humans or animals. One also will generally desire to employ appropriate buffers to render the complex stable and allow for uptake by target cells.

Aqueous compositions of the present disclosure comprise an effective amount of the active compound, as discussed above, further dispersed in pharmaceutically acceptable carrier or aqueous medium. Such compositions also are referred to as inocula. The phrase "pharmaceutically or pharmacologically acceptable" refers to compositions that do not produce an adverse, allergic or other untoward reaction when administered to an animal, or a human, as appropriate, as well as the requisite sterility for in vivo uses.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present disclosure are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, a controlled release patch, salve or spray. In some embodiments, the topical formulation by used for administration to the skin, to mucosa membranes such as the eye, the eye lids, the genitals, the anus, or the inside of the mouth or nose, or in particular to the cornea.

An effective amount of the therapeutic composition is determined based on the intended goal. The term "unit dose" or "dosage" refers to physically discrete units suitable for use in a subject, each unit containing a predetermined quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment and the potency, stability and toxicity of the particular therapeutic substance.

2. Routes of Administration

Formulations of the present disclosure are suitable for oral administration. However, the therapeutic compositions of the present disclosure may be administered via any common route so long as the target tissue is available via that route. This includes ocular, nasal, buccal, conical, rectal, vaginal, or topical administration, and intradermal, subcutaneous, intramuscular, intraperitoneal or intravenous injection. As such, compositions would be formulated pharmaceutically in route-acceptable compositions that include physiologically acceptable carriers, buffers or other excipients.

As with dosing amounts, the timing of delivery (including intervals and total number of doses) depends on the judgment of the practitioner and are peculiar to each individual. Factors affecting dose include physical and clinical state of the patient, the route of administration, the intended goal of treatment and the potency, stability and toxicity of the particular therapeutic substance.

3. Combination Therapy

In many clinical situations, it is advisable to use a combination of distinct therapies. Thus, it is envisioned that, in addition to the therapies described above, one would also wish to provide to the patient another clinically approved pharmaceutical therapies. Examples of standard therapies are described above. Combinations may be achieved by administering a single composition or pharmacological formulation that includes both agents, or with two distinct compositions or formulations, at the same time, wherein one composition includes the agents of the present disclosure and the other includes the standard therapy. Alternatively, standard therapy may precede or follow the present agent treatment by intervals ranging from minutes to weeks to months. In embodiments where the treatments are applied separately, one would generally ensure that a significant period of time did not expire between the time of each delivery, such that the agents would still be able to exert an advantageously combined effect on the subject. In such instances, it is contemplated that one would administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the agent of the present disclosure, or the standard therapy will be desired. Various combinations may be employed, where the present disclosure compound is "A" and the standard therapy is "B," as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated as well. Drugs suitable for such combinations are described above and include, but are not limited to, herpesvirus DNA polymerase inhibitors (nucleoside analogs), including acyclovir, famciclovir, valaciclovir, penciclovir, and ganciclovir.

Drugs suitable for such combinations in the treatment of a fungal infection include are described above and include, but are not limited to, amphotericin B, an azole anti-fungal compound, echinocandins, or flucytosine. Some non-limiting examples of azole anti-fungal compounds include fluconazole, itraconazole, posaconazole, or voriconazole. It is contemplated that other anti-fungal compounds may be used in combination with the present compounds.

G. Examples

The following examples are included to further illustrate various aspects of the disclosure. It should be appreciated by those of skill in the art that the techniques disclosed in the examples which follow represent techniques and/or compositions discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

1. Materials and Methods

HSV strains and cells used for HSV studies. Vero cells were maintained in Dulbecco's modified Eagle's medium (DMEM) containing 3% newborn calf serum, 3% bovine growth serum, 2 mM L-glutamine and 100 IU/mL penicillin and 0.1 mg/mL streptomycin (P/S). HSV-1 and HSV-2 are de-identified clinical isolates from the Saint Louis University Hospital. Stocks were prepared after a single passage in cell culture and were titered by standard plaque assay (Knipe and Spang, 1982). Wild-type HSV-2 was laboratory strain 333. The TK-deficient mutant of HSV-2 strain 333, ΔTK−, contains a 180-bp KpnI-KpnI deletion in the UL23 open reading frame that abrogates TK activity (McDermott, et al, 1984). ΔTK− was the generous gift of Jim Smiley. Virus stocks were grown and titered on Vero cells (Morrison and Knipe, 1996).

Cells used for toxicity and HBV studies. HepDES19 cells are HepG2 (human hepatoblastoma) a cell line derivatives stably transfected with an HBV genotype D genome under the control of a tetracycline-repressible promoter (Guo et al., 2007). The HepBHAe82 cell line is a HepG2 cell line derivative that has an in-frame HA epitope tag in the N-terminal coding sequence of HBV e antigen (HBeAg) in a transgene that does not disrupt any cis-elements critical for HBV replication, cccDNA transcription, and HA-HBeAg secretion (Cai et al., 2016). Cells were maintained in Dulbecco's modified Eagle's medium (DMEM)/F12 media supplemented with 10% fetal bovine serum (FBS) and 1% penicillin/streptomycin (P/S) with 1 μg/mL tetracycline. Synchronized expression of HBV pgRNA was induced by removing tetracycline from the culture medium.

Cell types used for *C. neoformans* studies. All inhibition assays were performed with *C. neoformans* var. *grubii*, KN99 (serotype A, MAT). Two clinical strains of *C. neoformans* var. *grubii*, serotype A, were provided by Tamara Doering and Andre Spec. Cells were passaged on YPD (1% yeast extract, 2% yeast peptone, 2% dextrose) agar plates and grown overnight at 30° C. in YPD liquid medium prior to diluting for the limiting dilution assays to determine the MIC of inhibition. Cells were diluted to $OD_{650}$ 0.001 in YNB-02 02 (0.67% yeast nitrogen base, 0.2% dextrose, pH 7.0 with 50 mM MOPs)+1% DMSO prior to addition to the plates for the inhibition assays.

Anti-HSV-1 and —HSV-2 replication assay. Compounds to be screened were diluted in PBS supplemented to contain 2% newborn calf serum and 1% glutamine and added in 100 μL volume to confluent cell monolayers in 24-well cluster plates Immediately thereafter HSV-1 and HSV-2, diluted in the supplemented PBS medium, were added to the wells in 50 μl volume such that the final concentration of compound was 50 μM and 5 μM and the multiplicity of infection was 0.1. The plates were incubated at 37° C. for 1 hour and then virus-containing inoculum was removed and the wells were washed once in PBS. Compounds, diluted to 50 μM and 5 μM in DMEM supplemented to contain 2% newborn calf serum and 1% each penicillin/streptomycin, were added at 0.5 mL/well. Plates were incubated at 37° C. an additional 23 hr, and then the plates were visually inspected through a phase contrast microscope for cytopathic effect, and for toxic effect. Only those wells in which the cell monolayer was substantially healthier than the DMSO-treated control wells were harvested, and also a sampling of additional wells which showed cytopathic effect. The entire contents of each well were collected by scraping. Samples were frozen at −80° C., and then subsequently thawed, sonicated, and infectious virus titer was determined by standard plaque assay on Vero cell monolayers. Because the compounds were dissolved at 10 mM in 100% DMSO, equivalent dilutions of DMSO were added to additional wells as a control for effects of the diluent. Each experiment was repeated once. $EC_{50}$ values were determined as above except that serial dilutions of the compound to be tested were prepared starting at 50 or 12.5 μM. The inhibitory values were calculated by non-linear curve-fitting in GraphPad Prism.

HBV replication inhibition studies. HepDES19 cells were seeded in 96-well plates at $4\times10^4$ cells per well in the absence of tetracycline. Test compounds in a final DMSO concentration of 1% were applied to cells 48 hours after induction of HBV replication and cells were incubated with compounds for 72 hours. Cells were washed in 200 μL of phosphate buffered saline (PBS) and lysed in 150 μL of core lysis buffer (10 mM Tris pH 7.4, 1% Tween20, 150 mM NaCl). Cells were incubated at room temperate on an orbital shaker at 350 rpm for 40 minutes. Cell lysate was transferred to a 96 well polymerase chain reaction (PCR) plate and centrifuged at 3300×g for 5 minutes. The supernatant (50 μL) from the cell lysate was transferred to a 96-well PCR plate and mixed with 20 units of micrococcal nuclease and 100 μM $CaCl_2$. The lysate was incubated for 1 hour at 37° C., and then the nuclease was inactivated at 70° C. for ten minutes. Qiagen protease (0.005 Anson units) was added to the lysate and the mixture was incubated overnight. Qiagen protease was then inactivated at 95° C. for ten minutes.

The crude lysate was used as the template for strand-preferential quantitative polymerase chain reaction (q-PCR) analysis. Quantitative PCR was performed with 40 cycles of 95° C. for 15 s and 60° C. for 1 minute employing the Kappa Probe Force universal PCR master mix. The primers and probe (IDT Inc.) for the plus-polarity DNA strand were 5'CATGAACAAGAGATGATTAGGCAGAG3' (SEQ ID NO: 1), 5'GGAGGCTGTAGGCATAAATTGG3' (SEQ ID NO: 2), and 5'/56-FAM/CTGCGCACC/ZEN/AGCACCATGCA/3IABkFQ (SEQ ID NO: 3). The primers and probe for the minus-polarity DNA strand were 5'GCAGATGAGAAGGCACAGA3' (SEQ ID NO: 4), 5'CTTCTCCGTCTGCCGTT3' (SEQ ID NO: 5), and 5'/56-FAM/AGTCCGCGT/ZEN/AAAGAGAGGTGCG/3IABkFQ (SEQ ID NO: 6). $EC_{50}$ values were calculated from the plus-polarity DNA data with GraphPad Prism using the three-parameter log(inhibitor)-versus-response algorithm with the bottom value set to zero.

*C. neoformans* growth inhibition assays. Compounds were tested in a limiting dilution assay with a starting optical density (at 650 nm) of 0.001 in YNB-02 plus 1% DMSO. Cells plus compound were incubated in 96-well clear round bottom plates covered with a Breath-easy® membrane without shaking for 48 hours at 35° C. Before measuring cell density, plates were shaken on a microtiter plate shaker at 900 rpm for 3 minutes to resuspend cells and optical density was measured at 650 nM. The minimal inhibitory concentration (MIC) was determined using compound concentrations from 0.19 to 50 μM of the compound in YNB-02+1% DMSO. Each assay was done in triplicate and all values are the average of two or more independent assays. The data are presented as the average cell density as a percent of DMSO-only treated cells. MICs are reported as the minimal concentration needed to inhibit 80% of *C. neoformans* growth relative to vehicle-treated controls.

Cytotoxicity Assays. Qualitative assessments of cytotoxicity were done visually by inspecting the cells in the primary screening assays. For the quantitative assays, HepDES19 cells were plated in 96-well plates at $1.0\times10^4$ per well. The next day the compounds were added at 0.78 to 100 μM in a final concentration of 1% (v/v) DMSO, and the cells were incubated for 24 hours under conditions identical to those employed for the viral replication inhibition assays. Mitochondrial toxicity was measured by incubating the cells with 0.25 mg/mL thiazolyl blue tetrazolium bromide (MTT, SigmaAldrich Chemical Co.), the cultures were incubated for 60 mM, metabolites were solubilized in acidic isopropanol, and absorbance was read at 570 nm. $CC_{50}$ values were calculated by non-linear curve fitting using GraphPad Prism using the three-parameter variable-response log(inhibitor)-versus-response algorithm with the bottom value set to zero.

Biochemical inhibition of human RNaseH1 activity. Quantitative inhibition of the human RNaseH1 in the biochemical assays was assessed using a molecular beacon assay as described previously (Edwards et al., 2017). Recombinant human RNaseH 1 (0.3 μg) was incubated with 100 nM RNA:DNA substrate, 50 mM HEPES pH 8.0, 100 mM NaCl, 2 mM Tris(2-carboxyethyl)phosphine hydrochloride (TCEP), 0.05% Tween20, 5 units of RNaseOut, test compounds (0 to 500 μM), and 5% DMSO in a 100 μL reaction volume. The substrate was formed by annealing a complementary RNA oligonucleotide to a hairpin DNA oligonucleotide to hold the hairpin DNA oligonucleotide in an open conformation. The DNA oligonucleotide has a 5' fluorescein reporter and a 3' black hole quencher. When the RNA is degraded from the substrate the DNA oligonucleotide closes to form a hairpin structure, decreasing in signal intensity. Reactions were initiated with 5 mM $MgCl_2$ and fluorescence was read using a Synergy HTS multi-mode plate reader at 37° C. Alternatively, the HBV RNaseH version used was MBP-HRHgtCΔ5, a genotype C isolate which lacks the C-terminal 35 amino acids of the HBV RNaseH domain that are predicted to be unstructured. Quantitative inhibition of the human RNaseH1 in biochemical assays was assessed using a FRET-based RNaseH assay under conditions previously reported for an RNaseH molecular beacon assay (Edwards et al., 2017). The heteroduplex substrate was formed by annealing oligonucleotide RHSFS (5'-rGrArUrCrUrGrArGrCrCrUrGrGrGrArGrCrU/6FAM) (SEQ ID NO: 7) to DQ9 (5'-IABkFQ/AGCTCCCAGGCTCAGATC) (SEQ ID NO: 8) (IDT, Inc.) and used at 12.5 nM. Cleavage of the RNA strand released the fluorescein from quenching, increasing fluorescence. Reactions were monitored for 90 min at 37° C. in a plate reader and initial reaction rates were calculated. Reactions contained escalating concentrations of the compounds. 50% inhibitory concentrations ($IC_{50}$) were calculated by non-linear curve fitting using GraphPad Prism.

Molecular modeling and docking. The structure of the HBV RNaseH domain was predicted by homology modeling using a HBV RNaseH genotype C sequence using the Phyre2 server (http://www.sbg.bio.ic.ac.uk/phyre2). The crystal structures of the RNaseH domains of *Escherichia coli* (strain K12) (PDB 1RNH), *Shewanella oneidensis* (strain MR-1) (2E4L), Human immunodeficiency virus type 1, group M, subtype B (isolate BH10) (HIV-1) (5J1E), *Thermus thermophilus* (strain HB8/ATCC 27634/DSM 579) (1RIL), and Ty3 reverse transcriptase (4O8L) were used as homology structural templates. The structure used in the molecular docking studies was based on the Ty3 threading model. The $Mn^{++}$ ions and a reference αHT inhibitor were placed by superimposing the DEDD binding motif of the HBV homology model to that of HIV 1 RNaseH domain bound to β-thujaplicinol (3K2P). The structure of the complex was refined using the Protein Preparation facility of the Maestro program (Schrodinger, LLC).

Compounds were built in Maestro and prepared using the LigPrep facility in their singly and doubly ionized protonation states to facilitate metal binding. Molecular docking of the compounds into the HBV RNaseH homology model was performed using Glide SP (Schrodinger, LLC) with default settings using the position of bound inhibitor as the center of the docking grid and using metal constraints to place the ionized oxygen atoms of the αHT compounds in proximity to the $Mn^{++}$ ions. Docking was also done without the constraint that the compound contact the $Mn^{++}$ ions. Three excluded volume spherical regions were placed to mimic a bound nucleic acid substrate to filter out binding poses in which the inhibitors would clash with the fully-bound substrate (Zhang et al., 2016).

2. Results

These tests were utilized to determine the activity of these compounds. Table 2 shows the activity for those compounds with an amide functionalization. The compounds functionalized with a sulfur containing group are shown in Table 3.

TABLE 2

Amide Containing Compounds in HBV, HSV and *C. neoformans* Models

| ID | $EC_{50}$ (μM) | $CC_{50}$ (μM) | SI ($CC_{50}$/$EC_{50}$) | HBV RNaseH $IC_{50}$ (μM) | HuRH1 $IC_{50}$ (μM) | $SI_{Apparent}$ (huRH1 $IC_{50}$/$EC_{50}$) | HSV-1 suppression 5 μM[b] | HSV-1 suppression 1 μM[b] | HSV-1 suppression 0.33 μM[b] | *C. neoformans* $MIC_{80}$ (μM) |
|---|---|---|---|---|---|---|---|---|---|---|
| 384 | 0.66 ± 0.7 | 17.6 ± 8.9 | 26.8 | 48.0 ± 31.8 | 111 ± 48.8 | 169 | 0.77 | 0.36/0.63/0.09 | | 3.5 |
| 388 | 1.22 ± 1.3 | 19.8 ± 3.0 | 16.2 | 77.6 ± 66.2 | 166 ± 104 | 136 | 0.05 | | | 9 |
| 389 | 0.43 ± 0.2 | 21.2 ± 9.5 | 49.3 | 200 ± 190 | 78.4 ± 47.2 | 182 | 0.43 | | | 5.3 |
| 390 | 0.31 ± 0.1 | 24.9 ± 11.6 | 79.6 | 23.3 ± 9.1 | 106 ± 64.6 | 338 | 0.52 | | | 22 |
| 391 | 0.46 ± 0.2 | 37.5 ± 4.8 | 80.6 | 47.6 ± 0 | 56.1 ± 25.4 | 121 | 0.29 | | | 40 |
| 404 | 0.33 ± 0.2 | 4.5 ± 1.4 | 13.7 | 27.8 ± 11.6 | 14.8 ± 10.1 | 45 | — | | | 9 |
| 539 | 3.17 ± 1.9 | 3.6 ± 1.8 | 1.1 | 98.3 ± 41.9 | 50.0 ± 9.0 | 16 | 5.3/5.28 | 0.52/0.37 | | 4.5 |
| 707 | 0.54 ± 0 | 19.4 ± 8.4 | 36.2 | | 148 ± 22.3 | 277 | −0.18 | — | | 36 |
| 708 | 6.56 ± 5.2 | 22.6 ± 12.8 | 3.4 | 58.7 ± 15.5 | 267 ± 11.7 | 41 | 0.04 | — | | 18 |
| 709 | 4.23 ± 6.5 | 19.5 ± 6.7 | 4.6 | 81.0 ± 28.7 | 84.8 ± 6.7 | 20 | −0.27 | — | | 50 |
| 710 | 4.17 ± 4.1 | 4.5 ± 3.0 | 1.1 | 65.7 ± 18.1 | 32.3 ± 3.2 | 8 | 1.69 | 0.15 | | 2.5 |
| 711 | 0.75 ± 0.3 | 4.6 ± 0.8 | 10.2 | | 184 ± 0 | 247 | 0.32 | — | | 4.5 |
| 712 | 0.77 ± 0.5 | 6.4 ± 0.8 | 8.2 | 47.5 ± 7.9 | 116 ± 67.6 | 150 | 0.36 | — | | 18 |
| 793 | 1.05 ± 0.4 | 18.3 ± 9.8 | 17.4 | 110 ± 10.5 | 178 ± 46.6 | 169 | — | — | | 18 |
| 794 | 7.02 ± 4.7 | 14.7 ± 9.6 | 2.1 | 36.7 ± 14.6 | 48.1 ± 15.4 | 7 | — | — | | 9 |
| 795 | 41.2 ± 39.7 | 12.7 ± 5.5 | 0.3 | 31.3 ± 1.4 | 43.5 ± 14.8 | 1 | — | — | | 9 |
| 796 | 1.1 ± 0.1 | 36.0 ± 24.1 | 32.9 | 25.4 ± 26.3 | 83.3 ± 40.2 | 76 | — | — | | 18 |
| 797 | 0.91 ± 0.3 | 13.9 ± 13.3 | 15.3 | 52.3 ± 8.2 | 44.0 ± 27.1 | 48 | — | — | | 9 |
| 798 | 3.47 ± 0.5 | 3.3 ± 1.8 | 0.9 | 58.3 ± 49.1 | 467 ± 0 | 135 | 4.3949 | 2.3192 | −0.0103 | 1.2 |
| 799 | 3.25 ± 0.8 | 5.3 ± 3.1 | 1.6 | 78.5 ± 60.4 | 713 ± 496 | 219 | 3.8797 | 0.4114 | 0.0848 | 2 |
| 800 | 0.52 ± 0.2 | 16.5 ± 11.4 | 31.8 | 45.6 ± 2.2 | 46.3 ± 10.2 | 89 | — | — | | 26 |
| 801 | 4.9 ± 1.7 | 61.1 ± 22.8 | 12.5 | 603 ± 354 | 833 ± 289 | 170 | — | — | | 50 |
| 802 | 1.19 ± 1.4 | 27.1 ± 31.2 | 22.7 | 85.3 ± 29.9 | 76.5 ± 46.9 | 64 | — | — | | 50 |
| 803 | 1.3 ± 0 | 23.7 ± 22.9 | 18.2 | 158 ± 192 | 36.3 ± 4.0 | 28 | — | — | | 32 |
| 804 | 4.53 ± 0.2 | 30.1 ± 18.0 | 6.6 | 285 ± 226 | 802 ± 397 | 177 | 1.7494 | 0.2922 | 0.1906 | 6.8 |
| 805 | 2.45 ± 0.6 | 19.5 ± 10.8 | 8.0 | 78.7 ± 46.0 | 77.0 ± 30.8 | 31 | — | — | | 9 |
| 806 | 1.8 ± 0.1 | 15.9 ± 6.9 | 8.8 | 122 ± 53.8 | 61.4 ± 15.9 | 34 | — | — | | 4.6 |
| 807 | 1.7 ± 1.0 | 6.0 ± 6.5 | 3.5 | 35.6 ± 38.0 | 799 ± 403 | 470 | 4.5443 | −0.1103 | 0.0714 | 4.5 |
| 808 | 0.48 ± 0.2 | 14.9 ± 8.6 | 31.2 | 24.9 ± 5.5 | 71.9 ± 12.0 | 151 | — | — | | 9 |
| 809 | 1.7 ± 0.5 | 5.8 ± 6.5 | 3.4 | 147 ± 94.1 | 19.6 ± 20.0 | 12 | 4.6892 | 0.02785 | | 3.3 |
| 810 | 0.99 ± 0.5 | 10.9 ± 11.2 | 11.0 | 41.6 ± 9.3 | 41.5 ± 7.2 | 42 | — | — | | 4.5 |
| 834 | 5.3 ± 0.1 | 16.4 ± 11.2 | 3.1 | 83.5 ± 69.3 | 37.2 ± 17.2 | 7 | 1.8 | | | 9 |
| 835 | 5.07 ± 2.5 | 10.3 ± 5.2 | 2.0 | 86.0 ± 42.2 | 725 ± 427 | 143 | 5.23 | — | — | 4.5 |
| 836 | 3.23 ± 0.7 | 5.4 ± 3.5 | 1.7 | 78.9 ± 49.1 | 606 ± 482 | 188 | 5.2 | | | 4.5 |
| 837 | 6.0 ± 2.0 | 8.7 ± 3.4 | 1.5 | 118 ± 88.7 | 625 ± 451 | 104 | 4.09 | — | — | 4.5 |
| 867 | 5.25 ± 1.2 | 5.2 ± 1.3 | 1.0 | 567 ± 474 | 675 ± 563 | 129 | 3.4949 | | | 4.3 |
| 868 | 54.5 ± 4.9 | 100 ± 0 | 1.8 | 40.7 ± 25.4 | 27.7 ± 20.3 | 1 | 0.0414 | −0.15 | | 50 |
| 869 | 13.2 ± 0.6 | 14.6 ± 3.4 | 1.1 | 769 ± 462 | 602 ± 273 | 46 | −0.1472 | | | 9 |
| 870 | 4.2 ± 0.7 | 9.1 ± 2.7 | 2.2 | 76.7 ± 94.4 | 289 ± 296 | 69 | 0.8107 | | | 5 |
| 871 | 1.15 ± 0.4 | 36.6 ± 3.6 | 32.0 | 166 ± 98.8 | 88.2 ± 43.3 | 77 | −0.01925 | −0.1004 | | 50 |
| 872 | 0.84 ± 0.4 | 14.4 ± 3.7 | 17.2 | 42.5 ± 31.2 | 93.0 ± 53.3 | 111 | 0.6435 | −0.1582 | | 20 |
| 873 | 1.43 ± 0.7 | 19.5 ± 8.7 | 13.7 | 46.5 ± 39.5 | 74.7 ± 23.1 | 52 | 0.2004 | −0.1485 | | 20 |
| 874 | 5.75 ± 1.2 | 17.7 ± 6.7 | 3.1 | 597 ± 124 | 52.6 ± 0 | 9 | −0.15 | | | 14 |
| 875 | 1.47 ± 1.5 | 4.7 ± 1.8 | 3.2 | 9.7 ± 4.6 | 17.2 ± 11.0 | 12 | 1.3173 | 0.04485 | | 7 |
| 876 | 0.7 ± 0.4 | 9.2 ± 3.2 | 13.2 | 18.5 ± 5.6 | 39.2 ± 40.6 | 56 | 0.2733 | −0.0739 | | 9 |
| 877 | 0.98 ± 0.5 | 16.5 ± 1.4 | 16.8 | 50.2 ± 21.7 | 34.9 ± 7.2 | 36 | 0.1748 | −0.2318 | | 14 |
| 917 | 1.83 ± 1.3 | 8.9 ± 4.1 | 4.9 | 9.7 ± 3.8 | 30.7 ± 15.8 | 17 | | | | 50 |
| 918 | 1.45 ± 0.4 | 43.8 ± 10.7 | 30.1 | 82.2 ± 25.1 | 127 ± 98.1 | 87 | | | | 50 |
| 919 | 1.08 ± 0.3 | 5.5 ± 1.9 | 5.1 | 1000 ± 0 | 1000 ± 0 | 929 | | | | 2.5 |
| 920 | 1.03 ± 0.3 | 19.3 ± 14.6 | 18.7 | 4.1 ± 2.2 | 40.2 ± 39.7 | 39 | | | | 50 |
| 1016 | 0.9 ± 0 | 24.6 ± 40.0 | 27.4 | 74.1 ± 73.9 | 5.1 ± 2.7 | 6 | | | | 18 |
| 1017 | 5.6 ± 0 | 3.9 ± 1.4 | 0.7 | 122 ± 1.2 | 29.9 ± 10.7 | 5 | | | | 6 |
| 1018 | 2.3 ± 0.3 | 41.2 ± 33.4 | 17.9 | 71.0 ± 21.6 | 129 ± 123 | 56 | | | | 50 |
| 1019 | 5.0 ± 0.4 | 10.7 ± 6.0 | 2.1 | 129 ± 43.3 | 383 ± 471 | 77 | | | | 4.5 |
| 1020 | 2.65 ± 0.4 | 7.8 ± 3.7 | 2.9 | 8.9 ± 0.4 | 12.9 ± 7.3 | 5 | | | | 8 |
| 1021 | 3.05 ± 0.6 | 10.4 ± 7.3 | 3.4 | 17.9 ± 8.8 | 44.0 ± 46.2 | 14 | | | | 4.5 |
| 1039 | 3.35 ± 2.1 | 8.7 ± 2.8 | 2.6 | 33.9 ± 2.8 | 219 ± 87.6 | 65 | | | | 12 |

[a] μM

[b] log10;

—, No effect

TABLE 3

Sulfur Containing Compounds in HBV, HSV and *C. neoformans* Models

| ID | HBV $EC_{50}$[a] | Hu RNaseH $IC_{50}$[a] | $CC_{50}$[a] | HSV-1 suppression 5 μM[b] | HSV-1 suppression 1 μM[b] | HSV-1 suppression 0.33 μM[b] | HSV-2 suppression 5 μM[b] | *C. neoformans* $MIC_{80}$[a] |
|---|---|---|---|---|---|---|---|---|
| 336 | 0.68 | | 45.4 | 1.57/1.44 | 0.35/0.1 | 0.13 | | 50 |
| 337 | 5.73 | | 47.4 | 4.36/2.13 | 1.06/0.42 | 0.28 | | 50 |
| 367 | 16.10 | | 23.0 | 0.49 | 0 | | | 24 |
| 382 | 0.58 | | 79.5 | — | | | | 50 |
| 385 | 4.40 | | 100.0 | 2.50 | | | | 24 |
| 386 | 6.73 | | 68.9 | 0.51 | | | | 24 |
| 387 | 0.41 | | 32.4 | 0.02 | | | | 50 |
| 408 | 11.06 | | 20.4 | 0.56 | — | | | 50 |
| 535 | 2.02 | | 19.2 | 1.02/−0.21 | 0.07 | | | 50 |
| 536 | 50.00 | | 100.0 | 0.35/0.42 | 0.09 | | | 50 |
| 537 | 0.51 | | 20.6 | 0.005/0.88 | 0.25 | | | 50 |
| 538 | 50.00 | | 100.0 | 0.21 | 0.74 | | | 50 |
| 691 | 43.60 | 31.9 | 19.5 | 5.69 | 0.72 | | | 1 |
| 693 | 47.30 | | 13.5 | 5.64 | 0.25 | | | 0.9 |
| 694 | 12.60 | 126.7 | 1.8 | 5.86 | 4.85/5.68 | 4.77/1.87 | | 2 |
| 695 | 26.80 | 130.4 | 21.1 | 2.28 | −0.23 | | | 1.6 |
| 696 | 12.73 | | 9.3 | 5.82 | 0.08 | −0.06 | | 1.4 |
| 697 | 49.10 | | 35.3 | 0.01 | | | — | 49 |
| 698 | 6.18 | 234.5 | 14.8 | 4.85 | −0.35 | −0.31 | | 49 |
| 699 | 6.83 | | 13.1 | 4.39 | 0.2/0.17 | 0.22/0.0147 | | 10 |
| 700 | 49.80 | | 46.0 | 2.01 | 0.57 | 0.49 | | 50 |
| 701 | 7.60 | 46.0 | 63.9 | 0.94 | | | — | 5 |
| 702 | 25.00 | 31.7 | 17.4 | 5.79 | 3.23 | 0.13 | | 0.56 |
| 703 | 10.60 | 49.6 | 8.2 | 5.88 | 4.56/5.94 | 0.73/2.19 | | 6.75 |
| 704 | 52.00 | 24.7 | 21.6 | 5.72 | 0.06 | | | 1.4 |
| 705 | 2.76 | 134.9 | 8.4 | 3.55 | 0.19/0.13 | 0.02/0.19 | | 50 |
| 706 | 51.43 | | 73.0 | 0.59 | | | | 49 |
| 838 | 16.97 | 100.1 | 18.6 | 5.33 | 0.05 | | 5.09 | 1 |
| 839 | 50.00 | 200.8 | 35.1 | 3.21 | −0.1 | | 4.2 | 17 |
| 840 | 50.00 | 72.8 | 21.5 | 3.69/4.26 | 1.52 | 0.2714 | 5.59 | 1 |
| 841 | 10.70 | 1000 | 7.8 | 4.77/5.93 | 4.99 | | | 5 |

[a]μM
[b]log10;
—, No effect

As shown in Tables 2 and 3, these compounds show activity in the inhibition of either or both HSV or HBV.

HBV Inhibition.

$EC_{50}$ values for the amides against HBV replication ranged from 0.31 μM (compound #390) to 54 μM (#868). $CC_{50}$s for the amides ranged from 3.3 μM (#798) to 100 μM (#868), indicating that all but #868 had some detectable cytotoxicity, although it varied from moderate (~<20 μM) to functionally negligible (>50 μM). Therapeutic index values ($CC_{50}/EC_{50}$) for HBV varied from 80 (#390) to 0.3 (#795). TI values less than 1 indicate that the apparent efficacy against HBV replication is due primarily to cytotoxicity, and values from 1-~3.0 indicate that much of the apparent efficacy is likely due to cytotoxicity. There were 40 compounds with TI values >3.0, indicating that 71% of the 57 amides were HBV RNaseH inhibitors.

Inhibition of the human RNaseH1 was measured because it is a likely off-target enzyme that may lead to adverse effects during treatment. Selectivity for HBV replication over RNaseH1 inhibition (human RH1 $IC_{50}$/HBV $EC_{50}$) ranged from 452 (#708) to 0.6 (#868), with 32 of the 36 compounds (89%) for which human RH1 $IC_{50}$s are available having selectivities >10.

The best four amide compounds against HBV by TI value were #390 (TI=95, selectivity=125), 391 (TI=78, selectivity=120), 708 (TI=62, selectivity=452), and 389 (TI=62, selectivity unavailable). Together, these data indicate that the best compounds are strong, specify HBV inhibitors, and that the amide class of α-hydroxytropolones has broad anti-HBV activity.

$EC_{50}$s for the sulfides and sulfones against HBV replication ranged from 0.41 μM (#387) to 52 μM (#704). $CC_{50}$s for the amides ranged from 1.8 μM (#539) to 100 μM (#385, 536, 538), indicating that all but #385, 536, 538 had some detectable cytotoxicity, although it again varied from moderate to functionally negligible. Therapeutic index values ($CC_{50}/EC_{50}$) for HBV varied from 136 (#382) to 0.14 (#694). Using the same cutoff of TI ≥3 as was used for the amide series, there were 10 compounds with TI values >3.0, indicating that 32% of the 31 sulfides and sulfones were HBV RNaseH inhibitors. This is a lower percentage than observed for the amides. This is in part due to the failure of the bi-winged "bis" compounds to inhibit HBV replication, resulting in a larger fraction of the compounds having high HBV $EC_{50}$ values than for the amides.

Selectivity for HBV replication over RNaseH1 inhibition (human RH1 $IC_{50}$/HBV $EC_{50}$) ranged from 452 (#708) to 0.6 (#868), with 32 of the 36 compounds (89%) for which human RNaseH1 $IC_{50}$s are available having selectivities >10. The best four sulfide or sulfone compounds against HBV by TI value were #382 (TI=136), 387 (TI=78), 336 (TI=67), and 537 (TI=41). Selectivity values are unavailable for all four of these compounds. Together, these data indicate that the best compounds are strong, specific HBV inhibitors, and that the sulfide/sulfone class of α-hydroxytropolones can have substantial anti-HBV activity as long as they are not bi-winged "bis" compounds.

HSV Inhibition.

Reduction of HSV-1 titers by incubation of infected cell cultures with amide compounds ranged from undetectable at 5 $\mu$M (e.g. #404) to more than 5 $log_{10}$ plaque forming units (PFU)/ml (e.g. #539). Thirteen compounds suppressed HSV-1 replication by >1.3 $log_{10}$ (>10-fold) at 5 $\mu$M, indicating that the amide class of $\alpha$-hydroxytropolones has broad anti-HSV activity. #798 and #836 continued to suppress HSV-1 replication by >2.3 $log_{10}$ at 1 $\mu$M. All of the amide-containing $\alpha$-hydroxytropolones that strongly suppressed HSV-1 replication had $EC_{50}$s of >1.72 $\mu$M against HBV, and all but #809 and #867 had $IC_{50}$s>100 $\mu$M against Hu RNaseH1, suggesting specificity for inhibition of HSV.

Sulfide and sulfone classes of $\alpha$-hydroxytropolones also showed broad activity against HSV-1. Fifteen compounds suppressed HSV-1 replication by >3 $log_{10}$ at 5 $\mu$M (e.g. #691), and 4 more compounds suppressed replication by >1.4 $log_{10}$. Four of these compounds continued to powerfully suppress replication when added at 1 $\mu$M, and #694 and #841 inhibited HSV-1 replication by >4.7 $log_{10}$ at 0.33 $\mu$M. In total, 59% of the compounds tested showed inhibition of HSV-1, including all bi-sulfides tested and one bi-sulfone compound (#700). All of the compounds with strong anti-HSV activity had $EC_{50}$s>2.7 $\mu$M against HBV. In addition, three compounds that inhibited HSV-1 replication at 5 $\mu$M also inhibited HSV-2 replication, indicating they have the capacity to suppress two highly related herpesviruses.

Together, these data indicate that the best compounds are strong, specific HSV inhibitors, and that in contrast to HBV, the sulfide/sulfone class of $\alpha$-hydroxytropolones can have substantial anti-HSV activity if they are bi-winged "bis" compounds.

C. *Neoformans* Inhibition $MIC_{80}$ values for the amide $\alpha$-hydroxytropolones against *C. neoformans* ranged from 1 to 50 $\mu$M. The TI values were less than 1 for 20 of the amides, suggesting that their efficacy was likely due to general cellular toxicity. Five of the amides (#384, 389, 804, 806 and 809) had a TI >3 suggesting they may be specific *C. neoformans* inhibitors. Eight of the sulfide and sulfone classes of $\alpha$-hydroxytropolones showed strong inhibition of *C. neoformans*, with $MIC_{80}$ values <1 $\mu$M and TI values ranging from 6.7 (#696) to 31 (#702). Three of the compounds with $MIC_{80}$s of 1 $\mu$M or less (#693, 702 and 840) are mono-forms for which the bi-winged "bis" forms (#694, 703 and 841) have both higher $MIC_{80}$ values and increased cytotoxicity. This suggests that the mono-forms of these sulfide derivatives will be more effective *C. neoformans* inhibitors, in contrast to inhibition of HSV or HBV, where the bi-winged "bis" compounds are more effective inhibitors.

Modeling the HBV RNaseH Structure and Compound Docking Studies.

The structure of the HBV RNaseH was predicted using five evolutionarily divergent RNaseHs for which structures are available as templates (from *E. coli, Shewanella oneidensis*, HIV-1, *Thermus thermophilus*, and *Saccharomyces cerevisiae* retrotransposon Ty3). The folds for the N-terminal ~60 amino acids in all five structures were readily superimposable, but only the Ty3 RNaseH fold extended past the C-terminal DEDD residue of the HBV RNaseH active site. The predicted fold based on the Ty3 structure also had the highest confidence score (89%), despite the amino acid identity in the sequence alignment being only 20%. Two $Mn^{++}$ ions were inserted into positions analogous to their locations in the HIV RNaseH, and the model was refined using the Protein Preparation facility of the Maestro program in the Schrodinger suite. The final model (FIG. 1A) included 97 amino acids of the HBV RNaseH domain corresponding to residues 698-794 of the polymerase protein from the reference HBV ADW2 sequence (genotype A). This model comprised all but the N-terminal five and C-terminal 16 residues of the MBP-HRHgtC$\Delta$5 protein used for the biochemical studies.

This predicted model was used to dock the $\alpha$HTs into the HBV RNaseH active site using Glide SP within the Schrodinger suite. Based on the earlier HIV RNase H modeling (Zhang et al., 2016), the docking calculation was set to yield those poses that are less likely to clash with partially bound, but displaced, DNA/RNA duplex substrate in the event that it remained bound to the RT in the enzymatic assay. Compound 120 and all but one of the 57 amide $\alpha$HTs were successfully docked into the RNaseH active site at a pH range of 6-8 (FIGS. 1B-D). Multiple binding poses were often observed for a given molecule, although with only a few exceptions, at least one of the poses had the troponoid oxygen triad chelated to both metals. This was the expected pose based on binding of the $\alpha$HT $\beta$-thujaplicinol to the HIV RNaseH active site (Himmel et al., 2009). In this pose, the appendages are generally directed towards His728, which sits between N751 on one face creating a pocket (s1), and P705 and T706 residues on the other face creating a second pocket (s2). Piperazine-based analogs with distal aromatic appendages (i.e. 404, FIG. 1B) tend to engage pocket s2, facilitating pi-pi stacking with H728. The piperazine linker is similarly positioned to that of the piperidine appendage (390), suggesting that this engagement with H728 happens without distorting the natural conformational preference of the piperazine. The cyclohexyl group of 120 also engages in a similar configuration (FIG. 1C), but the tetrahedral nature of the ketone relative to the planar nature of the amide leads to steric interactions with P705.

Figure 2:
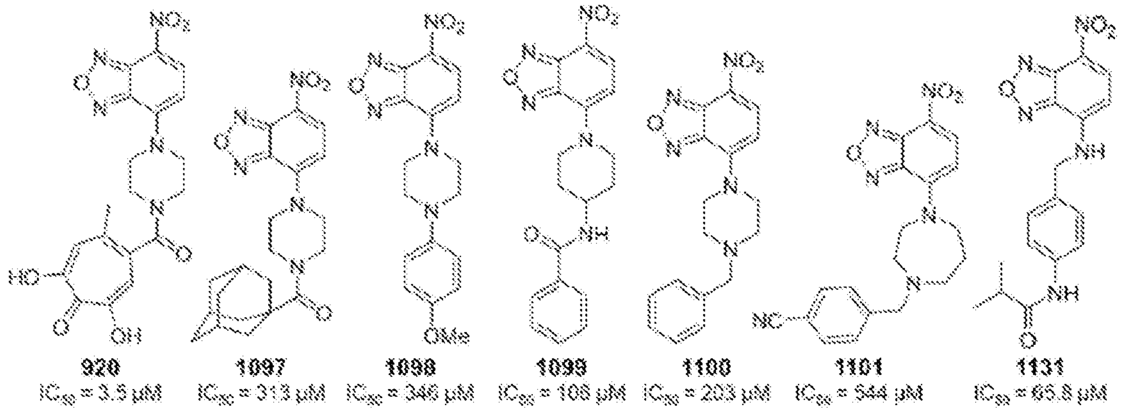
FIG. 2 shows nitrobenzoxadiazol derivatives used to test the alternative binding pose of 390. $IC_{50}$ values are against the HBV RNaseH.

Intriguingly, an inverted binding pose was suggested for 920, in which the nitrobenzoxadiazol group chelates both metal ions in the metalloenzyme core through a similar binding pose and the tropolone OH participates in hydrogen bonding with T706 (FIG. 1D). Significance of this binding pose was tested by purchasing six non-tropolone analogs of 920 and measuring their activity against the HBV RNaseH in biochemical assays. All of the compounds were either inactive or markedly less active than 920 (FIG. 2).

3. Discussions

Leveraging improved synthetic methods, a diverse range of 52 new amide-functionalized $\alpha$HTs were synthesized, and along with five additional molecules previously described, provided 57 amide-containing $\alpha$HTs (Table 2). $EC_{50}$ values for this library ranged from 0.31-54 $\mu$M, with 16 of the 57 amide $\alpha$HTs (28%) having sub-micromolar $EC_{50}$s, seven of which had values below 0.6 $\mu$M. Cytotoxicity was also high for certain members of the library, and $CC_{50}$s ranged from 3.3-100 $\mu$M. Furthermore, while a substantial percentage of molecules had $CC_{50}$ values below 20 $\mu$M, this cytotoxicity did not correlate closely with antiviral activity, and some of the more potent compounds (390, 391, and 389) were among the least cytotoxic ($CC_{50}$ >20 $\mu$M), leading to SI values up to 80.

Without wishing to be bound by any theory, it is believed that the high hit-rate of the amide library compared to previously tested molecules may imply a preference for the amide moiety. Indeed, a dramatic loss in activity is observed by comparing potent piperidine amide 390 ($EC_{50}$=0.31 $\mu$M) with structurally analogous cyclohexyl ketone 120 ($EC_{50}$=3.3 $\mu$M) (Lomonosova et al., 2017). This difference could be the result of amide aryl C—(O) and C—N bonds being more rigid than those of ketones, and thus the entropic penalties for binding may not be as severe. Alternatively, the stronger Lewis basicity of the amide carbonyl or structural differences due to the hybridization of the amide could also be beneficial.

Perhaps due to a similar preference for rigidity, piperazine-based analogs that are close structural homologs to 390 appear to have additional structural advantages. These molecules constitute 35% of the molecules (20 molecules), but over half of the ones with $EC_{50}$ values <0.6 μM (4 of 7 amide αHTs), and 8 of the 16 molecules with sub-micromolar $EC_{50}$s. Furthermore, only three of the piperazine analogs had $EC_{50}$ values >2.0 μM (5%) as compared to 44% (25/57) of the library as a whole. These less-potent molecules included two diaryl analogs (1020 and 1017) with significant steric bulk that could impede target binding, and one with a methylene appendage (1021) whose flexibility might lead to greater entropic penalties. Similarly, amino-acid and benzyl amide-derived αHTs are also flexible classes, and they are mostly less active, with only one of the 16 molecules having a sub-micromolar $EC_{50}$ (797, $EC_{50}$=0.91 μM) and over half (9 of 16, 56%) having $EC_{50}$ values >3 μM. In contrast, aniline is rigid, and 389 and 711 are both sub-micromolar inhibitors. The remaining aniline class is comprised of molecules with additional flexible side-chains, and they are all weaker inhibitors ($EC_{50}$=3.3-6.0 μM).

The amides were also tested for the ability to inhibit the HBV RNaseH in biochemical assays, with $IC_{50}$ values ranging from 4.0-1000 μM. Activity against the RNaseH does not correlate well with replication inhibition, presumably in part due to the need to express the active recombinant enzyme as a fragment of the larger HBV polymerase protein that carries the RNaseH activity (Edwards et al., 2019). Consequently, the HBV RNaseH $IC_{50}$ values must be viewed only semi-quantitatively. However, the data do support some broader conclusions. First, only 1 of the 17 molecules that had $IC_{50}$ values >100 μM had an $EC_{50}$ against viral replication <1 μM. Second, the piperidine amides were among the best compounds in both the enzymatic assay and in the cell-based replication inhibition assays. For example, 13 of 20 (65%) piperidine amides had $IC_{50}$ values <50 μM, as compared to 28% of the remaining library, and all 5 molecules with $IC_{50}$ values under 20 μM were piperidine amides. However, within the piperazine-based amide series, there was no correlation between $IC_{50}$ and $EC_{50}$ values.

A homology model of HBV RNaseH was developed by threading against the Ty3 RNaseH structure (FIG. 1). Two $Mn^{++}$ ions were readily accommodated in the model in positions analogous to their binding to the HIV RNaseH, and the active site was shallow, again in agreement with the structure of the HIV enzyme (Himmel et al., 2009). Docking of the amide αHTs into the model often revealed several binding poses per each molecule, although in virtually all cases, one of these poses had the troponoid oxygen triad chelated to both metals. This is consistent with crystal structures of αHTs bound to related dinuclear metalloenzymes such as the HIV RT RNaseH (Himmel et al., 2009), and the observation that ablating the oxygen trident on the αHT eliminates inhibition of HBV replication (Cai et al., 2014; Lu et al., 2015). A possible inverted binding pose was revealed for 920 in which the nitrobenzoxadiazol moiety chelates the cations. Five of the six non-troponoid 920 analogs detectably inhibited the RNaseH ($IC_{50}$ <500 μM), and 1131 that was selected based on potential interactions with T706 was the only analog with an $IC_{50}$ <100 μM. Therefore, this inverted pose appears likely to be real but to contribute only modestly to efficacy of 920. (FIG. 2). However, there was only a very weak correlation for the amide compounds between docking score and HBV RNaseH $IC_{50}$s, and almost no correlation with efficacy against viral replication. Therefore, the model appears to reveal general aspects of the compounds' binding poses, but it cannot yet identify details of their interactions with the enzyme.

This metal-chelating mechanism is very similar to that used by the HIV integrase inhibitors Bictegravir, Dolutegravir, Elvitegravir, and Raltegravir. In addition, the Influenza Virus PA cap-snatching endonuclease inhibitor Baloxavir marboxil was recently approved by the FDA (Yang, 2019). Baloxavir inhibits the PA endonuclease using the same metal chelating mechanism that the αHTs presumably use against the HBV RNaseH (Omoto et al., 2018). Furthermore, the US Food and Drug Administration had approved 62 drugs that act by coordinating active-site cations in metalloenzymes as of 2017 (Chen et al., 2019). Therefore, the metal chelation mechanism employed by HBV RNaseH inhibitors is a well-established drug mechanism, and the challenges to HBV drug development are the normal ones of achieving adequate efficacy and selectivity while maintaining suitable pharmacological parameters.

Selectivity will be important to establish for compounds that act by metal chelation due to the large number of enzymes in cells with divalent cations in their active sites. Unfortunately, the semi-quantitative nature of the HBV RNaseH assay prevents rigorous calculation of biochemical selectivity indexes. The limited observations possible reveal that the HBV RNaseH $IC_{50}$ values correlate only weakly with those of huRH1 ($R^2$=0.0.34), and that the semi-quantitative selectivity indexes for human vs. HBV RNaseH $IC_{50}$s range from 14-fold more potent for huRH1 (867), to 22-fold more potent for the HBV RNaseH (808). The best available quantitative assessment of selectivity is an apparent selectivity index that compares $EC_{50}$s for HBV replication inhibition to $IC_{50}$s against HBV huRH1 ($SI_{apparent}$= $IC_{50\ huRH1}/EC_{50\ HBV\ replication}$). $SI_{apparent}$ values averaged 105 and ranged from 1 to >900, with 43 compounds having values ≥20. Therefore, biochemical selectivity against huRH1 is present.

Additional perspective on selectivity was obtained by evaluating the activity of the amide αHTs against growth of the fungus *C. neoformans* and two bacteria, *E. coli* and *S. aureus*, and by considering the SIs in human cells (Table 2). Forty-nine of the 57 αHTs detectably inhibited *C. neoformans* ($MIC_{80}$ <50 μM), with an average $MIC_{80}$ value of 17 μM, and over half of the molecules (33) had values <10 μM. However, the *C. neoformans* SAR was distinct from that against HBV replication. Activity against *C. neoformans* heavily favored the benzyl amide-derivative series, with all but a single molecule having an $MIC_{80}$ less than 6 μM. On the other hand, the piperazine-derived analogs that seemed privileged for activity against HBV replication were considerably less potent against *C. neoformans*, with only one from this series having an $MIC_{80}$ <6 μM. The library was largely inactive against the bacteria, with only 8 of the 57 amide αHTs having measurable $MIC_{80}$s against either *E. coli* or *S. aureus* and the lowest $MIC_{80}$ being 30 μM for 710 vs. *E. coli*. The failure of the amide αHTs to inhibit bacterial growth is not a general feature of the αHTs because other troponoid subclasses can enter cells and inhibit bacterial growth with $MIC_{80}$ values as low as 9 μM against *E. coli* (Cao et al., 2018). Finally, the SI values for HBV replication vs. cytotoxicity in cell culture are affected by the sum of the off-target effects on cells. SIs for the amide αHTs average 18

(range 0.3-80). Although some of the amide αHTs were clearly cytopathic, 26 of 57 (46%) compounds had SIs >10.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

F. References

The following references, to the extent that they provide exemplary procedural or other details supplementary to those set forth herein, are specifically incorporated herein by reference:

Abu-Raddad, *PLoS One,* 3:e2230, 2008.
Andrei and Snoeck, *Curr Opin Infect Dis.* 26:551-560, 2013.
Ariyoshi et al., *Cell* 78:1063-1072, 1994.
Arvin & Gilden, *Varicella-Zoster Virus,* 2015-2057, 2013.
Balzarini et al., *PLoS Pathog.* 9:e1003456, 2013.
Bernstein et al., *Antiviral Res* 92:386-388, 2011.
Boehmer & Lehman, *Ann. Rev. Biochem.,* 66:347-384, 1997
Bratton et. al., *PLoS One.* 7:e43582, 2012.
Bratton et. al., *Antimicrob Agents Chemother.* 57:2485-2495, 2013.
Brizendine et. al., *PLoS One.* 8:e60431, 2013.
Byrnes et. al., *PLoS Pathog.* 6:e1000850, 2010.
Byrnes et. al., *Microbes Infect.* 13:895-907, 2011.
Cai et al., *Antivir. Res.,* 108:48-55, 2014.
Cai et al., *Antivir. Res.,* 132:26-37, 2016.
Cao et al., *ACS Omega,* 3:15125-15133, 2018.
Chen et al., *J. Neurovirology* 8:204-210, 2002.
Chen et al., *Chem. Rev.,* 119:1323-1455, 2019.
Chenier, Can. *Vet. J.,* 45:241-243, 2004.
Damania & Cesarman, *Kaposi's Sarcoma-Associated Herpesvirus,* 2080-2128, 2013.
Dana et. al., *Emerg Infect Dis.* 15:1185-1191, 2009.
Drew et al., *Clin Diagn Virol.* 1:179-185, 1993.
Drew et al., *J Infect Dis.* 179:1352-1355, 1999.
Drew et al., *Am J Transplant* 1:307-312, 2001.
Dolan et al., *J Virol* 72:2010-2021, 1998.
Duan, *J. Infect. Dis.,* 198:659-663, 2008.
Edwards et al., *Antivir. Res.,* 143:205-207, 2017.
Edwards et al., *Antivir. Res.,* 164:70-80, 2019.
Field & Vere Hodge, *Br. Med. Bull.,* 106:213-249, 2013.
Fortier et al., *Veterinary J.* 186:148-156, 2010.
Frank et al., *Biol. Chem.* 379:1407-1412, 1998.
Frank et al., *Proc. Natl. Acad. Sci. USA* 95:12872-12877, 1998.
Freeman, *AIDS,* 20:73-83, 2006.
Frobert et al., *Antivir. Res.,* 111:36-41, 2014.
Gerelsaikhan et al., *J. Virol.* 70, 4269-4274, 1996.
Goebels et. al., *PLoS Genet.* 9:e1003686, 2013.
Goedken et al., *J. Biol. Chem.* 276, 7266-7271, 2001.
Guo et al., *J. Virol.,* 81:12472-12484.
Hanson et al., *Viruses* 3(11): 2160-2191, 2011.
Himmel et al., *Structure,* 17:1625-1635, 2009.
Hostomsky et al., *Nulceases*, vol. 2, 1993b.
Hostomsky et al., "Ribonuclease H," in: Linn, S. M., Lloyd, R. S., Roberts, R. J. (Eds.), Nucleases. Cold Spring Harbor Laboratory Press, Plainview, NY, pp. 341-376, 1993a.
Hostomsky et al., *Structure* 3:131-134, 1993c.
Hu et al., *Antivir. Res.,* 99:221-229, 2013.
Imai et al., *J Infect Dis.* 189:611-615, 2004.
Janbon et. al., *PLoS Genet.* 10:e1004261, 2014.
Johnston, *Lancet,* 379:641-647, 2012.
Ianiri et. al., *mBio.* 6:e02334-14, 2015
Katayanagi et al., *Nature* 347: 306-309, 1990.
Keck et al., *J. Biol. Chem.* 273, 34128-34133, 1998.
King, *J. Amer. Acad. Dermatol.,* 18:176-179, 1988.
Klumpp et al., *Nucleic Acids Res.* 31, 6852-6859, 2004.
Kwun et al., *J. Gen. Virol.* 82, 2235-2241, 2001.
Lai et al., *Structure* 8:897-904, 2000.
Leisgang, *Cornea,* 20:1-13, 2001.
Lima et al., *Methods Enzymol.* 341:430-440, 2001.
Lockhart et. al., *PLoS One.* 8:e74737, 2013.
Lomonosova et al., *Antivir Res.,* 144: 164-172, 2017.
Long et al., *Antivir. Res.,* 149:41-47, 2018.
Longnecker et al., *Epstein-Barr Virus,* 1898-1959, 2013.
Lortholary, *Clin Infect Dis.* 45:81-83, 2007.
Lu et al., *Antimicrob. Agents Chemother.,* 59:1070-1079, 2015.
Lu et al., *Antivir. Res.,* 135:24-34, 2016.
Marfori et al., *J Clin Virol.* 38:120-5, 2007.
McDermott et al., *J Virol,* 51:747-753, 1984.
McKenney et. al., *MMWR Morbidity and Mortality Weekly Report.* 63:585-587, 2014.
Mdodo et. al., *East Afr Med J.* 87:481-487, 2010.
Meck et al., *Med. Chem. Comm.,* 5:842-852, 2014.
Mettenleiter et al., *Virus Res.* 143:222-234, 2009.
Mirza et. al., *Clin Infect Dis.* 36:789-794, 2003.
Morfin and Thouvenot, *J Clin Virol.,* 26:29-37, 2003.
Morrison and Knipe, *Virology,* 220:402-413, 1996.
Nandi et al., *Animal health research reviews/Conference of Research Workers in Animal,* 2009.
Nowotny et al., *Cell* 121: 1005-1016, 2005.
Nowotny, *EMBO Rep.* 10:144-151, 2009.
Omoto et al., *Lancet. Gastroenterol. Hepatol.,* 3:383-403, 2018.
Parker et al., *EMBO J.* 23: 4727-4737, 2004.
Pellet & Roizman, *Herpesviridae* 1802-1822, 2013.
Pfaller et. al., *Antimicrob Agents Chemother.* e00246-16, 2017.
Prichard et al., *Antimicrob. Agents Chemother.* 55:4728-4734, 2011.
Pyrgos et. al., *PLoS One.* 8:e56269, 2013.
Quenelle et al., *Antivir Chem Chemother* 22:131-137, 2011.
Quinlan et al., *Cell* 36:857-868, 1984.
Roizman et al., *Herpes Simplex Viruses,* 1823-1897, 2013.
Roperto, *J. Comp. Pathol.,* 122:298-302, 2000.
Schumacher et al., *PLoS Pathog.,* 8:e1002862, 2012
Selvarajan et al., *J Virol.,* 87:7140-7148, 2013
Sloan et. al., *Clinical Epidemiology,* 6:169-182, 2014.
Smith et al., *J. Virol.* 68, 5721-5729, 1994.
Song et al., *Science* 305: 1434-1437, 2004.
Springer et. al., *PLoS Pathog.* 10:e1004285, 2014.
Tavis et al., *PLoS Pathogens* 9:e1003125, 2013.
Van Velzen, *J. Infect. Dis.,* 208:1359-1365, 2013.
Vere Hodge & Field, *Adv. Pharmacol.,* 67:1-38, 2013.
Wald et al., *N Engl J Med.* 370:201-210, 2014.
Wang et al., *J. Virol.* 79:14079-14087, 2005.
Wang et al., *J Clin Virol,* 52:107-112, 2011.

Weller & Coen, *Cold Spring Harbor Perspectives in Biology* 4:a013011, 2012.
Weller and Kuchta, *Expert Opin Ther Targets,* 17:1119-1132, 2013.
Yamanishi et al., *Human Herpesviruses* 6 and 7, p. 2058-2079, 2013.
Yan et al., *MBio* 5:e01318-14, 2014.
Yang et al., *Science* 249: 1398-1405, 1990.
Yang and Steitz, *Structure,* 3, 131-134, 1995.
Yao et al., *Antimicrob Agents Chemother.* 58:2807-2815, 2014.
Zhang et al., *ACS Omega,* 1:435-447, 2016.
Zhou et al., *J Virol.* 88:11121-11129, 2014.

What is claimed:

1. A compound of the formula:

(I)

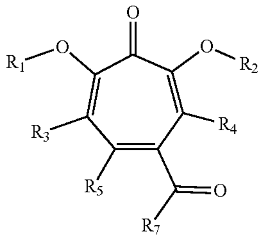

wherein:

$R_1$ and $R_2$ are each independently hydrogen, alkyl$_{(C\leq8)}$, substituted alkyl$_{(C\leq8)}$, acyl$_{(C\leq8)}$, or substituted acyl$_{(C\leq8)}$;

$R_3$ and $R_4$ are each independently hydrogen, halo, hydroxy, alkyl$_{(C\leq8)}$, substituted alkyl$_{(C\leq8)}$, aryl$_{(C\leq12)}$, or substituted aryl$_{(C\leq12)}$;

$R_5$ is hydrogen, alkyl$_{(C\leq8)}$, substituted alkyl$_{(C\leq8)}$, aryl$_{(C\leq12)}$, or substituted aryl$_{(C\leq12)}$; and $R_7$ is an amino acid residue, heterocycloalkyl$_{(C\leq12)}$, substituted heterocycloalkyl$_{(C\leq12)}$, —N($R_8$)$R_9$, wherein:

$R_8$ is hydrogen, alkyl$_{(C\leq8)}$, substituted alkyl$_{(C\leq8)}$; and $R_9$ is alkyl$_{(C4-8)}$, substituted alkyl$_{(C4-8)}$, alkynyl$_{(C\leq12)}$, aryl$_{(C\leq12)}$, aralkyl$_{(C\leq18)}$, heteroaryl$_{(C\leq12)}$, heteroaralkyl$_{(C\leq18)}$, or a substituted version thereof; or —$Y_1$—$R_a$, wherein:

$Y_1$ is alkanediyl$_{(C\leq12)}$, arenediyl$_{(C\leq12)}$, or a substituted version of either group;

$R_a$ is aralkyl$_{(C\leq12)}$, heterocycloalkyl$_{(C\leq12)}$, aralkoxy$_{(C\leq12)}$, -aralkyl$_{(C\leq12)}$-heterocycloalkyl$_{(C\leq8)}$, or a substituted version thereof; or a group of the formula:

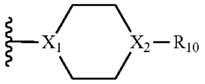

wherein:

$X_1$ and $X_2$ is C or N;

$R_{10}$ is alkyl$_{(C\leq12)}$, cycloalkyl$_{(C\leq12)}$, aryl$_{(C\leq12)}$, heteroaryl$_{(C\leq12)}$, aralkyl$_{(C\leq18)}$, acyl$_{(C\leq12)}$, heteroarenediyl$_{(C\leq12)}$-heteroaryl$_{(C\leq12)}$, —C(O)-diarylamino$_{(C\leq12)}$, —C(O)-heteroaryl$_{(C\leq12)}$, alkylsulfonyl$_{(C\leq12)}$, arylsulfonyl$_{(C\leq12)}$, heteroarylsulfonyl$_{(C\leq12)}$, alkylsulfonyl amino$_{(C\leq12)}$, or a substituted version of any of these groups; an amino protecting group; or a compound of the formula:

(II)

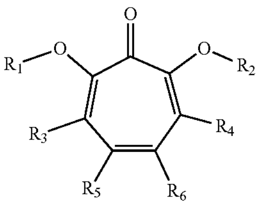

wherein:

$R_1$ and $R_2$ are each independently hydrogen, alkyl$_{(C\leq8)}$, substituted alkyl$_{(C\leq8)}$, acyl$_{(C\leq8)}$, or substituted acyl$_{(C\leq8)}$;

$R_3$ is —S(O)$_x$$R_b$, wherein:

x is 0, 1, or 2;

$R_b$ is hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups;

$R_4$ is hydrogen, alkyl$_{(C\leq8)}$, substituted alkyl$_{(C\leq8)}$, —S(O)$_y$$R_c$, wherein:

y is 0, 1, or 2;

$R_c$ is hydrogen or alkyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, or a substituted version of any of these groups; and $R_5$ and $R_6$ are each independently hydrogen, alkyl$_{(C\leq 8)}$, substituted alkyl$_{(C\leq 8)}$, aryl$_{(C\leq 12)}$, substituted aryl$_{(C\leq 12)}$, acyl$_{(C\leq 8)}$, or substituted acyl$_{(C\leq 8)}$;

provided that the compound is not a compound of the formula:

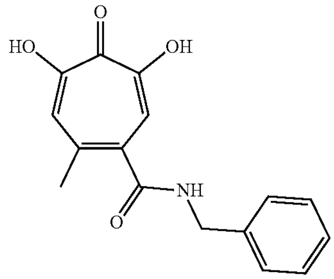

,

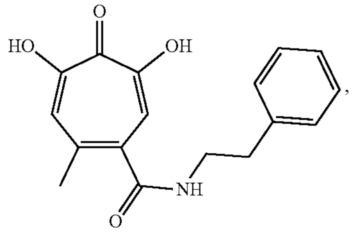

,

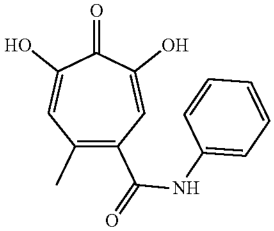

,

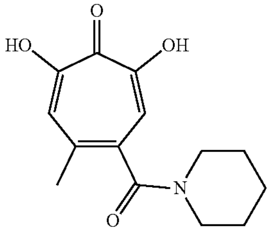

,

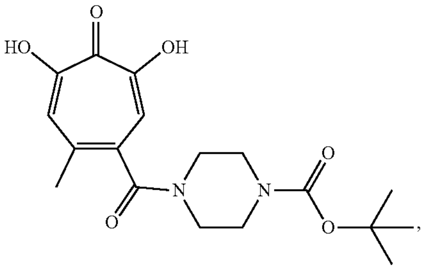

,

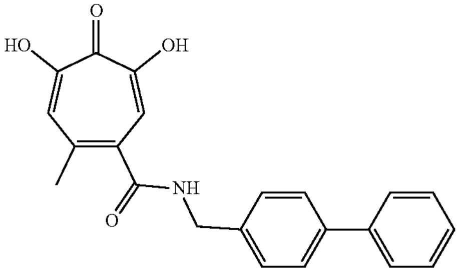

, or

-continued

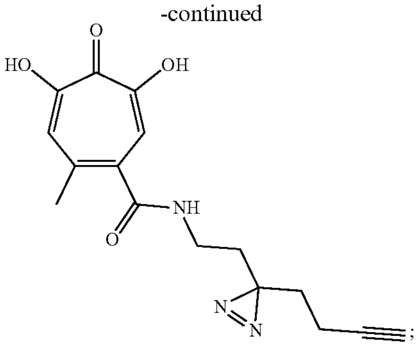

;

or a pharmaceutically acceptable salt thereof.

2. The compound of claim 1 further defined as:

(I)

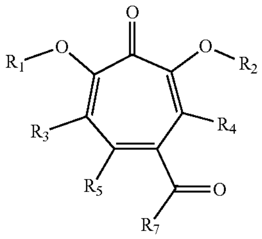

wherein:

$R_1$ and $R_2$ are each independently hydrogen, alkyl$_{(C\leq 8)}$, substituted alkyl$_{(C\leq 8)}$, acyl$_{(C\leq 8)}$, or substituted acyl$_{(C\leq 8)}$;

$R_3$ and $R_4$ are each independently hydrogen, halo, hydroxy, alkyl$_{(C\leq 8)}$, substituted alkyl$_{(C\leq 8)}$, aryl$_{(C\leq 12)}$, or substituted aryl$_{(C\leq 12)}$;

$R_5$ is hydrogen, alkyl$_{(C\leq 8)}$, substituted alkyl$_{(C\leq 8)}$, aryl$_{(C\leq 12)}$, or substituted aryl$_{(C\leq 12)}$; and $R_7$ is an amino acid residue, heterocycloalkyl$_{(C\leq 12)}$, substituted heterocycloalkyl$_{(C\leq 12)}$, —N($R_8$)$R_9$, wherein:

$R_8$ is hydrogen, alkyl$_{(C\leq 8)}$, substituted alkyl$_{(C\leq 8)}$; and $R_9$ is alkyl$_{(C4-8)}$, substituted alkyl$_{(C4-8)}$, alkynyl$_{(C\leq 12)}$, aryl$_{(C\leq 12)}$, aralkyl$_{(C\leq 18)}$, heteroaryl$_{(C\leq 12)}$, heteroaralkyl$_{(C\leq 18)}$, or a substituted version thereof; or —$Y_1$—$R_a$, wherein:

$Y_1$ is alkanediyl$_{(C\leq 12)}$, arenediyl$_{(C\leq 12)}$, or a substituted version of either group;

$R_a$ is aralkyl$_{(C\leq 12)}$, heteroaryl$_{(C\leq 12)}$, heterocycloalkyl$_{(C\leq 12)}$, aralkoxy$_{(C\leq 12)}$, -aralkyl$_{(C\leq 12)}$-heterocycloalkyl$_{(C\leq 8)}$, or a substituted version thereof; or a group of the formula:

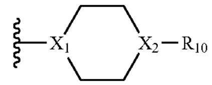

wherein:

$X_1$ and $X_2$ is C or N;

$R_{10}$ is cycloalkyl$_{(C\leq 12)}$, aryl$_{(C\leq 12)}$, heteroaryl$_{(C\leq 12)}$, aralkyl$_{(C\leq 18)}$, acyl$_{(C\leq 12)}$, heteroarenediyl$_{(C\leq 12)}$-heteroaryl$_{(C\leq 12)}$, —C(O)- diarylamino$_{(C\leq12)}$, —C(O)-heteroaryl$_{(C\leq12)}$, alkylsulfonyl$_{(C\leq12)}$, heterocycloalkyl sulfonyl$_{(C\leq12)}$, alkylsulfonylamino$_{(C\leq12)}$, or a substituted version of any of these groups; an amino protecting group; or or a pharmaceutically acceptable salt thereof.

3. The compound of claim 1 further defined as:

(IV)

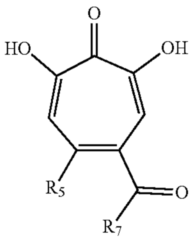

wherein:

$R_5$ is hydrogen, alkyl$_{(C\leq8)}$, substituted alkyl$_{(C\leq8)}$, aryl$_{(C\leq12)}$, or substituted aryl$_{(C\leq12)}$; and $R_7$ is an amino acid residue, heterocycloalkyl$_{(C\leq12)}$, substituted heterocycloalkyl$_{(C\leq12)}$, —N($R_8$)$R_9$, wherein:

$R_8$ is hydrogen, alkyl$_{(C\leq8)}$, substituted alkyl$_{(C\leq8)}$); and $R_9$ is alkyl$_{(C4-8)}$, substituted alkyl$_{(C4-8)}$, alkynyl$_{(C\leq12)}$, aryl$_{(C\leq12)}$, aralkyl$_{(C\leq18)}$, heteroaryl$_{(C\leq12)}$, heteroaralkyl$_{(C\leq18)}$, or a substituted version thereof; or —$Y_1$—$R_a$, wherein:

$Y_1$ is alkanediyl$_{(C\leq12)}$, arenediyl$_{(C\leq12)}$, or a substituted version of either group;

$R_a$ is aralkyl$_{(C\leq12)}$, heteroaryl$_{(C\leq12)}$, heterocycloalkyl$_{(C\leq12)}$, aralkoxy$_{(C\leq12)}$, -aralkyl$_{(C\leq12)}$-heterocycloalkyl$_{(C\leq8)}$, or a substituted version thereof; or a group of the formula:

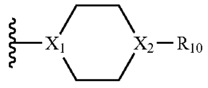

wherein:

$X_1$ and $X_2$ is C or N;

$R_{10}$ is cycloalkyl$_{(C\leq12)}$, aryl$_{(C\leq12)}$, heteroaryl$_{(C\leq12)}$, aralkyl$_{(C\leq18)}$, acyl$_{(C\leq12)}$, heteroarenediyl$_{(C\leq12)}$-heteroaryl$_{(C\leq12)}$, —C(O)-diarylamino$_{(C\leq12)}$, —C(O)-heteroaryl$_{(C\leq12)}$, alkylsulfonyl$_{(C\leq12)}$, heterocycloalkyl sulfonyl$_{(C\leq12)}$, alkylsulfonylamino$_{(C\leq12)}$, or a substituted version of any of these groups; an amino protecting group; or or a pharmaceutically acceptable salt thereof.

4. The compound of claim 1 further defined as:

(II)

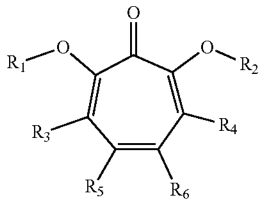

wherein:

$R_1$ and $R_2$ are each independently hydrogen, alkyl$_{(C\leq8)}$, substituted alkyl$_{(C\leq8)}$, acyl$_{(C\leq8)}$, or substituted acyl$_{(C\leq8)}$;

$R_3$ is —S(O)$_x$$R_b$, wherein:

x is 0, 1, or 2;

$R_b$ is hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups;

$R_4$ is hydrogen, alkyl$_{(C\leq8)}$, substituted alkyl$_{(C\leq8)}$, —S(O)$_y$$R_c$, wherein:

y is 0, 1, or 2;

$R_c$ is hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups; and $R_5$ and $R_6$ are each independently hydrogen, alkyl$_{(C\leq8)}$, substituted alkyl$_{(C\leq8)}$, aryl$_{(C\leq12)}$, substituted aryl$_{(C\leq12)}$, acyl$_{(C\leq8)}$, or substituted acyl$_{(C\leq8)}$;

or a pharmaceutically acceptable salt thereof.

5. The compound of claim 1 further defined as:

(VI)

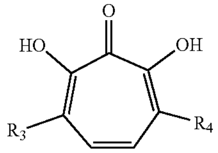

wherein:

$R_3$ is —S(O)$_x$$R_b$, wherein:

x is 0, 1, or 2;

$R_b$ is hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups;

$R_4$ is hydrogen, alkyl$_{(C\leq8)}$, substituted alkyl$_{(C\leq8)}$, —S(O)$_y$$R_c$, wherein:

y is 0, 1, or 2;

$R_c$ is hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups; and or a pharmaceutically acceptable salt thereof.

6. The compound of claim 1, wherein $R_3$ is —S(O)$_x$$R_b$, wherein:

x is 0 or 2; and $R_b$ is hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups.

7. The compound of claim 6, wherein $R_b$ is alkyl$_{(C\leq12)}$ or substituted alkyl$_{(C\leq12)}$.

8. The compound of claim 6, wherein $R_b$ is aryl$_{(C\leq12)}$ or substituted aryl$_{(C\leq12)}$.

9. The compound of claim 1, wherein $R_4$ is —$S(O)_xR_b$, wherein:

x is 0 or 2; and $R_b$ is hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups.

10. The compound of claim 9, wherein $R_b$ is alkyl$_{(C\leq12)}$ or substituted alkyl$_{(C\leq12)}$.

11. The compound of claim 9, wherein $R_b$ is aryl$_{(C\leq12)}$ or substituted aryl$_{(C\leq12)}$.

12. The compound of claim 1, wherein $R_5$ is hydrogen, alkyl$_{(C\leq8)}$, or substituted alkyl$_{(C\leq8)}$.

13. The compound of claim 1, wherein $R_7$ is an amino acid residue, —$N(R_8)R_9$, or

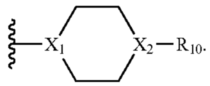

14. The compound of claim 13, wherein $R_9$ is aryl$_{(C\leq12)}$, substituted aryl$_{(C\leq12)}$, heteroaryl$_{(C\leq12)}$, substituted heteroaryl$_{(C\leq12)}$, aralkyl$_{(C\leq18)}$, substituted aralkyl$_{(C\leq18)}$, or —$Y_1$—$R_a$; or $R_{10}$ is aryl$_{(C\leq12)}$, substituted aryl$_{(C\leq12)}$, heteroaryl$_{(C\leq12)}$, or substituted heteroaryl$_{(C\leq12)}$.

15. The compound of claim 1, wherein the compound is further defined as:

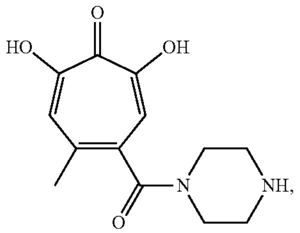

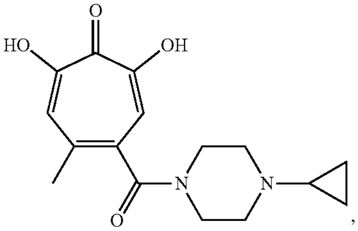

,

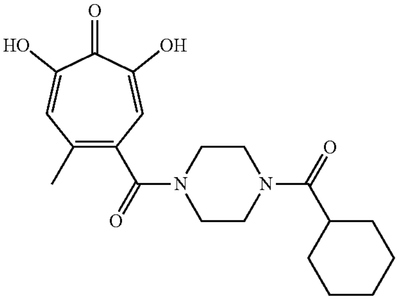

,

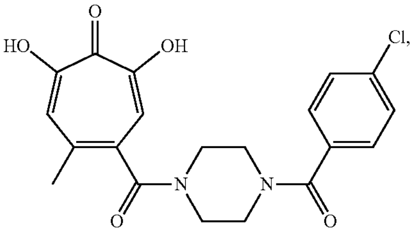

-continued

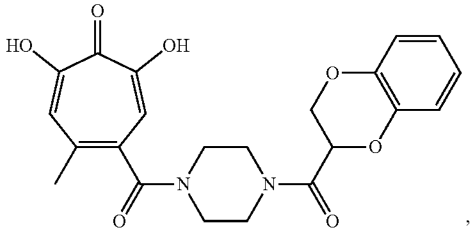

,

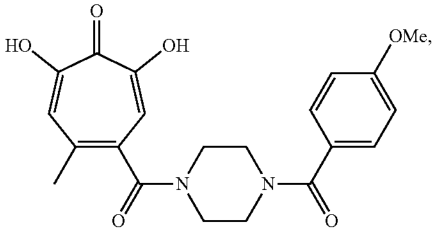

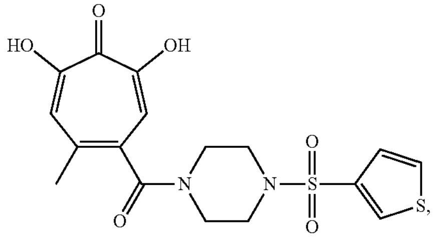

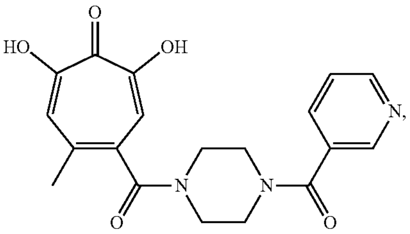

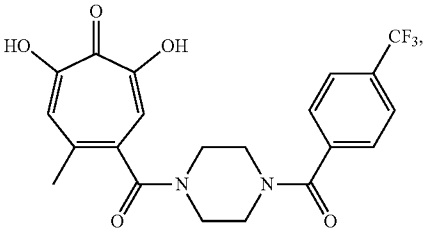

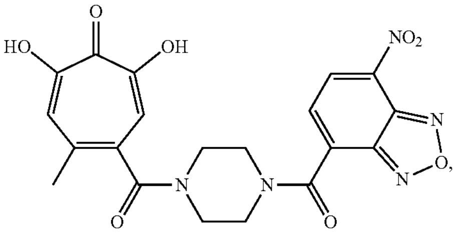

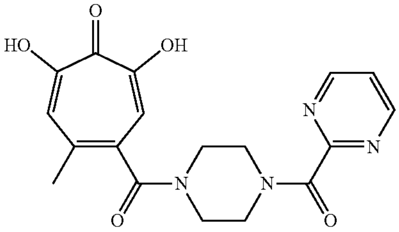

,

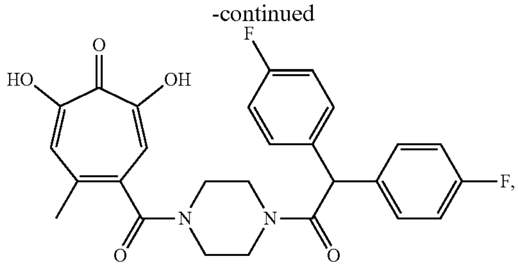
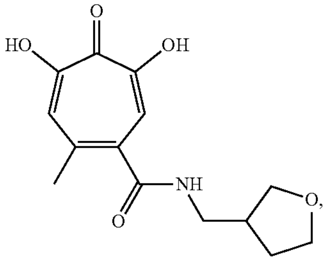
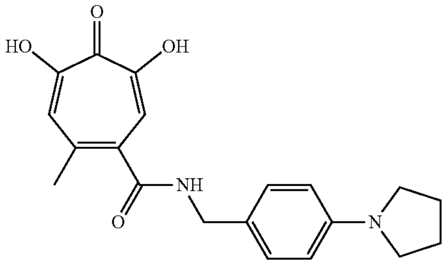
,
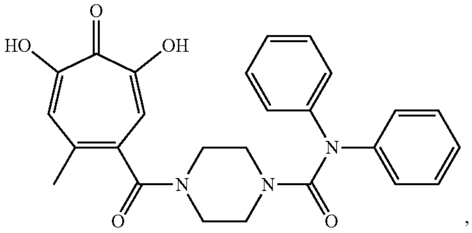
,
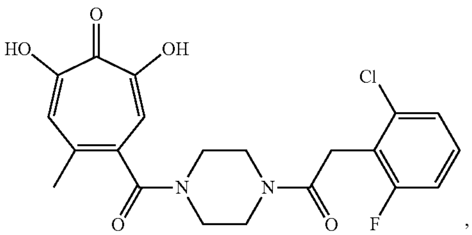
,
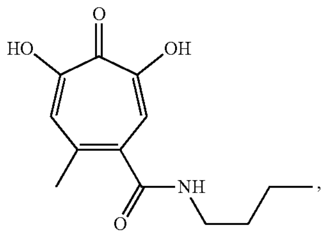
,
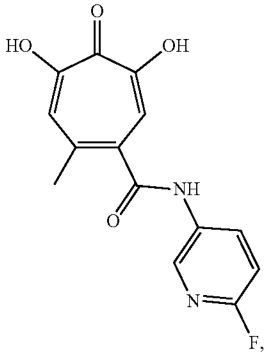
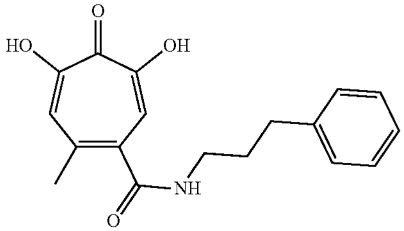
,
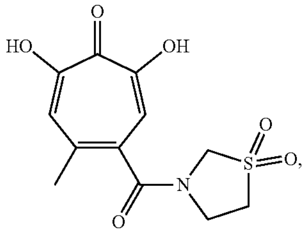
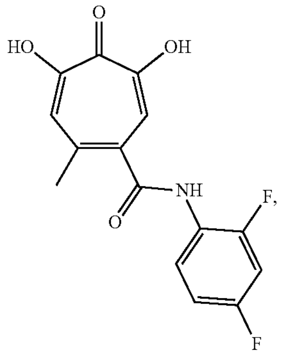
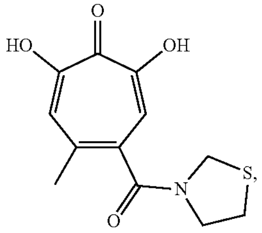
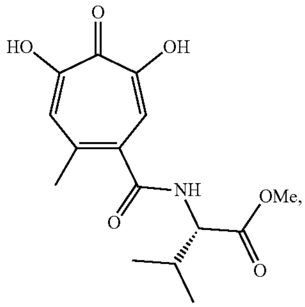

-continued
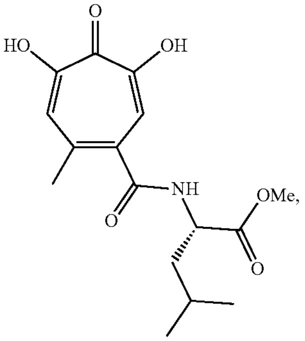
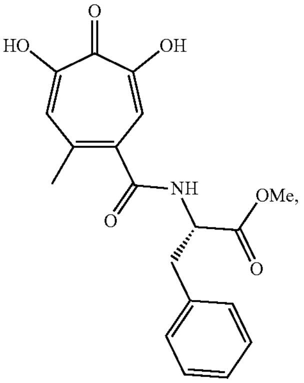
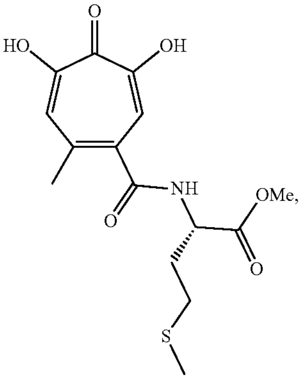
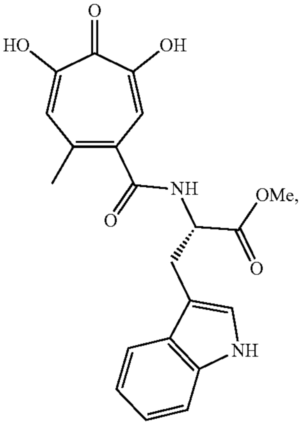
-continued
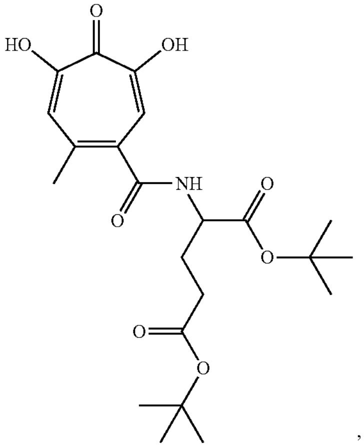
,
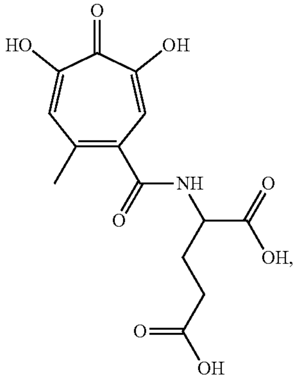
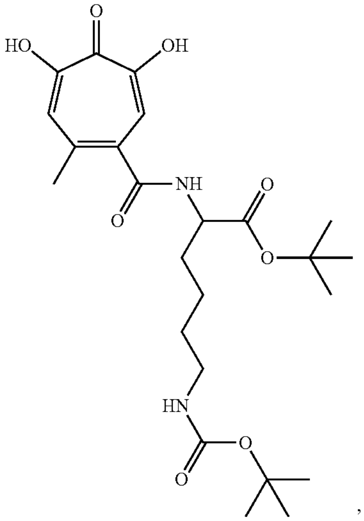
,
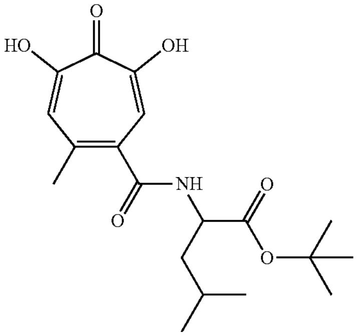
, -continued
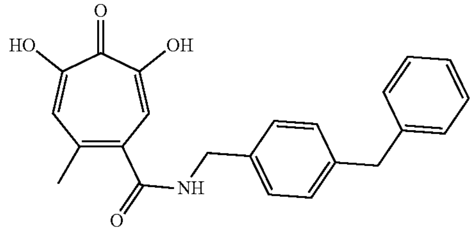
,
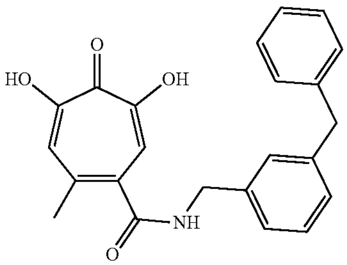
,
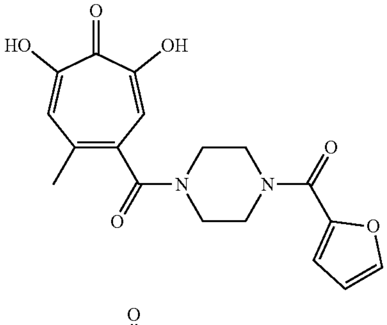
,
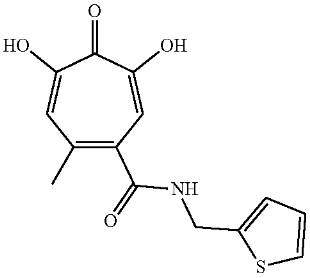
,
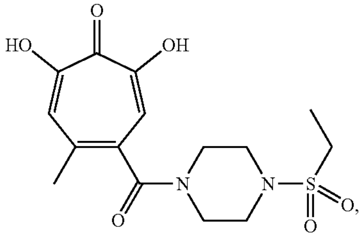
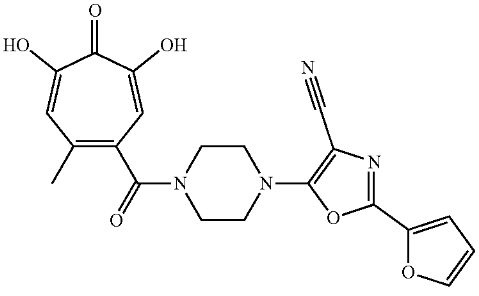
,
-continued
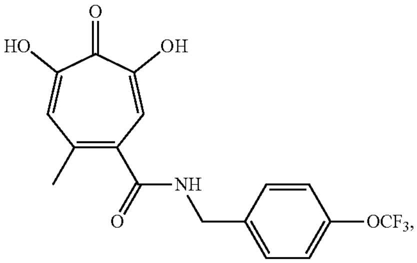
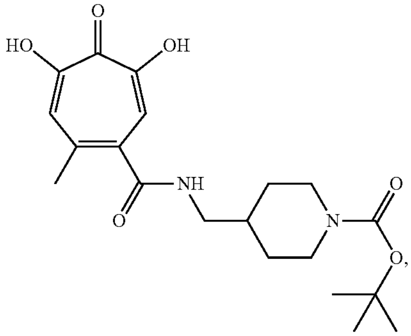
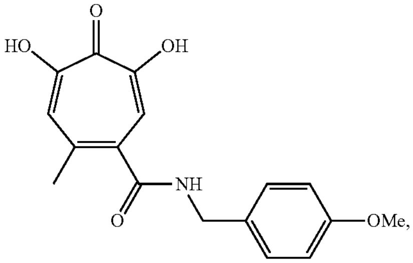
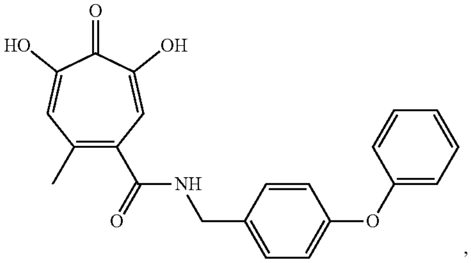
,
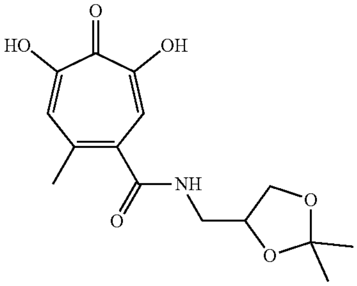
,
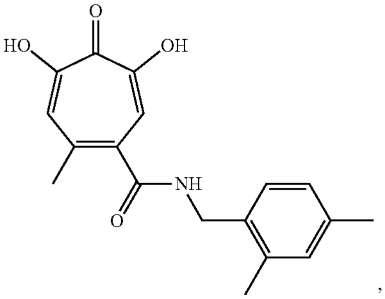
, -continued
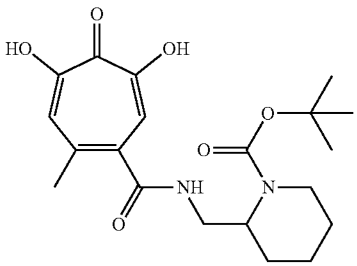
,
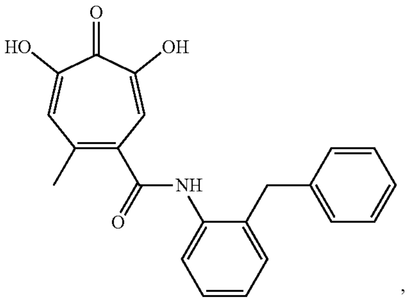
,
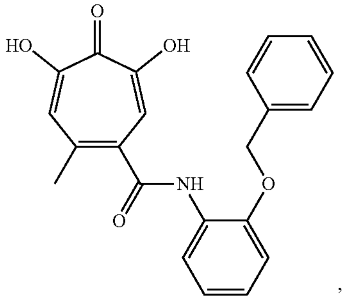
,
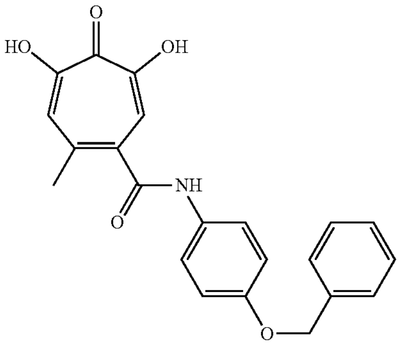
,
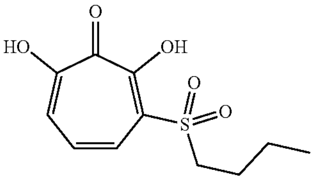
,
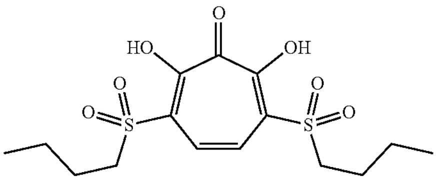
,
-continued
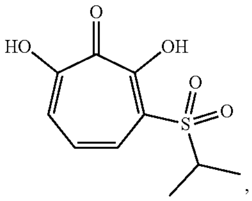
,
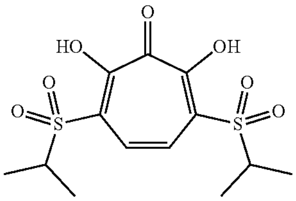
,
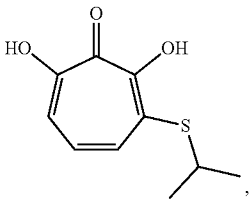
,
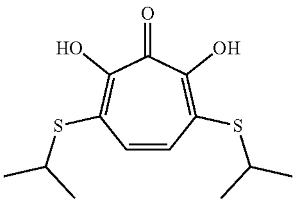
,
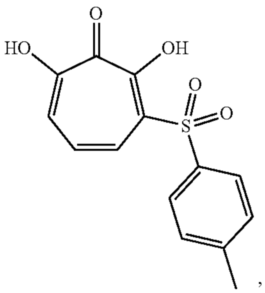
,
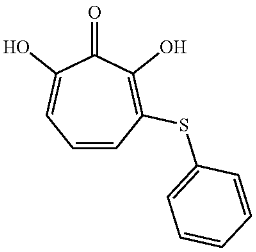
,
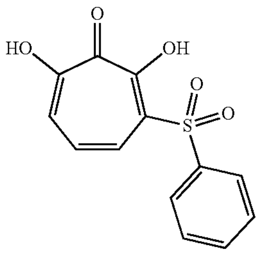
,
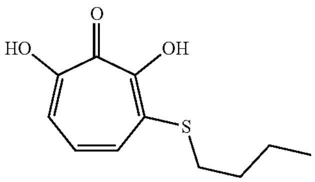
,
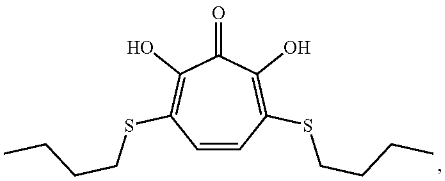
,
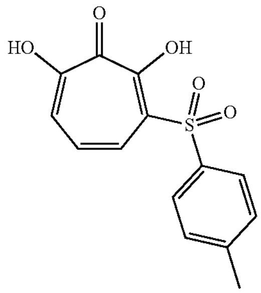
, -continued
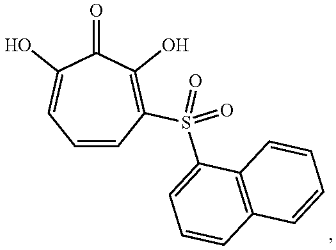,
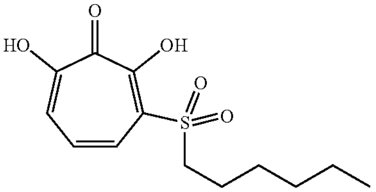,
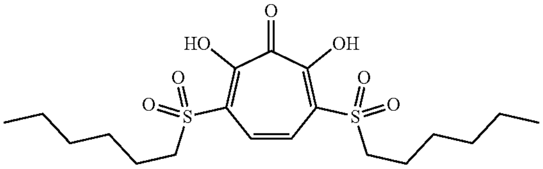,
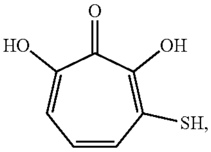
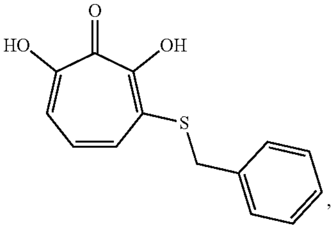,
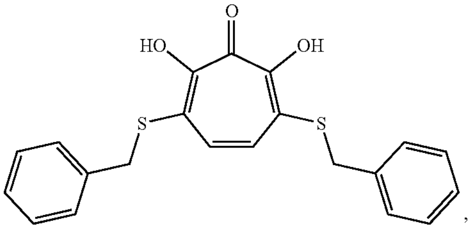,
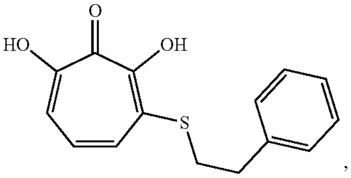,
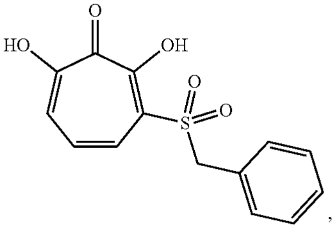,
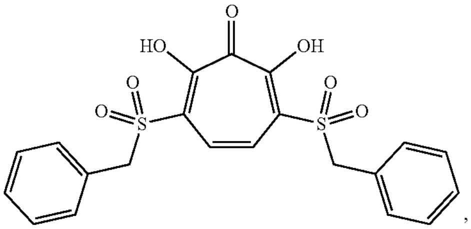,
-continued
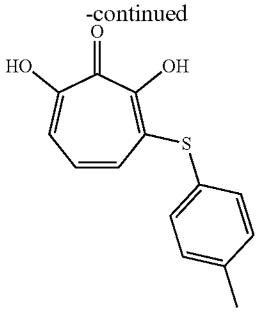,
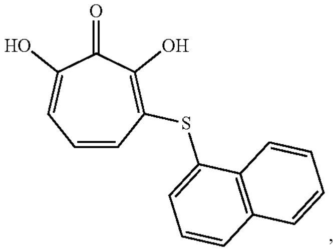,
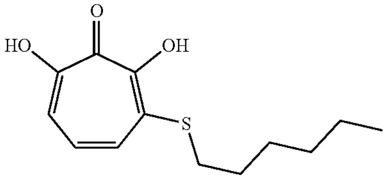,
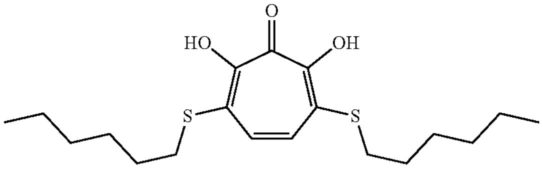,
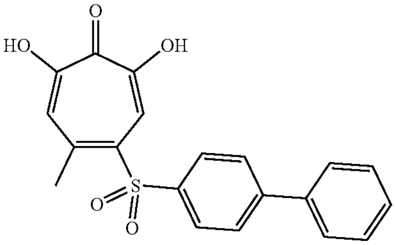,
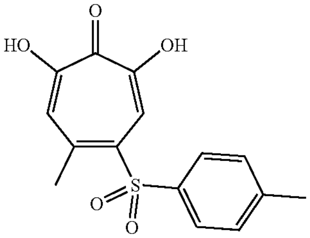,
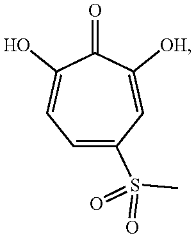
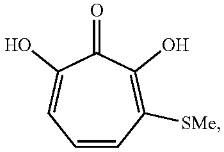
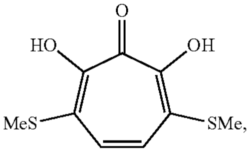
or
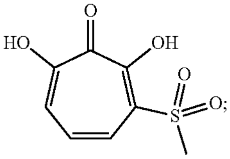
or a pharmaceutical salt thereof.

16. A pharmaceutical composition comprising:
(A) a compound of claim 1; and
(B) an excipient.

* * * * *